US012636303B2

(12) United States Patent
Nagpal

(10) Patent No.: US 12,636,303 B2
(45) Date of Patent: May 26, 2026

(54) COMPOSITION OF A THERAPEUTIC OLIGOMER

(71) Applicant: Sachi Bioworks Inc., Louisville, CO (US)

(72) Inventor: Prashant Nagpal, Lafayette, CO (US)

( * ) Notice: Subject to any disclaimer, the term of this patent is extended or adjusted under 35 U.S.C. 154(b) by 588 days.

(21) Appl. No.: 18/079,312

(22) Filed: Dec. 12, 2022

(65) Prior Publication Data

US 2023/0116385 A1 Apr. 13, 2023

Related U.S. Application Data

(63) Continuation-in-part of application No. 17/460,968, filed on Aug. 30, 2021, now Pat. No. 11,530,406.

(51) Int. Cl.
*A61K 31/7125* (2006.01)

(52) U.S. Cl.
CPC ................................ *A61K 31/7125* (2013.01)

(58) Field of Classification Search
CPC .................................................. A61K 31/7125
See application file for complete search history.

(56) References Cited

U.S. PATENT DOCUMENTS

| | | |
|---|---|---|
| 7,629,151 B2 | 12/2009 | Gold et al. |
| 8,354,093 B2 | 1/2013 | Becker et al. |
| 2006/0014172 A1 | 1/2006 | Muller et al. |
| 2013/0059296 A1 | 3/2013 | Jacobson et al. |
| 2016/0038528 A1 | 2/2016 | Malone et al. |
| 2016/0053260 A1 | 2/2016 | Mirkin et al. |
| 2016/0287152 A1 | 10/2016 | Schwartz et al. |
| 2019/0002814 A1 | 1/2019 | Masquelier et al. |
| 2019/0255106 A1 * | 8/2019 | Lande .................... C12N 15/63 |
| 2019/0321488 A1 | 10/2019 | Hanes et al. |
| 2020/0115705 A1 | 4/2020 | Mason et al. |
| 2020/0123535 A1 | 4/2020 | Sunspiral et al. |
| 2020/0172967 A1 | 6/2020 | Gines et al. |

| | | |
|---|---|---|
| 2020/0283798 A1 | 9/2020 | Minshull et al. |
| 2020/0370058 A1 | 11/2020 | Davis et al. |
| 2021/0071172 A1 | 3/2021 | Lipkin et al. |

FOREIGN PATENT DOCUMENTS

| | | |
|---|---|---|
| WO | 2014197091 | 12/2014 |
| WO | 2020223705 | 11/2020 |

OTHER PUBLICATIONS

Product Brochure for the Symphony® Multiple Peptide Synthesis Station from Protein Technologies, Inc., available 2006, downloaded Aug. 19, 2025 from https://www.stepbio.it/public/pdf/pti_symphony.pdf) (Year: 2006).*
Kelsey R. Beavers, Jeremy W. Mares, Caleb M. Swartz, Yiliang Zhao, Sharon M. Weiss, and Craig L. Duvall, In Situ Synthesis of Peptide Nucleic Acids in Porous Silicon for Drug Delivery and Biosensing, Jun. 20, 2014.
Richard Owczarzy 1, Andrey V Tataurov, Yihe Wu, Jeffrey A Manthey, Kyle A McQuisten, Hakeem G Almabrazi, Kent F Pedersen, Yuan Lin, Justin Garretson, Neil O Mcentaggart, Chris a Sailor, Robert B Dawson, Andrew S Peek, IDT SciTools: a suite for analysis and design of nucleic acid oligomers, Jul. 1, 2008.
Colin M Calabrese, Timothy J Merkel, William E Briley , Pratik S Randeria, Suguna P Narayan, Jessica L Rouge, David a Walker, Alexander W Scott, Chad A Mirki, Biocompatible Infinite-Coordination-Polymer Nanoparticle-NucleicAcid Conjugates for Antisense Gene Regulation, Jan. 7, 2015.

* cited by examiner

*Primary Examiner* — Michael P Cohen

(74) *Attorney, Agent, or Firm* — CALDWELL LLC

(57) ABSTRACT

A system for producing a therapeutic oligomer includes a computing device configured to design a proposed therapeutic oligomer sequence, wherein designing further comprises generating a genomic library for an organism from a gene target, initiating a sequence identification function, identifying a genomic locus that the proposed therapeutic oligomer sequence is predicted to bond to as a function of an off-target sequence function, selecting the proposed therapeutic oligomer sequence as a function of the sequence identification function, the genomic locus, and a criterion element, and synthesize a therapeutic oligomer as a function of the proposed therapeutic oligomer sequence.

24 Claims, 31 Drawing Sheets

COMPOSITION OF A THERAPEUTIC OLIGOMER

CROSS-REFERENCE TO RELATED APPLICATIONS

This application is a continuation-in-part of Non-provisional application Ser. No. 17/460,968 filed on Aug. 30, 2021, and entitled "SYSTEM AND METHOD FOR PRODUCING A THERAPEUTIC OLIGOMER," the entirety of which is incorporated herein by reference.

FIELD OF THE INVENTION

The present invention generally relates to the field of oligonucleotide synthesis. In particular, the present invention is directed to a system and method for producing a therapeutic oligomer.

BACKGROUND

An encroaching crisis of limited pharmaceutical treatment options is rising exponentially. This is further complicated by the dwindling pipeline of treatment options for many healthcare challenges.

SUMMARY OF THE DISCLOSURE

In an aspect, therapeutic oligomer composition includes a therapeutic oligomer configured to regulate gene expression of a gene target within a target host. The therapeutic oligomer additionally includes at least peptide nucleic acid (PNA) comprising at least synthetic DNA-analog and a (2-aminoethyl) glycine carbonyl unit.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4 is a diagrammatic representation illustrating an exemplary embodiment of a peptide synthesis;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to a composition of a therapeutic oligomer. The composition includes a therapeutic oligomer configured to regulate gene expression of a gene target within a target host. The therapeutic oligomer additionally includes at least peptide nucleic acid (PNA) comprising at least synthetic DNA-analog, wherein the at least peptide nucleic acid (PNA) comprises a (2-aminoethyl) glycine carbonyl unit.

Figure 1:
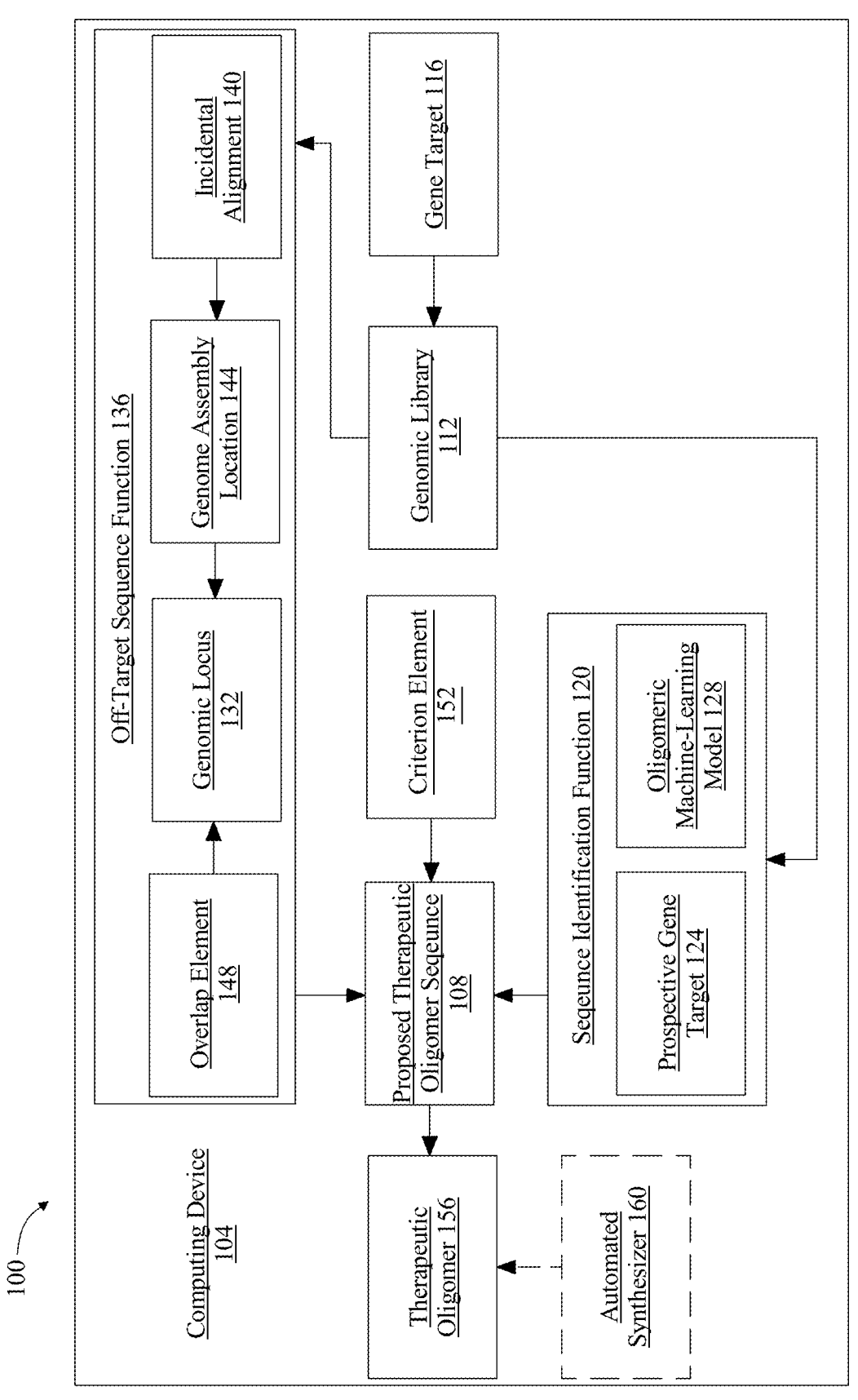
FIG. 1 is a block diagram illustrating a system for producing a therapeutic oligomer.

Referring now to FIG. 1, an exemplary embodiment of a system 100 for producing a therapeutic oligomer is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, a "therapeutic oligomer," as used herein, is a polymer comprising relatively few repeating units that may produce a therapeutic effect as a function of regulating an expression of one or more genes and/or polynucleotides. As used in this disclosure a "therapeutic effect" is a response of an organism that occurs as a function of an external stimulus, such as but not limited to an oligomer. In an embodiment, and without limitation, an organism may include one or more archaea, bacteria, eukarya, and the like thereof. For example, and without limitation, organisms may include one or more prokaryota cells, halophiles, hyperthermophiles, and the like thereof. As a further non-limiting example, organisms may include one or more bacteria. As a further non-limiting example, organisms may include one or more humans, pets, animals, and the like thereof. As used in this disclosure a "polynucleotide," is a single nucleotide and/or a polymer of nucleic acid residues of any length. In an embodiment, polynucleotide may contain deoxyribonucleotides, ribonucleotides, and/or their analogs and may be double-stranded or single stranded. Polynucleotide may comprise modified nucleic acids (e.g., methylated), nucleic acid analogs and/or non-naturally occurring nucleic acids and may be interrupted by non-nucleic acid residues. For example, and without limitation, polynucleotide may include a gene, a gene fragment, cDNA, isolated DNA, mRNA, tRNA, rRNA, isolated RNA of any sequence, recombinant polynucleotides, primers, probes, plasmids, vectors, and the like thereof. In an embodiment, and without limitation, polynucleotide may include nucleic acid polymers that have been modified, whether naturally or by intervention.

In an embodiment, and still referring to FIG. 1, proposed therapeutic oligomer sequence 108 may include a proposed peptide nucleic acid (PNA). As used in this disclosure a "peptide nucleic acid" is a DNA analog comprising a (2-aminoethyl) glycine carbonyl unit, as opposed to a phosphate backbone, that is linked to a nucleotide base by the glycine amino nitrogen and/or methylene linker. In an embodiment, and without limitation, proposed PNA may include a backbone composed of peptide bonds linking nucleobases. In another embodiment, and without limitation, proposed PNA may include an amino-terminal and/or a carboxy-terminal end. In another embodiment, and without limitation, proposed PNA may include a 5' and/or a 3' end in the conventional sense, with reference to the complementary nucleic acid sequence to which it specifically hybridizes. In an embodiment, proposed PNA may include a sequence that may be described in a conventional fashion similar to DNA and/or RNA, such as but not limited to having nucleotides including guanine (G), uracil (U), thymine (T), adenine (A), and/or cytosine (C) which may correspond to a nucleotide sequence of a DNA molecule. In an embodiment, proposed PNA may be synthesized using an automated DNA synthesized, as described below in detail. In an embodiment, proposed PNA may be resistant to proteases and/or nucleases as a function of a structural difference from DNA, wherein the structure difference may result in proposed PNA not being recognized by a hepatic transporter(s) recognizing DNA. In another embodiment, proposed PNA may comprise at least one modified phosphate backbone such as, but not limited to phosphorothioate, phosphorodithioate, 5-phosphoramidothioate, phosphoramidate, phosphordiamidate, methylphosphonate, alkyl phosphotriester, formacetal, and/or the like thereof. Additionally or alternatively, proposed therapeutic oligomer may include an antisense oligonucleotide. As used in this disclosure an "antisense oligonucleotide" is an antisense molecule that modulates the expression of one or more genes and/or polynucleotides. For example, and without limitation, antisense oligonucleotide may include antisense PNAs, antisense RNAs, and the like thereof. In another embodiment, antisense oligonucleotides may include RNA and/or DNA oligomers such as but not limited to interfering RNA molecules, such as dsRNA, dsDNA, mRNA, siRNA, and/or hpRNA as well as locked nucleic acids, BNA, polypeptides and/or other oligomers and the like thereof.

With continued reference to FIG. 1, the nucleic acid-binding domain of therapeutic oligomer 108 may be a peptide nucleic acid (PNA). In embodiments, PNA may comprise a synthetic DNA-analog where the phosphodiester bond is replaced with 2-N-aminoethylglycine units. As used in the current disclosure, a "synthetic DNA-analog" is a man-made compound which is analogous structurally to naturally occurring RNA and DNA. Nucleic acids are chains of nucleotides, which are composed of three parts: a phosphate backbone, a pentose sugar, either ribose or deoxyribose, and one of four nucleobases. A synthetic DNA-analog may have one or more of these parts. In some embodiments, the synthetic DNA-analogs nucleobases confer, among other things, different base pairing and base stacking properties. Examples include universal bases, which can pair with all four canonical bases, and phosphate-sugar backbone analogues such as PNA, which affect the properties of the chain (PNA can even form a triple helix). Artificial nucleic acids include peptide nucleic acid (PNA), Morpholino and locked nucleic acid (LNA), as well as glycol nucleic acid (GNA), threose nucleic acid (TNA) and hexitol nucleic acids (HNA). Each of these is distinguished from naturally occurring DNA or RNA by changes to the backbone of the molecule. As used in the current disclosure, a "phosphodiester bond" is when exactly two of the hydroxyl groups (—OH) in phosphoric acid react with hydroxyl groups on other molecules to form two ester bonds, wherein the bonds make up the backbones of DNA and RNA. The "bond" involves this linkage C—O—PO-2O—C. The phosphate is attached to the 5' carbon. The 3' carbon of one sugar is bonded to the 5' phosphate of the adjacent sugar. Specifically, the phosphodiester bond links the 3' carbon atom of one sugar molecule and the 5' carbon atom of another. These saccharide groups are derived from deoxyribose in DNA and ribose in RNA. Phosphodiesters are negatively charged at pH 7. Repulsion between these negative charges influences the conformation of the polynucleic acids. The negative charge attracts histones, metal cations such as magnesium, and polyamines. PNA may include 2-N-aminoethylglycin. In some embodiments, 2-N-aminoethylglycin may be identified by its molecular formula of C4H10N2O2.

Further referring to FIG. 1, therapeutic oligomer 108 may include a nanoparticle binding element. A "nanoparticle binding element," as used in this disclosure, is monomer, oligomer, and/or polymer that acts to attach a sequence having a therapeutic effect, such as an therapeutic oligomer sequence, to a nanoparticle as described in further detail below. Nanoparticle binding element may include a first end attached to the therapeutic oligomer sequence, where attachment may be performed using any form of chemical, covalent, and/or ionic bond, including bonds effected using a polymerase. Nanoparticle binding element may include a second end, which may be an opposite end of the nanoparticle binding element from the first end. Nanoparticle binding element may function, without limitation, as a nanoparticle-binding domain (NBD), which may include a peptide or other sequence added to combine with therapeutic oligomer 108, therapeutic elements, and/or sequences for conjugation and/or attachment with a nanoparticle. In an embodiment, this may allow for rapid and/or low-cost and scalable purification of full-sequence peptide-backbone-based molecules, while attaching desired elements to form a nanoligomer for active transport. Typical NBD sequences used with gold nanoparticles may include HHHHH (5-histidine), cysteine or the like. Once attached to a nanoparticle, such sequences and/or elements may also allow selective attachment and potential folding of peptide and PNA-based sequences, to keep low hydrodynamic size, especially for brain delivery.

Continuing to refer to FIG. 1, the therapeutic oligomer 108 may include a delivery nanoparticle attached to the second end of the nanoparticle binding element. A "delivery nanoparticle," as used in this disclosure, is a small nanoparticle, such as a nanoparticle less than 2 nm in diameter, used for purification and transport, for instance to cross the blood-brain barrier. The total hydrodynamic size of a nanoligomer formed by combining all elements of the oligomer may be kept at less than 2 nm to promote efficient transport to the brain. Typical FDA GRAS (generally regarded as safe) materials used may include gold or zinc oxide. Nanoparticle material and size may be screened for redox potential (to screen for degradation issues), potential to generate reactive oxygen species (ROS), and some other biological redox considerations, before it is approved for further nanoligomer use. For example, in past use cases, Au22 and Au25 were selected based on the biological redox and the above screening criterion.

Still referring to FIG. 1, therapeutic oligomer 108 may include a coating and/or one or more surface elements to aid in uptake into cells. Such coating and/or surface elements may function as a cellular Uptake Domain (CUD). CUD elements may include, without limitation, short amino acid coatings on nanoparticles to promote active diffusion through cell surface receptors. In a non-limiting example, charge-neutral and/or zwitterionic amino acids may be used to prevent protein corona during transport through cell media, blood serum/others, to keep a low hydrodynamic radius for efficient transport, and prevent any immunogenic response. Amino acid binding chemistry may be tested to ensure stable binding, active diffusion. For instance, and without limitation, amino acid coatings may be tested by using less than 1-5% cell volume in vitro; testing may be expected to uptake at least 20-95% nanoligomers (benchmark) in uptake studies with specific cell types, to screen and use in further testing in vitro and in vivo. Stability may be tested through identification of NBD domains in free cell media, pKa, serum test, or the like. Typical examples of CUD coatings used and validated may include, without limitation, cysteine and/or glutathione with gold nanoparticles.

Still referring to FIG. 1, where therapeutic oligomer sequence performs transcriptional downregulation, therapeutic oligomer sequence may include a nuclear localization sequence (NLS). "Transcriptional downregulation," as used herein, is a process or action whereby transcription of a genetic sequence from DNA to RNA is reduced or halted for a protein to be suppressed by therapeutic oligomer sequence. A "nuclear localization sequence," as used in this disclosure, is a sequence of monomers, which may include without limitation a peptide sequence, that aids in insertion of an oligomer and/or nano-oligomer into a nucleus of a cell; in an embodiment, this may enable the therapeutic oligomer sequence to interfere with transcription at the site where it occurs. NLS peptide sequences may include, without limitation, sequence PKKKRKV (Proline-Lysine-Lysine-Lysine-Arginine-Lysine-Valine), which is used as a nuclear localization signal by variants of simian virus 40 (SV40) and which has been shown to enable localization/nuclear uptake. As a further non-limiting example, sequences from nucleoplamsin, such as AVKRPAATKKAGQAKKKKLD may be used for NLS. In another non-limiting example, sequences from c-Myc such as PAAKRVKLD peptide sequence may be used as an NLS. As yet another non-limiting example, an NLS may include EGL-13 sequences such as without limitation MSRRRKANPTKLSENAKKLAKEVEN is not frequently used, but part of the Sachi design strategy. As another non-limiting example, NLS may include TUS-protein sequences such as KLKIKRPVK.

With continued reference to FIG. 1, therapeutic oligomer sequence may alternatively or additionally perform translational downregulation. As used in this disclosure, "translational downregulation" is a process whereby translation from a nucleotide sequence to an amino acid sequence and/or protein is inhibited and/or blocked. For instance, and without limitation, translational downregulation may be performed by preventing entry of MRNA into ribosomes, preventing MRNA from interacting with TRNA, denaturing MRNA, binding to MRNA, or the like. As a non-limiting example, a therapeutic oligomer may bind to MRNA that codes a protein and/or amino acid sequence to be downregulated, preventing translation of that MRNA into that protein and/or amino acid sequence. In some embodiments, translational downregulation may not require entry into a cellular nucleus or other location containing DNA and/or chromosomes; transcriptional downregulation may be performed, for instance, in cytoplasm. A therapeutic oligomer performing translational down regulation may not require and/or include a nuclear location sequence.

In an embodiment, and still referring to FIG. 1, proposed therapeutic oligomer may be designed to regulate expression of a gene target 116 in a host organism. For example, and without limitation, proposed therapeutic oligomer may be designed to treat a bacterial infection, such as but not limited to a multi-drug resistant (MDR) bacterial infection. As a further non-limiting example, proposed therapeutic oligomer sequence 108 may be designed to treat and/or mitigate a microbiome disease, such as but not limited to treating one or more microbiota, and/or genes associated to the microbiome disease. As a further non-limiting example, proposed therapeutic oligomer sequence 108 may be designed to treat and/or mitigate an immune disease, such as but not limited to Addison's disease, celiac disease, dermatomyositis, Graves' disease, Hashimoto thyroiditis, Multiple Sclerosis, Myasthenia gravis, Pernicious anemia, and the like thereof. As a further non-limiting example, proposed therapeutic oligomer sequence 108 may be designed to treat and/or mitigate an oncological disease, such as but not limited to breast cancer, lung cancer, colon cancer, rectum cancer, prostate cancer, skin cancer, stomach cancer, and the like thereof. As a further non-limiting example, proposed therapeutic oligomer sequence 108 may be designed to treat and/or mitigate a protein disorder, such as but not limited to Parkinson's disease, Huntington's disease, Creutzfeldt-Jakob disease, cystic fibrosis, Gaucher's disease, and the like thereof. As a further non-limiting example, proposed therapeutic oligomer sequence 108 may be designed to treat and/or mitigate a neurodegenerative disease such as but not limited to Alzheimer's disease, Multiple Sclerosis, amyotrophic lateral sclerosis, Parkinson's disease, Prion Disease and the like thereof. As a further non-limiting example, proposed therapeutic oligomer sequence 108 may be designed to treat and/or mitigate an infectious disease, such as but not limited to chickenpox, influenza, diphtheria, giardiasis, infectious mononucleosis, Herpes Simplex Virus 1, Herpes Simplex Virus 2, syphilis, shigellosis, *chlamydia*, influenza A, influenza B, SARS-CoV-2, COVID-19, and the like thereof. Additionally or alternatively, proposed therapeutic oligomer sequence 108 may be designed to treat and/or mitigate a viral agent and/or infectious agent such as a bacterium, virus, and the like thereof.

Still referring to FIG. 1, computing device 104 generates a genomic library 112 for an organism. As used in this disclosure a "genomic library" is a database of genomic information that relates to a host organism. As used in this disclosure "genomic information" is data and/or genetic material that codes one or more genomes. For example, and without limitation, genomic information may include DNA, RNA, and the like thereof. In an embodiment, and without limitation, genomic information may include coding regions of DNA and/or RNA and/or non-coding regions of DNA and/or RNA. In another embodiment, and without limitation, genomic information may include mitochondrial DNA and/or RNA, chloroplast DNA and/or RNA, and the like thereof. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Still referring to FIG. 1, genomic library 112 may include one or more inputs such as a PNA sequence length and/or a pair of gene coordinates relative to a +1 translation start site. In an embodiment, and without limitation, genomic library 112 may include sequence warning inputs and/or STRING protein analysis inputs, wherein a sequence warning is described below in detail. In an embodiment, and without limitation, genomic library 112 for an organism may include a list of gene identifiers (IDs). For example, and without limitation, gene IDs may represent the genes of the given organism as a function of a genome assembly and/or annotation file. In another embodiment, and without limitation, genomic library 112 for an organism may include a genome assembly for a target organism, wherein a target organism may include a human organism and/or a non-human organism. In another embodiment, and without limitation, genomic library 112 for an organism may include a corresponding GFF annotation file. In an embodiment, and without limitation, genomic library 112 may include a "Get Sequences" tool that may read a gene ID and, for each list entry, search through the GFF file for any coding sequence feature (designated in GFF format as "CDS") or parent gene feature that has a matching identifier. Upon finding a matching coding sequence, "Get Sequence" tool may extract the feature name, the start and end genomic coordinates, the feature strand, and/or any other additional information in genomic library 112.

Still referring to FIG. 1, computing device 104 generates genomic library 112 for an organism from a gene target 116. As used in this disclosure a "gene target" is a gene of interest that is encoded in a nucleic acid sequence. In another embodiment, and without limitation, gene target 116 may include one or more nucleic acid sequences such as, but not limited to, chromosomes, plasmids, DNA, RNA, dsRNA, dsDNA, mRNA, siRNA, tRBA, hpRNA, and the like thereof. In an embodiment, and without limitation gene target 116 may include a known gene target. For example, and without limitation, gene target 116 may be known as a function of a whole genome assembly. As used in this disclosure a "whole genome assembly" is a sequence composition of an entire genome within the cell of an organism. For example, and without limitation, whole genome assembly may be identified as a function of a whole-genome sequencing. In an embodiment, and without limitation, whole-genome sequencing may be performed to identify a resistance factor, create a genome assembly that may be used for antisense PNA design, and/or search for genomic contributions to a resistance phenotype. For example, and without limitation, whole-genome sequencing may be performed to determine a genome assembly for one or more viral agents such as but not limited to SARS-CoV-2. For example, and without limitation, whole-genome sequencing may include using an ARG-ANNOT database, IHU Mediterranean Infection, Marseille, France, to identify a genome strain that encodes fifteen genes related to a microbiome disease. Additionally or alternatively whole-genome sequencing may be stored as genomic library 112.

In an embodiment, and still referring to FIG. 1, gene target 116 may be known as a function of a partial genome assembly. As used in this disclosure a "partial genome assembly" is a sequence composition of a portion of a genome within the cell of an organism. For example, and without limitation, partial genome assembly may be identified as a function of a partial-genome sequencing. For example, and without limitation, partial-genome sequencing may include performing small RNA sequencing to search for potential PNA targets among short nucleic acids potentially involved in gene regulation. In an embodiment, and without limitation, small RNA may influence pathogen response and/or viral agent response. In another embodiment, and without limitation, small RNA may be isolated as a function of an RNA isolation protocol enriched for sRNA prior to sequencing, wherein sequencing data may allow for identification of previously documented sRNA and/or novel RNAs. In an embodiment, and without limitation, small RNA sequencing may determine an overlap of DE genes between single time points. Additionally or alternatively, small RNA sequencing may identify 22 sRNAs, such as but not limited to known regulatory sRNAs (dicF, ssrA), annotated short protein coding genes (ilvB, acpP, bolA, csrA, ihfA, lspA), small putative protein-coding genes (dsrB, yahM, ybcJ, ygdI, ygdR, ytfK), small transcripts antisense to coding genes (ygaC, hemN, ECUMN_1534/5), and/or novel predicted transcripts. In an embodiment, and without limitation, small RNA sequencing may allow gene target selection such as, but not limited to selecting three genes of interest, wherein the three genes of interest may be without limitation bola, dsrB, ygaC, and the like thereof. Additionally or alternatively, The RNA sequencing partial genome sequencing may be stored in genomic library 112. Additionally or alternatively, partial genome assembly may denote one or more genomic sequence compositions that code for a microbiome disease, immune disease, oncological disease, protein disorder, neurodegenerative disease, infectious disease, and the like thereof.

Still referring to FIG. 1, a gene target 116 may include proinflammatory cytokines. Proinflammatory cytokines may include Interleukin-1β or IL-1β, tumor necrosis factor-alpha or TNF-α, TNF receptor 1 or TNF-R1, Interleukin 6 or IL-6, Interleukin 10 (IL-10), inflammasomes (e.g., NLRP1), Granulocyte-Macrophage Colony-Stimulating Factor (GM-CSF), key transcription factors (e.g., nuclear factor kappa-B or NF-κβ) and their combinations, as upstream regulators, and canonical pathway targets, to identify and validate the best-in-class treatment. Cytokines may be regulators of host responses to infection, immune responses, inflammation, and trauma. Some cytokines act to make disease worse (proinflammatory), whereas others serve to reduce inflammation and promote healing (anti-inflammatory). Proinflammatory cytokines may effect a plurality of the host in a plurality of ways including creating neuroinflammation. Additionally, a gene target 116 may include an inflammasome acquisition frenzy cytokines. Examples of inflammasome acquisition frenzy cytokines may include NLRP3 and NFKB inhibitors.

Still referring to FIG. 1, gene target 116 may be known as a function of a biosynthetic gene cluster derived from a microbiome gene analysis. As used in this disclosure a "biosynthetic gene cluster" is a linked set of genes that participate in a common biosynthetic pathway. As used in this disclosure a "microbiome gene analysis" is a gene analysis of microbiota. In an embodiment, and without limitation, microbiome gene analysis may analyze one or more microbiota present in an individual's gastrointestinal tract. In another embodiment, and without limitation, microbiome gene analysis may determine one or more promoters in bacteria. For example. And without limitation, a promoter may include T7, Sp6, lac, araBad, trp, Ptac, and the like thereof. For example, and without limitation, microbiome gene analysis may include packing five colonies of microbiota from a plate and resuspended in liquid growth media, wherein a "plate," as used herein is a shallow, cylindrical, lidded dish that is used to culture cells. For example, and without limitation, plate may include a petri-dish such as, but not limited to a glass petri-dish, plastic petri-dish, and the like thereof. Plate may include any suitable dish to produce an agar plate. As used in this disclosure an "agar plate" is a petri-dish that comprises a growth medium solidified with agar, wherein a "growth medium," as used herein is a solid, liquid, and/or semi-solid material designed to support the growth of a population of microorganisms and/or cells. In an embodiment, and without limitation, growth medium may aid microorganisms and/or cells in cell proliferation. In another embodiment, and without limitation, agar plate may include one or more agar plates such as, but not limited to a blood agar plate, chocolate agar plate, horse blood agar plate, Thayer-Martin agar plate, Thiosulfate-citrate-bile salts-sucrose agar plate, bile esculin agar, cysteine lactose electrolyte-deficient agar plate, Granada medium agar plate, Hektoen enteric agar plate, Lysogeny broth agar plate, MacConkey agar plate, Mannitol salt agar plate, Mueller-Hinton agar plate, Nutrient agar plate, Önöz agar plate, Phenethyl alcohol agar plate, R2A agar plate, Tryptic soy agar plate, xylose-lysine-deoxycholate agar plate, cetrimide agar plate, tinsdale agar plate, sabouraud agar plate, hay infusion agar plate, potato dextrose agar plate, Knop agar plate, YEPD media agar plate, and the like thereof.

In an embodiment, and still referring to FIG. 1, microbiome gene analysis may include isolating genomic DNA as a function of a purification kit, such as but not limited to a Wizard DNA Purification Kit (Promega, Madison, Wisconsin, U.S.A). In another embodiment, microbiome gene analysis may include extracting RNA as a function of thawing a sample and resuspending the sample in 100 μL TE buffer with 0.4 mg/mL lysozyme and proteinase K, wherein after incubation at room temperature for 5 minutes, 300 μL of lysis buffer with 20 μL/mL β-mercaptoethanol may be added to each and vortexed to mix. Each lysis solution may be split in half, with one half being processed for total RNA isolation followed by DNase treatment with the TURBO DNA-free kit (Ambion, Austin TX, U.S.A.). Small RNA may be isolated using the mirVana miRNA isolation kit (Thermo Scientific, Waltham, MA, U.S.A.). Concentration and A260/A280 may be measured on a Nanodrop 2000 (Thermo Scientific, Waltham, MA, U.S.A.). In another embodiment, microbiome gene analysis may include preparing a sequencing library with library kit, wherein the sequencing library is sequenced as a function of an analyzer such as, but not limited to an Illumina MiSeq, (Illumina, San Diego, California, U.S.A.) In another embodiment, and without limitation, microbiome gene analysis may include identifying a de novo assembly comprising a 5,325,941 bp length, wherein the de novo assembly may contain a GC content of 50.59%. In an embodiment and without limitation, microbiome gene analysis may identify 114 RNA coding sequences, 82 tRNAs, 11 ncRNAs, 260 pseudogenes, and/or 2 CRISPR arrays of a microbiota genome.

Still referring to FIG. 1, computing device 104 initiates a sequence identification function 120. As used in this disclosure a "sequence identification function" is a function and/or algorithm that identifies a genomic sequence and/or target sequence of proposed therapeutic oligomer. Computing device 104 may initiate sequence identification function 120 as a function of identifying a plurality of prospective gene targets 124 as a function of the genomic library. As used in this disclosure a "prospective gene target" is a gene of interest that is encoded in a chromosome, plasmid, DNA, RNA, dsRNA, dsDNA, mRNA, siRNA, tRBA, hpRNA, and the like thereof that may be suitable to be innervated with an oligomer. In an embodiment, and without limitation, identifying a plurality of prospective gene targets 124 as a function of the genomic library may include determining a prospective gene target 124 for a given target pathogen, such as a viral agent and/or genomic sequence. In an embodiment, prospective gene targets 124 may correspond to proteins that are essential for growth and/or inhibit the viral agent and/or pathogen mechanism. As used in this disclosure, the terms "inhibit" and/or "inhibition" means to reduce a molecule, a reaction, an interaction, a gene, an mRNA, and/or a protein's expression, stability, function, and/or activity by a measurable amount, and/or to prevent such entirely. In an embodiment and without limitation inhibitors may be compounds that bind to partially and/or totally block stimulation, decrease, prevent, delay activation, inactivate, desensitize, and/or down regulate a protein, a gene, and/or an mRNA stability, expression, function, and/or activity, such as but not limited to an antagonist. For instance, and without limitation, inhibition may include, be included in, and/or involve translational and/or transcriptional downregulation as described in further detail below. A person of ordinary skill in the art would be aware that any of the DNA and/or mRNA sequences described above can be targeted by antisense inhibitors. In another embodiment, and without limitation, target sequences may be sequences present in one or more agents associated to a microbiome disease, immune disease, oncological disease, protein disorder, neurodegenerative disease, infectious disease, and the like thereof. In an embodiment, and without limitation, inhibition may include inhibiting an inflammatory response. In another embodiment, and without limitation, prospective gene targets 124 may correspond to proteins that are essential for growth and/or inhibit the SARS-CoV2. For example, and without limitation, prospective gene target 124 may correspond to a protein, DNA, RNA, genomic sequence, and the like thereof associated to SARS-CoV2 such that an inhibition may occur. In another embodiment, and without limitation, prospective gene targets 124 may correspond to proteins that are essential for growth and/or inhibit one or more viral agents, pathogens, and the like thereof. In an embodiment, and without limitation, target sequences may be those of the homologous gene or mRNA sequence in a viral agent such as influenza. In another embodiment, and without limitation, target sequences may be those of *E. Coli* and/or the homologous gene or mRNA sequence in another target bacterium. Given the benefit of this disclosure, those of skill in the art will be able to identify a target sequence and design an antisense inhibitor oligomer to target the gene or mRNA sequence. Target sites on DNA and/or RNA (e.g. sRNA) associated with antibiotic resistance may be any site to which binding of an antisense oligomer may inhibit the function of the DNA or RNA sequence. Inhibition may be caused by steric interference resulting from an antisense oligomer binding the DNA and/or RNA sequence such that a prevention of proper transcription of the DNA sequence and/or translation of the RNA sequence occurs.

Still referring to FIG. 1, computing device 104 may identify a plurality of prospective gene targets 124 as a function of a PNA Finder toolbox. As used in this disclosure a "PNA Finder toolbox" is a toll that provides the user with a list of candidate PNA sequences as well as several selection criteria that may be used to predict the efficacy of a given candidate. In an embodiment and without limitation, PNA Finder toolbox may allow a user to filter the list of prospective PNA candidates and synthesize identify the most promising sequence. The prospective PNA with the most promising sequence may then be quickly subjected to efficacy testing in bacterial cultures, microbiome disease cultures, immune disease cultures, oncological disease cultures, protein disorder cultures, neurodegenerative disease cultures, infectious disease cultures, and the like thereof and the resultant data may be used to both select the optimal PNA antibiotic, antiviral, and/or therapeutic and to inform and improve upon the PNA Finder selection process, wherein efficacy testing is described below in detail. In an embodiment, PNA Finder toolbox may be built using Python 2.7. Additionally, in order to run on a Windows operating system, the toolbox may incorporate the program Cygwin to provide a Unix-like environment. The user interface for the PNA Finder Toolbox may also constructed using the Python 2.7 package Tkinter, version 8.5.

Still referring to FIG. 1, computing device 104 generates proposed therapeutic oligomer sequence 108 as a function of prospective gene targets 124 and an oligomeric machine learning model 128. As used in this disclosure an "oligomeric machine-learning model" is a machine-learning model to generate a proposed therapeutic oligomer output given prospective gene targets 124 as inputs, wherein a machine-learning model incorporates a machine-learning process, and wherein "machine-learning process," as used herein, is a process that automatedly uses a body of data known as "training data" and/or a "training set" to generate an algorithm that will be performed by a computing device/ module to produce outputs given data provided as inputs; this is in contrast to a non-machine learning software program where the commands to be executed are determined in advance by a user and written in a programming language. Oligomeric machine-learning model 128 may include one or more oligomeric machine-learning processes such as supervised, unsupervised, or reinforcement machine-learning processes that computing device and/or a remote device may or may not use in the determination of proposed therapeutic oligomer. As used in this disclosure "remote device" is an external device to computing device. Oligomeric machine-learning process may include, without limitation machine learning processes such as simple linear regression, multiple linear regression, polynomial regression, support vector regression, ridge regression, lasso regression, elastienet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, oligomeric machine-learning model 128 is trained as a function of an oligomeric training set. As used in this disclosure an "oligomeric training set" is a training set that correlates the plurality of prospective gene targets 124 and/or an oligomer that regulates gene expression to a proposed therapeutic oligomer sequence, wherein a gene expression is a process that synthesizes a functional gene product from a gene as described below, in reference to FIG. 2. For example, and without limitation, a prospective gene target of Granulocyte colony-stimulating factor (G-CSF) and an oligomer that inhibits gene expression of acute radiation syndrome (ARS) may relate to a proposed therapeutic oligomer sequence of a PNA initiators and/or PNA activators. The oligomeric training set may be received as a function of user-entered valuations of prospective gene targets, oligomers that regulate gene expression, and/or proposed therapeutic oligomer sequences. Computing device 104 may receive oligomeric training set by receiving correlations of prospective gene targets 124 and/or oligomers that regulate gene expression that were previously received and/or identified during a previous iteration of generating a proposed therapeutic oligomer sequence. The oligomeric training set may be received by one or more remote devices that at least correlate a prospective gene target and/or oligomer that regulates gene expression to a proposed therapeutic oligomer sequence. The oligomeric training set may be received in the form of one or more user-entered correlations of prospective gene targets and/or oligomers that regulate gene expression to proposed therapeutic oligomer sequences.

Still referring to FIG. 1, computing device 104 may receive oligomeric machine-learning model 128 from a remote device that utilizes one or more oligomeric machine learning processes, wherein a remote device is described above in detail. For example, and without limitation, a remote device may include a computing device, external device, processor, and the like thereof. Remote device may perform the oligomeric machine-learning process using the oligomeric training set to generate proposed therapeutic oligomer sequence and transmit the output to computing device. Remote device may transmit a signal, bit, datum, or parameter to computing device that at least relates to proposed therapeutic oligomer sequence. Additionally or alternatively, the remote device may provide an updated machine-learning model. For example, and without limitation, an updated machine-learning model may be comprised of a firmware update, a software update, an oligomeric machine-learning process correction, and the like thereof. As a non-limiting example a software update may incorporate a new prospective gene target that relates to an oligomer that regulates a gene expression. Additionally or alternatively, the updated machine learning model may be transmitted to the remote device, wherein the remote device may replace the oligomeric machine-learning model with the updated machine-learning model and generate proposed therapeutic oligomer sequence 108 as a function of the prospective gene target using the updated machine-learning model. The updated machine-learning model may be transmitted by the remote device and received by computing device as a software update, firmware update, or corrected oligomeric machine-learning model. For example, and without limitation oligomeric machine-learning model may utilize a random forest machine-learning process, wherein the updated machine-learning model may incorporate a gradient boosting machine-learning process.

Still referring to FIG. 1, computing device 104 may generate proposed therapeutic oligomer sequence as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device and/or another device may generate a classifier using a classification algorithm, defined as a process whereby a computing device derives a classifier from training data. Classification may be performed using, without limitation, linear classifiers such as without limitation logistic regression and/or naïve Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary. A Naïve Bayes Classification Model is disclosed further with reference to FIG. 24.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors' algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors' algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

In an embodiment, and still referring to FIG. generating the proposed therapeutic oligomer may include employing a PNA Finder, which may include a toolbox that comprises two primary functions: a "Get Sequences" tool for finding an initial list of PNA candidates and/or a "Find Off-Targets" tool for determining incidental undesired alignments of those candidates, wherein a "Find Off-Targets" tool is described below. In an embodiment, and without limitation, PNA Finder may include oligomeric machine-learning model as described above. In another embodiment, and without limitation, each of these functions may contain several sub-functions to aid in the toolbox workflow, efficiency, and the in silico PNA screening process. These tools may be designed to function as a cohesive workflow, starting from a user-provided list of gene targets and providing a filtered set of stable and highly specific PNA candidates that represent the most viable therapeutic options. The generalized toolbox, as described herein may also include a graphical user interface to ensure that it is a streamlined process, as well as to avoid difficulties with the command line interface on which several of its constitutive programs operate. In an embodiment, "Get Sequences" may be used for identifying an initial list of PNA candidates and performing preliminary screening of these candidates. Additionally or alternatively, PNA Finder may generate proposed therapeutic oligomer to activate and/or inhibit expression of genes as a function of gene targets for the human genome. In another embodiment and without limitation, PNA Finder may generate proposed therapeutic oligomer to for one or more pathogens, viral agents, and the like thereof. In an embodiment, and without limitation, PNA Finder may generate proposed therapeutic oligomer sequence 108 as a function of a criteria for design of species specific PNAs, which may include without limitation: (i) Gene target is involved in radiation response, (ii) the TIR and IRES sequence is amenable to design of peptide PNAs with low melting temperature when targeting mRNA (expression inhibition), or the upstream promoter regions (−150, −116, −78, and −7 positions) when targeting DNA (transcriptional activation), and (iii) where possible off-target sites within the human transcriptome and between microbiome species are not present. Additionally or alternatively, criteria for design of species specific PNAs may include: (i) gene target is essential, (ii) evidence that gene silencing of target and/or inhibition of cognate protein is growth inhibitory, (iii) the TIR and RBS sequence is amenable to design of peptide PNAs with low melting temperature, (iv) where possible off-target sites within and between species are not present in TIR and RBS sites, (v) for targeting multiple strains homologues are present in a desired number of species, and (vi) the TIR of the mRNA has at least two base pair between species when designing unique PNAs.

Still referring to FIG. 1, outputting a sequence warning for proposed therapeutic oligomer sequence 108. As used in this disclosure a "sequence warning" is a notification and/or signal that identifies a solubility and/or self-complementation issue. In an embodiment, and without limitation, sequence warning may analyze proposed therapeutic oligomer sequence and denote possible solubility issues. For example, and without limitation, solubility issues may denote that a proposed therapeutic oligomer sequence has an uncommon common-ion effect, ionic strength element, solubility equilibrium, temperature, and the like thereof making it difficult to dissolve and/or suspend in a solvent. In another embodiment, and without limitation, sequence warning may analyze proposed therapeutic oligomer sequence and denote possible self-complementation issues. For example, and without limitation, self-complementation issues may denote that a proposed therapeutic oligomer sequence has more than six bases that may be self-complementary subsequences.

Still referring to FIG. 1, computing device 104 identifies a genomic locus 132 that the proposed therapeutic oligomer is predicted to bond to. As used in this disclosure a "genomic locus" is a fixed position on a chromosome, RNA chain, and/or DNA chain where a particular gene and/or genetic marker is located. For example, and without limitation, genomic locus 132 may denote that a particular gene and/or genetic marker is located on a p-arm of a chromosome. As a further non-limiting example, genomic locus 132 may denote that a particular gene and/or genetic marker is located on a q-arm of a chromosome. As used in this disclosure "bonding" is a process of forming a connection between two or more molecules, ions, and/or atoms that are non-associated. In an embodiment, and without limitation, bonding may include forming a connection as a function of an intermolecular force that causes two or more molecules to be attracted and/or repulsed by each other. For example and without limitation, bonding may include connecting two or more molecules, ions, and/or atoms as a function of a dipole-dipole interaction. As a further non-limiting example, bonding may include connecting two or more molecules, ions, and/or atoms as a function of a hydrogen bond. As a further non-limiting example, bonding may include connecting two or more molecules, ions, and/or atoms as a function of a London dispersion force. As a further non-limiting example, bonding may include connecting two or more molecules, ions, and/or atoms as a function of a cation-pi interaction. Computing device 104 identifies genomic locus 132 that the proposed therapeutic oligomer is predicted to bond to as a function of an off-target sequence function 136. As used in this disclosure an "off-target sequence function" is an algorithm and/or model that determines the number of inaccuracies and/or off-targets of a target sequence, wherein a "target sequence," as used herein, is a nucleotide sequence, such as a DNA sequence, or an mRNA sequence, that may be complementary to antisense molecules, and preferably an antisense peptide nucleic acid. In an embodiment, and without limitation, off-target sequence function 136 may include a function that reduces the expected number of off-targets in a genome, which is given by the following equation, under the simplifying assumption of total randomness of the genome:

$$E_{off-targets} = \frac{1}{4^N} \times (\text{genome size})$$

wherein $E_{off-targets}$, is the expected number of off-targets, genome size, is the number of base pairs in the genome, and N, is the length of proposed therapeutic oligomer sequence 108, such as but not limited to the length of a PNA.

Still referring to FIG. 1, genomic locus 132 is identified as a function of identifying an incidental alignment 140 as a function of proposed therapeutic oligomer sequence 108 and genomic library 112. As used in this disclosure an "incidental alignment" is an undesired alignment of proposed therapeutic oligomer sequence. For example, and without limitation, incidental alignment 140 may denote that an undesired alignment of a PNA may occur as a function of an extraneous hydrogen bond formation. As a further non-limiting example, incidental alignment 140 may denote that an undesired alignment of a PNA may occur as a function of a poor solubility and/or strong London dispersion forces.

Still referring to FIG. 1, genomic locus 132 is identified as a function of modeling incidental alignment 140 to a corresponding genome assembly location 144. As used in this disclosure a "genome assembly location" is a sequence composition of a portion of a genome that resides in a location of a chromosome. For example, and without limitation, a first sequence of a genome may reside in a p-arm of a chromosome, wherein incidental alignment 140 is modeled to the first sequence of the genome located in a p-arm of the chromosome. In an embodiment, and without limitation, modeling may include producing a 3D computer model and/or virtual representation of a proposed therapeutic oligomer sequence 108 and/or genome assembly location 144. For example, and without limitation, computing device generate a topographical and/or 3D rendering of proposed therapeutic oligomer sequence 108 and/or genome assembly location 144. In an embodiment, and without limitation, 3D rendering may include a solid model of proposed therapeutic oligomer sequence 108 and/or genome assembly location 144. As used in this disclosure a "solid model" is a computer model of three-dimensional solids. For example, and without limitation, solid model may include one or more geometric and/or solid models of proposed therapeutic oligomer sequence 108 and/or genome assembly location 144. In an embodiment, and without limitation solid model may include a solid representation scheme such as a primitive instancing, spatial occupancy enumeration, cell decomposition, boundary representation, surface mesh modeling, sweeping, constructive solid geometry, implicit representation, parametric and/or feature-based modeling, and the like thereof. In an embodiment, and without limitation, solid model may incorporate one or more voxels, polygonal meshes, parametric shapes, and the like thereof to represent proposed therapeutic oligomer sequence 108, and/or genome assembly location 144.

In an embodiment, and still referring to FIG. 1, modeling incidental alignment 140 to a corresponding genome assembly location 144 may include producing a seed length as a function of a length parameter associated to proposed therapeutic oligomer sequence 108. As used in this disclosure a "seed length" is the length of a proposed therapeutic oligomer sequence and/or PNA length. As used in this disclosure a "length parameter" is the total distance of each bond and/or oligomer that comprises proposed therapeutic oligomer sequence and/or PNA. For example, and without limitation, length parameter may be a total distance comprising angstroms, nanometers, micrometers, and the like thereof. In an embodiment, and without limitation, the default for proposed therapeutic oligomer sequence 108 and/or PNA length may be set to 12, based on competing factors. In another embodiment, and without limitation, increasing proposed therapeutic oligomer sequence and/or PNA length may reduce expression regulation as a function of an increased proposed therapeutic oligomer sequence and/or PNA length, wherein increasing proposed therapeutic oligomer sequence and/or PNA length may enhance binding strength and/or specificity. For example, and without limitation, a PNA length of 12 may yield sufficient inhibition and/or may yield less than one expected off-target for even the largest genomes. In one exemplary embodiment, a default 12-mer PNA may be designed to complement the base pattern ***AUG. This default positioning may be located close to the start codon and have the highest inhibitory effect in prokaryotes. The window may be expanded according to the user's requirements, to produce multiple candidate sequences of the given length. For instance, a window of (−6, −4) with a default 12-mer PNA would produce three PNA candidates, complementary to the following base patterns: **AUG*, ***AUG, AUG***, and the like.

In an embodiment, and without limitation, modeling incidental alignment 140 may include aligning proposed therapeutic oligomer sequence 108 to a corresponding genome assembly location 144 as a function of the seed length, wherein aligning may include orienting proposed therapeutic oligomer sequence 108 in a three-dimensional space as a function of a binding affinity of the proposed therapeutic oligomer sequence to the genome assembly location 144. Additionally or alternatively, modeling incidental alignment 140 may include modeling incidental alignment 140 as a function of the alignment and a user-specified number of allowed mismatches, wherein a "mismatch," as used herein is an improper base pair bonding of a nucleobase. For example, and without limitation a mismatch may include a guanine nucleobase bonding to a thymine nucleobase. As a further non-limiting example a mismatch may include an adenine nucleobase bonding to a cytosine nucleobase. In an embodiment, and without limitation, mismatch may be a function of a nucleobase tautomerizing. In another embodiment, and without limitation, wherein modeling may include producing a 3D computer model and/or virtual representation as described above. For example, and without limitation, modeling may include producing a 3D computer model of an alignment and a user-specific number of allowed mismatches. In an embodiment, and without limitation, the default number of allowed mismatches may be set to zero.

Still referring to FIG. 1, identifying the genomic locus 132 includes identifying genomic locus 132 as a function of incidental alignment 140 model and an overlap element 148. As used in this disclosure an "overlap element" is an element of data that denotes a proposed therapeutic oligomer sequence overlaps with any genomic features of genomic library 112. For example, and without limitation, overlap element 148 may denote those one or more sequences of proposed therapeutic oligomer sequence overlaps with a plurality of genomic features of genomic library 112. In an embodiment, and without limitation, overlap element 148 may include a BAM file that may be used as an input for a BEDTools "window" function, wherein the BEDTools "window" function may be used to identify whether a particular PNA-genome alignment in the BAM file overlaps with any genomic features, as identified by an input GFF genome annotation file. In another embodiment, "Find Off-Targets" tool may then examine the BED file output of the "window" function to determine which proposed therapeutic oligomer sequences and/or PNAs are expected to have off-target alignments in coding sequences, as well as which of these coding sequence alignments occur near to the start codon as described below. The gene coordinate inputs may be used to define the region around the start codon where inhibition is expected. The default for "Find Off-Targets" tool may be set to (−20, 20). In an embodiment, and without limitation, "Find Off-Targets" tool may be used to search for incidental alignments between a model and/or list of PNA target sequences and a genome assembly. In an embodiment, and without limitation, "Find Off-Targets" tool may take an input from a PNA target sequences, a genome assembly, and/or a corresponding genome annotation file. In another embodiment, "Find Off-Targets" tool may incorporate the following parameters: the number of allowed alignment mismatches, PNA sequence length, and/or a pair of gene coordinates relative to the +1 translation start site. In an embodiment, "Find Off-Targets" tool may provide an output comprising the total off-target counts for each proposed therapeutic oligomer sequence and/or PNA.

In an embodiment, and still referring to FIG. 1, identifying genomic locus 132 further comprises outputting a first file representing a potentially inhibitory alignment of proposed therapeutic oligomer sequence 108. As used in this disclosure "potentially" is a probabilistic outcome that is expressed on [0,1], wherein exceeding a threshold denotes a likelihood of the outcome occurring. In an embodiment, probability may be defined according to a characteristic function, which may include, without limitation, a step function having output values on a probability interval such as [0,1] or the like; step function may have an output representing 100% or probability of 1 for values falling in a range and zero or a representation of zero probability for values not in the range. For example, and without limitation, the "Find Off-Targets" tool may produce as an output a BED file of all potentially inhibitory PNA alignments, wherein a BED file may be written with the features corresponding to each ID, and "Get Sequences" prints output to indicate the matches. As a further non-limiting example, "Find Off Targets" tool may edit the coordinates of a BED file according to the PNA sequence length and/or the gene coordinates parameters. In an embodiment, and without limitation, "Find Off-Targets" tool may include an off-target counts option, wherein the option totals the number of potentially inhibitory off-targets for each PNA and may provide those sums in a separate file. Off-target predictions may be used as another means of screening PNA candidates, either to avoid targeting other genes within a target genome or to avoid targeting another organism altogether. This function is especially valuable in PNA antibiotic design, as it allows for the design of highly specific antisense PNAs that may avoid broad antibiotic action against a microbiome environment.

In an embodiment, and still referring to FIG. 1, identifying genomic locus 132 further comprises outputting a second file identifying a potentially off-target alignment of proposed therapeutic oligomer sequence 108. For example, and without limitation, the coordinates and/or strand designation of each gene target in the original BED file may be used to create a new BED file wherein each set of genomic coordinates corresponds to the locus that each respective proposed therapeutic oligomer sequence and/or PNA may target. The BEDTools function "getfasta" may then be used to produce a FASTA file of the PNA target sequences from these BED file coordinates and the input genome assembly FASTA file. An output file with the PNA sequences-reverse complements of the target sequences—may also be produced. If the options for sequence warnings and STRING database analysis are selected, these elements may be included in the output file as well. The STRING database analysis may provide a network of experimentally verified, computationally predicted, and inferred protein interactions for each gene target, as well as the number of total connections between the genes of this network.

Still referring to FIG. 1, proposed therapeutic oligomer sequence 108 is selected as a function of sequence identification function 120, genomic locus 132, and a criterion element 152, wherein criterion element 152 is described below and may include a regulation modification, solubility element, stability element, presence of a self-complementary subsequence, presence of an off-target alignment sequence, start codon proximal element of a gene target, and the like thereof. In an embodiment and without limitation, proposed therapeutic oligomer sequence and/or PNA may be selected for synthesis according to application-specific needs for sequence stability and specificity. In an embodiment, and without limitation, application-specific needs may be ascertained from the output of the PNA Finder toolbox.

In an embodiment, and still referring to FIG. 1, proposed therapeutic oligomer sequence 108 may be selected as a function of treating an acute radiation syndrome (ARS) and/or radiation toxicity to inhibit and/or activate expression of radiation responsive gene. For example, and without limitation ARS and/or radiation toxicity is an acute illness caused by radiation of part of or whole body by a high dose (>1Gray or Gy) of radiation for a short period of time, wherein a therapeutic oligomer sequence to treat radiation related pathologies may be selected. In this embodiment, rationally designed PNAs that may inhibit and/or activate expression of radiation-responsive genes, such as Granulocyte colony-stimulating factor (G-CSF), 2) granulocyte-macrophage-colony30 stimulating factor (GM-CSF), 3) erythropoietin (EPO), and 4) gamma globulin (GG), may allow prevention or reduction of radiation-induced conditions, such as Acute Radiation Syndrome (ARS). In this embodiment, at least two types of therapeutic oligomer sequences and/or PNAs may be selected, specifically, inhibitors and activators, wherein inhibitors may be without limitation single stranded antisense PNAs designed to bond to mRNAs of targeted gene to block translation. Activators may be without limitation, antigene PNAs designed to bond to genomic DNA in the upstream promoter regions of targeted genes to increase gene expression.

In an embodiment, and still referring to FIG. 1, a PNA finder may be utilized to design a catalog of unique PNA inhibitor and/or activator molecules against radiation-responsive genes and reduce chances of off-target effects by comparison to gut microbiome and human transcriptome.

In another embodiment, and still referring to FIG. 1, computing device 104 may design a PNA molecule for activation/inhibition of genes involved in radiation response. For example, and without limitation, computing device may design of approximately three to five 20-mer PNA molecules that target the translational start site (TIS) and/or internal ribosome entry site (IRES) of the mRNA encoded by G-CSF, GM-CSF, EPO and GG genes, with the target sequence in the middle of the oligomer, with 3-5 nucleotides flanking the target region. In this embodiment, a cell penetrating peptide (CPP) and/or quantum dot (QD) at the N terminus of the target PNA may be attached to the PNA for increased cellular entry. Additionally or alternatively a highly positively charged protein transduction domain of transactivator of transcription (TAT) sequence (YGRJJRRQRRR) (SEQ ID NO. 3) from HIV-1 may be incorporated to successfully facilitate PNA delivery into mammalian cells and nucleus via an energy- and receptor-independent mechanism called micropinocytosis.

In another embodiment, and still referring to FIG. 1, computing device 104 may design a PNA activators as a function of a modular approach, which may comprise: 1) a sequence-specific DNA binding domain (DBD) to direct the PNA to the appropriate promoter, and 2) an amino acid sequence motif that may act as an activation domain (AD) to recruit transcription complexes to the gene target promoter region, wherein a modular approach is described below in reference to FIG. 8. For example, and without limitation, such PNA driven activation may generate a nearly 8-fold activation of expression of gamma-globin gene using a chimeric VP2 minimal ADPNA-TAT in mouse bone marrow cells and human primary peripheral blood cells compared to basal expression. VP2 minimal AD is a highly acidic 16 amino acid sequence (MLGDFDLDMLGDFDLD) (SEQ ID NO. 2) derived from the herpes simplex virus C terminus transactivation domain of VP16. This artificial AD has been shown to be highly effective in vitro when linked to DNA-binding domains. In another embodiment a chimeric PNA sequence to bond to the promoter for the of G-CSF, GM-CSF, EPO and GG genes may be selected by designing 15 mer PNA centered at −150, −116, −78, and −7 positions relative to the transcriptional start sites of the gene. In order to facilitate binding to DNA, a Lysine residue may be attached to 3' to give the PNA molecule the positive change to enhance strand invasion. For activating gene expression during PNA synthesis the inventors may further design chimeric PNA-VP2 binding domain-binding peptide chimera capable of activating transcription. Finally, for enhancing intracellular delivery, the present inventors may attach a CPP based on the TAT sequence or quantum dots as described below.

In another embodiment, and still referring to FIG. 1, computing device 104 may design a design of PNAs for species-centered strategy. For example, and without limitation, PNA molecules may be designed to prevent translation of one or more essential genes within a pathogenic organism. As a further non-limiting example, and without limitation, PNA molecules may be designed to prevent translation of one or more essential genes within a pathogenic organism, such as SARS-CoV2, HIV, influenza, and the like thereof. In this embodiment, computing device may design a 12-mer PNA molecule that targets the translational start site (TIS) or ribosome binding site (RBS) of the mRNA encoded by an essential gene. Such 12-mer long PNAs may be designed against genes in pathogens using a stepwise targeting method, such that antisense oligomers are designed with the target sequence in the middle of the oligomer, with 3-5 nucleotides flanking the target region.

In another embodiment, and still referring to FIG. 1, computing device 104 may design 12-mer PNAs oligomers, such as but not limited to α-RBS and α-STC against the ribosome binding site (RBS) and/or start codon (STC) of TEM-1 β-lactamase (bla) mRNA to prevent the ribosomal binding and ribosomal migration respectively, both causing inhibition of translation of bla transcript to prevent the production of active β-lactamase enzyme. The 12-mers may be conjugated, to positively charged (KFF)3K cell penetrating peptide (CPP). In an embodiment, and without limitation, both α-RBS and α-STC may exhibit no off-target activity. In another embodiment, and without limitation, computing device 104 may design PNA molecules that target six essential genes including, but not limited to, folC involved in metabolism, ffh which is involved in cell signaling, lexA, a key regulator of stress response, and fnrS, a small Hfq binding RNA, rpsD involved in protein biosynthesis, and gyrB involved in DNA replication.

Still referring to FIG. 1, computing device 104 synthesizes a therapeutic oligomer 156 as a function of proposed therapeutic oligomer sequence 108. As used in this disclosure a "therapeutic oligomer" is a polymer comprising at least a repeating unit that produces a therapeutic effect as a function of regulating an expression of one or more genes and/or polynucleotides. In an embodiment, therapeutic oligomer 156 may include a nano-oligomer. As used in this disclosure a "nano-oligomer" is a therapeutic oligomer that comprises a size in the range of 0.1 nm to 100 nanometers. As used in this disclosure "synthesizing" is initiating a manufacturing process and/or automated synthesis process that builds one or more therapeutic oligomers. In some embodiments, a manufacturing process is a process used to form a product, which may be an end-product, or a part used to assemble an end-product, by the performance of one or more manufacturing steps. One or more steps in the manufacturing process may include physical modifications to a product and/or programming and modeling steps used to perform the modifications, such as modeling the product, or computing toolpaths and/or other algorithms for the product's manufacture.

In an embodiment, and still referring to FIG. 1, synthesizing therapeutic oligomer 156 may include an additive manufacturing device. An "additive manufacturing device," as used in this disclosure, is a device that performs additive manufacturing processes. As used in this disclosure, an "additive manufacturing process" is a process in which material is added incrementally to a body of material in a series of two or more successive steps. A material may be added in the form of a stack of incremental layers; each layer may represent a cross-section of an object to be formed upon completion of an additive manufacturing process. Each cross-section may, as a non-limiting example be modeled on a computing device as a cross-section of graphical representation of the object to be formed; for instance, a computer aided design (CAD) tool may be used to receive or generate a three-dimensional model of an object to be formed, and a computerized process, such as a "slicer" or similar process, may derive from that model a series of cross-sectional layers that, when deposited during an additive manufacturing process, together will form the object. Steps performed by an additive manufacturing system to deposit each layer may be guided by a computer aided manufacturing (CAM) tool. Persons skilled in the art will be aware of many alternative tools and/or modeling processes that may be used to prepare a therapeutic oligomer, including without limitation the peptide synthesis, synthetic reactions, and the like thereof.

In an embodiment, and still referring to FIG. 1, therapeutic oligomers 156 may comprise PNAs, wherein PNAs are described above. In an embodiment, and without limitation, PNAs may inhibit gene expression in a target host, wherein a "target host," as used herein, is an organism and/or entity that the PNA is interacting with. In an embodiment, and without limitation an organism and/or entity may include a pathogen, viral agent, and the like thereof. In another embodiment, and without limitation, PNAs may upregulate gene expression in a target host. Additionally or alternatively, computing device 104 may synthesize therapeutic oligomer 156 and/or PNA using a solid-state PNA synthesis comprising a Fluorenylmethyloxycarbonyl chemistry. As used in this disclosure a "solid-state PNA synthesis" is a synthetic reaction that utilizes one or more solid supports for physical stability to build an oligomer. For example, and without limitation, solid supports may include a resin. Resin may include any resin that comprises physical stability and/or permits the rapid filtration of liquids. In an embodiment and without limitation, resin may include one or more gel-type support resins, surface-type support resins, and/or composite resins. In another embodiment, and without limitation, resin may be able to withstand repeated use of trifluoroacetic acid (TFA). In another embodiment, resin may include one or more resins as a function of a desired product such as, but not limited to a C-terminal carboxylic acid and/or an amide. In an embodiment and without limitation, resin may include a Wang resin. Additionally or alternatively, therapeutic oligomer 156 and/or PNA may be synthesized as a function of a Tert-butyloxycarbonyl chemistry. Therapeutic oligomers, PNAs and/or other polynucleotides may be chemically derivatized by methods known to those skilled in the art. For example, PNAs may have amino and carboxy groups at the 5' and 3' ends, respectively, that can be further derivatized.

Still referring to FIG. 1, synthesizing therapeutic oligomer 156 may include coupling proposed therapeutic oligomer sequence 108 to a nanostructure. As used in this disclosure a "nanostructure" is a structure of intermediate size between microscopic and molecular structures. For example, and without limitation, nanostructure may include a structure that comprises a size in the range of 0.1 nm to 100 nanometers. In an embodiment, and without limitation, nanostructures may include spherical nanoparticles. As used in this disclosure a "nanoparticle" is a three-dimensional object existing on a nanoscale, wherein the particle is between 0.1 nm and 100 nm in each spatial dimension. For example, and without limitation, nanoparticle may include a spherical nanoparticle with a diameter of 23 nm. In an embodiment, and without limitation, nanoparticle may include a transition metal nanoparticle. As used in this disclosure a "transition metal nanoparticle" is a nanoparticle composed of a transition metal. For example, and without limitation, transition metal nanoparticle may include a gold nanoparticle. As a further non-limiting example, transition metal nanoparticle may include a copper nanoparticle. As a further non-limiting example, transition metal nanoparticle may include a zinc nanoparticle. In an embodiment, and without limitation, transition metal nanoparticle may include one or more transition metals comprising groups 3-12 transition metals on the period table of elements. In an embodiment, and without limitation, coupling proposed therapeutic oligomer sequence 108 to nanostructure may be a function of a covalent bond. As used in this disclosure a "covalent bond" is a chemical bond that involves sharing of electrons between atoms. For example, and without limitation, covalent bond may include electron pairs that are shared and/or bonded as a function of a stable balance of attractive and/or repulsive forces between atoms. In an embodiment, and without limitation, covalent bond may allow molecules and/or atoms to fill one or more valence shells of an atom to produce a stable electronic configuration. In another embodiment, covalent bond may include one or more interactions such as, but not limited to σ-bonding, π-bonding, metal-to-metal bonding, agnostic interactions, bent bonds, three-center two-electron bonds, three-center four-electron bonds, and the like thereof.

In an embodiment and still referring to FIG. 1, coupling proposed therapeutic oligomer sequence 108 to a nanostructure may include utilizing a chemical synthesis. As used in this disclosure a "chemical synthesis" is a physical process of mixing reagents and/or solvents to produce a product. For example, and without limitation, chemical synthesis may include mixing one or more nanostructures, proposed therapeutic oligomer sequences, and/or solvents to produce therapeutic oligomer. As used in this disclosure a "reagent" is a substance and/or mixture used to aid a chemical reaction. For example, and without limitation, reagent may include a chemical, reactant, and the like thereof. In an embodiment, reagent is placed in a receptacle to be confined to the chemical synthesis. As used in this disclosure a "receptacle" is an object and/or space that is used to confine a plurality of reagents. For example, and without limitation, receptacle may include one or more beakers, flasks, bottles, jars, test tubes, desiccators, glass evaporating dishes, watch glasses, petri-dishes, slides, graduated cylinders, volumetric flasks, burettes, ebulliometers, condensers, retorts, drying pistols, and the like thereof. In an embodiment, and without limitation, receptacle may be placed in a modulation component. As used in this disclosure a "modulation component" is a structure and/or object that regulates one or more external properties to receptacle. For example, and without limitation, modulation component may regulate one or more temperatures as a function of a water bath, oil bath, sand bath, ice bath, hot plate, Bunsen burner, flame, meeker burner, and the like thereof. As a further non-limiting example, modulation component may regulate one or more pressures as a function of a vacuum system, compressor, and the like thereof. As a further non-limiting example, modulation component may regulate one or more wavelengths as a function of a polarization and/or slit system. In an embodiment, and without limitation, modulation component may include a stirring apparatus. As used in this disclosure a "stirring apparatus" is a device that employs a rotating magnetic field beneath receptacle. In an embodiment, and without limitation, stirring apparatus may be incorporated in one or more modulation components. For example, and without limitation, a magnetic stir bar may be placed inside of receptacle, wherein stirring apparatus may rotate a magnetic field beneath receptacle such that the magnetic stir bar immersed in the reagents is forced to spin and/or rotate at a given angular velocity, such as but not limited to revolutions per minute. In an embodiment, and without limitation, magnetic stir bar may include a bar-shaped octagonal and/or circular rod.

Still referring to FIG. 1, reagent may be added into receptacle as a function of a transfer device. As used in this disclosure a "transfer device" is a device and/or tool that transports a volume of liquid. In an embodiment, and without limitation, transfer device may include one or more media dispensers. In another embodiment, and without limitation, transfer device may include a pipette. As used in this disclosure a "pipette" is a device and/or tool that creates a vacuum displacement to draw up a liquid, wherein releasing the vacuum dispenses the liquid. For example, and without limitation, pipette may include one or more air displacement micropipettes, electronic pipettes, positive displacement pipettes, volumetric pipettes, graduate pipettes, Pasteur pipettes, transfer pipettes, pipetting syringes, Van Slyke pipettes, Ostwald-Folin pipettes, glass micropipettes, microfluidic pipettes, low volume pipettes, and the like thereof. In an embodiment, and without limitation, pipette may create the vacuum displacement above receptacle, wherein a pipette tip is located within reagent and/or solvent located within receptacle. As used in this disclosure a "pipette tip" is a tapered cylindrical tube that has a first aperture comprising a first diameter and a second aperture comprising a second diameter, wherein the second diameter is greater than the first diameter. In an embodiment, and without limitation, first aperture may be configured to draw a reagent, liquid, and/or solvent. In another embodiment, and without limitation, second aperture may be configured to be secured to pipette and/or transfer device. Additionally or alternatively, transfer device may incorporate one or more valves, microfluidic channels, stopcocks, and the like thereof to control the transfer of one or more reagents, liquids, and/or solvents.

In an embodiment, and still referring to FIG. 1, synthesizing therapeutic oligomer 156 may include an automated synthesizer 160. As used in this disclosure an "automated synthesizer" is a device and/or apparatus that automatedly performs one or more synthetic process. In an embodiment, and without limitation, automated synthesizer 160 may include computing device 104. In another embodiment, and without limitation, automated synthesizer 160 may include a remote device, pipettor, robotic device, and the like thereof. In an embodiment, and without limitation, automated synthesizer 160 may perform one or synthetic processes such as, but not limited to a chemical synthesis, peptide synthesis, coupling processes, and the like thereof. For example, and without limitation, automated synthesizer 160 may include an Apex 396 peptide synthesizer (AAPPTec, LLC, Louisville, Ky., U.S.A). In an embodiment, and without limitation, automated synthesizer 160 may be used to perform solid-state PNA synthesis using Fmoc chemistry on MBHA rink amide resin at a 30 μmol scale, wherein Fmoc-PNA monomers may be include A, C, and G monomers that are protected at amines with Bhoc groups. In another embodiment, and without limitation, automated synthesizer 160 may synthesize therapeutic oligomer 156 with a cell-penetrating peptide, such as (KFF)3K, which may have lysine residues protected with Boc groups. In another embodiment, and without limitation, automated synthesizer 160 may be used to perform solid-phase Fmoc chemistry at a 10 μmol scale on MBHA rink amide resin, wherein Fmoc-PNA monomers may include A, C, and G monomers protected at amines with Bhoc groups. In another embodiment, and without limitation, automated synthesizer 160 may synthesize therapeutic oligomer 156 with a N-terminal cell-penetrating peptide (KFF) K., which may have lysine residues protected with Boc groups. In another embodiment, automated synthesizer 160 may incorporate one or more modes of operation, such as but not limited to a semi-automated mode and/or a fully automated mode to synthesize therapeutic oligomer 156 and/or PNA. For example, and without limitation, semi-automated mode may allow a user to input one or more reagents, wherein automated synthesizer 160 automatically mixes and/or modulates the chemical synthesis. As a further non-limiting example, fully automated mode may allow a user to select a therapeutic oligomer and/or PNA from a graphical user interface, on a display, wherein automated synthesizer 160 measures the reagents, transfers the reagents to receptacle, and performs the chemical synthesis without user intervention.

Still referring to FIG. 1, synthesizing therapeutic oligomer 156 may include synthesizing a therapeutically effective amount. As used in this disclosure a "therapeutically effective amount" is an amount of a therapeutic oligomer that will relieve to some extent one or more of the symptoms of the ailment, infection, and/or disorder being treated. In an embodiment, and without limitation, a therapeutically effective amount may include an amount of therapeutic oligomer that has the effect of (1) reducing the pathogen, (2) inhibiting (that is, slowing to some extent, preferably stopping) pathogen and/or viral agent growth, (3) inhibiting to some extent (that is, slowing to some extent, preferably stopping) pathogenicity, and/or (4) relieving to some extent (or, preferably, eliminating) one or more signs or symptoms associated with the pathogen and/or viral agent. In another embodiment, and without limitation, treatment of a viral agent, and in particular SARS-CoV2, a therapeutically effective amount may include an amount of therapeutic oligomer that has the effect of (1) reducing the viral agent magnitude, (2) inhibiting (that is, slowing to some extent, preferably stopping) viral growth, (3) inhibiting to some extent (that is, slowing to some extent, preferably stopping) viral pathogenicity, and/or (4) relieving to some extent (or, preferably, eliminating) one or more signs or symptoms associated with the viral agent. In another embodiment, therapeutically effective amount may include an amount of therapeutic oligomer that treats one or more ailments, infections, diseases and/or disorders. As used in this disclosure "treating" is a process of reversing, alleviating, inhibiting the progress of, or preventing the disorder or condition to which such term applies, or one or more symptoms of such disorder or condition. For example, and without limitation, treating the viral agent associated with influenza may include alleviating one or more symptoms and/or proliferations of the viral agent present in an organism.

Still referring to FIG. 1, synthesizing therapeutic oligomer 156 may further comprise clarifying therapeutic oligomer 156. As used in this disclosure "clarifying" is a process of purification and/or separation that extracts one or more distinct therapeutic oligomers from the chemical synthesis. For example, and without limitation, clarifying may include purifying a therapeutic oligomer from a chemical synthesis such that only one therapeutic oligomer remains. In an embodiment, and without limitation, clarifying the therapeutic filter may be a function of a filter. As used in this disclosure a "filter" is a physical and/or chemical medium that removes and/or extracts one or more therapeutic oligomers of interest. In an embodiment, and without limitation, filter may include a size exclusion filter. As used in this disclosure a "size exclusion filter" is a filter comprising a plurality of apertures comprising a diameter that allows substances and/or liquid to flow across the filter that may traverse through the diameter. In an embodiment, and without limitation, size exclusion filter may be uniform and/or non-uniform. For example, and without limitation, size exclusion filter may be comprised of a plurality of 50 μm apertures. As a further non-limiting example, size exclusion filter may be comprised of a plurality of apertures ranging from 5-500 μm. In another embodiment, and without limitation, filter may include an electromagnetic filter. As used in this disclosure an "electromagnetic filter" is a filter that attracts one or more metallic particles and/or structures to a substance to remove the metallic particles and/or structures from a chemical synthesis. For example, and without limitation, electromagnetic filter may comprise one or more magnets that attract a nanostructure and/or nanoparticle to a magnet to remove the nanostructure and/or nanoparticle from a chemical synthesis.

In an embodiment, and still referring to FIG. 1, therapeutic oligomer 156 and/or PNA may be purified as a function of a liquid chromatography component. In an embodiment, and without limitation, "liquid chromatography component" is a component capable of separating therapeutic oligomers from a chemical synthesis. In an embodiment, and without limitation, liquid chromatography component may include a component that separates analytes as a function of a stationary phase and a mobile phase. For example, and without limitation, a stationary phase may include a phase comprising a porous solid such as but not limited to glass, silica, alumina, free silanol, bonded silanol, geminol silanol, siloxane, and the like thereof. As a further non-limiting example, a mobile phase may include a phase comprising a liquid solvent such as but not limited to water, acetonitrile, chloroform, isopropyl alcohol, ethanol, hexane, butane, propane, benzene, and the like thereof. In an embodiment and without limitation, physical separation component may separate analytes and/or biological samples as a function of a capacity factor, k'. As used in this disclosure a "capacity factor" is a measurable value representing the strength of the interaction of the analyte and/or biological sample with the stationary phase as it flows through the mobile phase, wherein the capacity factor is determined by:

$$k' = \frac{t_r - t_m}{t_m}$$

where $t_r$, is the retention time of the analyte and $t_m$, is the retention time of a reference compound, wherein a "reference compound," as used herein, is a compound that has a known retention time and/or does not interact with the stationary phase. As used in this disclosure a "retention time" is a time period that it takes for a compound to travel through liquid chromatography component, wherein a time period includes a distance of time expired such as seconds, minutes, hours, days, and the like thereof. In an embodiment, and without limitation, physical separation component may separate analytes and/or biological samples as a function of a selectivity factor, $\alpha$. As used in this disclosure a "selectivity factor" is a measurable value associated with the amount of separation between two or more therapeutic oligomers, wherein selectivity factor is determined by:

$$\alpha = \frac{k_2'}{k_1'} = \frac{t_{r_2} - t_m}{t_{r_1} - t_m}$$

where, $t_{r_1}$ is the retention time of a first therapeutic oligomer, $t_{r_2}$, is the retention time of a second therapeutic oligomer, $k'_1$, is the capacity factor of the first therapeutic oligomer, and $k'_2$, is the capacity factor of the second therapeutic oligomer. For example, and without limitation, the selectivity factor for liquid chromatography component may be 2.15 for the amount of separation between a first trifluoroacetic acid salt PNA and second trifluoroacetic acid salt PNA dissolved in an acetonitrile mobile phase and interacting with a C18 stationary phase.

In an embodiment, and still referring to FIG. 1, synthesizing therapeutic oligomer 156 may include precipitating a therapeutic oligomer. As used in this disclosure "precipitating" is a chemical process of transforming a dissolved substance into an insoluble solid. In an embodiment, and without limitation, precipitating therapeutic oligomer may include transforming a dissolved therapeutic oligomer in a solvent into an insoluble solid as a function of supersaturating a solvent. As a non-limiting example, precipitating therapeutic oligomer may be performed as a function of diethyl ether. Additionally or alternatively, synthesizing therapeutic oligomer may include drying a therapeutic oligomer. As used in this disclosure "drying" is a process of removing solvent and/or liquid from a solid. For example, and without limitation, drying may be performing over a time period, such as four or less days to achieve a higher purity of therapeutic oligomer, such as but not limited to a 90% purity. In an embodiment, automated synthesizer 160 may synthesize PNA products as a function of precipitating and/or purifying products using trifluoroacetic acid salts.

In an embodiment, and still referring to FIG. 1, synthesized therapeutic oligomers 156 may be purified and further tested in an in vitro and/or in vivo environment for specific activity. For example, and without limitation, therapeutic oligomer may be evaluated as a function of an up- and/or down-regulation of the expression of one or more gene targets. As a further non-limiting example, therapeutic oligomer may be evaluated as a function of potentiating known therapeutic compounds, such as but not limited to potentiating activity of traditional small-molecule antibiotics.

In an embodiment, and still referring to FIG. 1, automated synthesizer 160 may include an automated parallel high throughput in-lab synthesis capable of producing a plurality of therapeutic oligomers and/or PNAs per run in a short period of time, such as less than a day. In this embodiment, therapeutic oligomers may be synthesized using standard solid phase manual or automated peptide synthesis, using either tert-butyloxycarbonyl (tBoc) and/or 9-fluorenyl-methoxycarbonyl (Fmoc) protected PNA monomers. For example, and without limitation, for PNA-CPP sequence of N terminal-KFFKFFKFFK-AEEA(linker)-10 CACCGGCAAGTG-C terminal (SEQ ID NO. 1), firstly, the CPP peptide portion (KFF)3K of the PNA-CPP conjugate may be synthesized on the peptide synthesizer using normal automatic mode using a Fmoc-D-Lys (Boc) Wang resin (110 mg, 0.51 mmol/g). This may be followed by therapeutic oligomer synthesis using Fmoc protected PNA monomers with exocyclic amino acid groups of A, T, G and C using a single-shot delivery feature.

The synthesis of PNA may be started on Fmoc-D-Lys (Boc)-Wang resin (50 mg, 0.78 mmol/g). The Fmoc protecting group may be removed by using 20% piperidine in dimethylformamide (DMF) twice for 5 min each. This may be followed by download of resin by partial coupling to free amino acid groups. The unreacted free amino acids may be capped by adding PNA-capping solution (2 ml, for 5 min) containing 5% DIEA. The resin may further be washed and dried. The downloading may be measured in a UV Spectrophotometer at 290 nm. The downloaded resin may be kept in the automated synthesizer, and the coupling (0.5 ml of each PNA monomer, 0.3 ml HATU, and 0.3 ml 196.3 mM DIEA), washing (with DMF, MeOH, and DCM), deprotection, and washing steps may be repeated automatically in a continuous way until and exemplary 12-mer PNA product is obtained—although, as noted elsewhere different sized PNAs may be obtained. The final products of PNA-CPP may be purified with semi-preparative HPLC using C-18 column as described above and characterized using NMR and/or a mass analyzer component. As used in this disclosure a "mass analyzer component" is a component capable of analyze a mass to charge ratio and/or ion of a therapeutic oligomer and/or PNA. In an embodiment, and without limitation, mass analyzer component may include a linear quadrupole. As used in this disclosure a "linear quadrupole" is a mass analyzer that filters ions as a function of four metal rods that create a quadrupolar electric field. The quadrupolar electric field may allow ions of specific mass to charge ratios to be guided along the central axis of the four parallel arranged rods, while eliminating other mass to charge ratios. In an embodiment, and without limitation, the four metal rods may be hyperbolic which may match the electric field that is produced. In an embodiment, and without limitation, the quadrupolar electric field may be generated by the four rods through a series of tunable RF and DC voltages. In an embodiment, and without limitation, linear quadrupole may allow for specific mass to charge ratios to be selected and/or a range of mass to charge ratios to be selected to allow for either an entire mass window to be collected and/or peak hopping, wherein "peak hopping," is the analysis of a specific peak and/or mass to charge ratio to be identified. In another embodiment, and without limitation, mass analyzer component may include a time-of-flight mass analyzer. As used in this disclosure a "time-of-flight mass analyzer" is a mass analyzer that separates ions over time across a field-free drift space. As used in this disclosure a "field-free drift space" is an enclosed space wherein a limited and/or no electric field interacts with the ions present in the enclosed space. In an embodiment, and without limitation, ions may be focused into an ion packet. As used in this disclosure an "ion packet" is a group and/or cluster of ions. Ion packet may be pulsed into the field-free drift space with a uniform amount of kinetic energy. The uniform kinetic energy provided to the ion packet may allow the smaller ions to have higher kinetic velocities compared to the larger ions, wherein the smaller ions will reach the detector faster, due to the higher velocity, while the larger ions will reach the detector slower, due to the lower velocity. In an embodiment, and without limitation, mass analyzer component may include a tandem mass spectrometer component. As used in this disclosure a "tandem mass spectrometer component" is a component capable of elucidating structural data of an ion and/or mass to charge ratio. For example, and without limitation, tandem mass spectrometer component may fragment one or more ions of interest to produce a fragmented charged ion and a neutral loss. As used in this disclosure a "fragmented charged ion" is an ion that lacks at least an atom of the parent ion, wherein a parent ion is the first ion present in the mass analyzer component. For example, and without limitation, fragmented charged ion may include a daughter ion and/or ion having a direct relationship to the parent ion. As used in this disclosure a "neutral loss" is a neutral analyte and/or atom that is expelled from the parent ion. In an embodiment, and without limitation, tandem mass spectrometer component may elucidate structural data as a function of an ion activation method such as but not limited to collision-induced dissociated, surface induced dissociation, electron transfer dissociation, in-source decay, post-source decay, photodissociation, and the like thereof.

Still referring to FIG. 1, synthesizing the therapeutic oligomer 156 further comprises analyzing the therapeutic oligomer as a function of a validation protocol. As used in this disclosure a "validation protocol" is a protocol and/or method that identifies an efficacy and/or toxicity of the therapeutic oligomer. In an embodiment, and without limitation, validation protocol may include utilizing normalized growth data to determine the most effective PNA, as well as to improve the efficacy predictions of the PNA Finder toolbox. For example, and without limitation, a moderate correlation between a STRING database protein network node degree—a measure of the connectivity of a given gene within viral agent metabolism- and normalized 16-hour growth data of viral agents, may be utilized to identify an efficacy prediction. In an embodiment, and without limitation, validation protocol may measure inhibition of each PNA against that of a scrambled nonsense sequence. In an embodiment, and without limitation, validation protocol may incorporate one or more in vitro, in vivo, and/or macrophage based host-infection models to identify one or more efficacies and/or toxicities of therapeutic oligomer. In an embodiment, and without limitation, validation protocol may include one or more PNA interaction assays. For example, and without limitation, PNA interaction assays may include three colonies picked from a plate and used to inoculate three separate overnight cultures in 1 mL CAMHB each. After 16 hours, the culture may be diluted 1:10,000 in a 384-well microplate using three biological replicates per condition. The total culture volume for each 15 treatments may be 50 µL. PNA may be stored at −20° C. dissolved in 5% v/v DMSO in water. Growth in the plate may be monitored at an absorbance of 590 nm every 20 minutes for 24 hours, with shaking between measurements. In another embodiment and without limitation, PNA interaction may include clinical isolates that may be obtained and grown in Cation Adjusted Mueller Hinton broth (CAMHB) at 37° C. with 225 rpm shaking or on solid CAMHB with 1.5% agar at 37° C. Clinical isolates may be maintained as freezer stocks in 90% CAMHB, 10% glycerol at −80° C. Freezer stocks may be streaked out onto solid CAMHB and incubated for 16 hours to produce single colonies prior to experiments. For each biological replicate, a single colony may be picked from solid media and grown for 16 hours in liquid CAMHB prior to experiments. At the start of experiment, each culture may be diluted 1:10,000 in fresh CAMHB and added to either a control experiment without PNA or a 10 µM PNA condition. PNA samples may be stored in 5% DMSO to aid in stability. Interaction effects may be evaluated for significance using a two-way ANOVA test, and S values may be calculated with respect for the expected growth inhibition as calculated by a Bliss Independence model. The S-value for a given timepoint was calculated as follows:

$$S = \left(\frac{OD_{AB}}{OD_0}\right)\left(\frac{OD_{PNA}}{OD_0}\right) - \left(\frac{OD_{AB,PNA}}{OD_0}\right)$$

In an embodiment, and without limitation, for a given timepoint, the variable $OD_{AB}$ represents optical density with only carbapenem treatment, $OD_0$ represents the optical density without treatment, $OD_{PNA}$ represents optical density with only antisense-PNA treatment, and $OD_{AB,PNA}$ represents the optical density with a combination treatment. Plus/minus for S-values may be calculated by propagating standard error values for each term. In an embodiment, and without limitation, interaction effects may be represented as heatmaps and/or dendrograms. Additionally or alternatively, a Euclidean distance metric, optimal leaf ordering, and/or average linkage function may be used to identify interaction effects.

Still referring to FIG. 1, validation protocol may include testing therapeutic oligomer 156 in a high throughput host infection model. For example, and without limitation, PNAs may undergo in vitro screening in broth cultures. Cultures of each individual pathogen and/or viral gent may be grown in broth or other appropriate medium. PNA molecules may be designed for each strain to either target them individually or in combinatorial manner. Scrambled PNA sequence may be used as control. PNAs may be supplied in a range of concentrations (0-50 µM) to the various combination of cultures for a period of 24 hours. The number of viable cells remaining at the end of this time point may be measured using colony forming unit analysis. The dominant strains in the culture may be identified by sampling liquid culture at end of experiment and measuring relative distribution of the strains using pathogen specific primers in a quantitative polymerase chain reaction (PCR) assay. As used in this disclosure a "polymerase chain reaction" is an instrument that amplifies deoxyribonucleic acid (DNA) samples. In an embodiment, and without limitation, polymerase chain reaction may amplify a small quantity of DNA sample to a large quantity such that an analysis may be performed. In another embodiment, and without limitation, polymerase chain reaction may include a thermal cycling element. As used in this disclosure a "thermal cycling element" is an element that exposes a first chemical to repeated cycles of heating and colling. In an embodiment, and without limitation, thermal cycling element may allow for DNA melting, enzyme-driven DNA replication, and the like thereof. In an embodiment, and without limitation, polymerase chain reaction may include a primer. As used in this disclosure a "primer" is a single-stranded nucleic acid used by living organisms in the initiation of DNA synthesis. In an embodiment, and without limitation, primer may include an oligonucleotide that is a complementary sequence to a target DNA region. Additionally or alternatively, polymerase chain reaction may include a DNA polymerase. As used int this disclosure a "DNA polymerase" is an enzyme that catalyzes the synthesis of DNA molecules from molecular precursors of DNA. In an embodiment, and without limitation, DNA polymerase may create two identical DNA duplexes from a single original DNA duplex. In another embodiment and without limitation, DNA polymerase may create a nucleotide to a three prime (3')-end of a DNA strand. In an embodiment, and without limitation, DNA polymerase may include a heat-stable DNA polymerase. As used in this disclosure a "heat-stable DNA polymerase" is an enzyme capable of catalyzing DNA synthesis at high temperatures. For example, and without limitation, heat-stable DNA polymerase may include a Taq polymerase enzyme. In an embodiment and without limitation, polymerase chain reaction component may be configured to perform DNA cloning, gene cloning, gene manipulation, gene mutagenesis, construction of DNA-based phylogenies, diagnosis of genetic disorders, monitoring of genetic disorders, amplification of DNA, analysis of DNA genetic fingerprints, detection of pathogens in nucleic acid tests, and the like thereof. Additionally or alternatively, validation protocol may measure one or more efficacies and/or toxicities as a function of a high throughput fluorescent infection assay that may quantify the effectiveness of select PNAs.

Still referring to FIG. 1, synthesizing therapeutic oligomer 156 further comprises updating genomic library 112 as a function of the therapeutic oligomer and a genomic outcome. As used in this disclosure a "genomic outcome" is one or more gene expression modifications and/or physiological responses to therapeutic oligomer. In an embodiment, and without limitation, genomic outcome may be determined as a function of profiling a gene expression in response to a PNA. For example, and without limitation, gene expression may be profiled as a function of a differential expression in outer membrane porin operon (omp) genes, previously linked to carbapenem-resistance, and resistance-related genes. As a further non-limiting example, ompF may be found to be significantly differentially expressed in any condition with respect to no treatment (under expressed in meropenem, 30 minutes), wherein ompA and ompC expression tracked closely with the no treatment conditions in all experiments. Additionally or alternatively, expression levels of the ertapenem and meropenem experiments may be directly compared at each time point, wherein none of the three genes were found to be significantly differentially expressed, and wherein no resistance-related genes were differentially expressed in any condition. In an embodiment, and without limitation, a gene expression may be profiled in response to ertapenem and/or meropenem treatment. For example, viral agent influenza A may be exposed to ertapenem and/or meropenem and a gene expression profile may be examined after a period of time, such as but not limited to seconds, minutes, hours, days, and the like thereof. Viral agent influenza A may be diluted 1:20 from overnight cultures and grown for 1 hour to exponential phase prior to treatment with 2 µg/mL of ertapenem or 1 µg/mL of meropenem. In an embodiment, genomic expression may be monitored as a function of comparing the RNA sequencing data from ertapenem- and meropenem-treated samples to an untreated control at the same timepoint. General expression trends may be evaluated using hierarchical clustering across genes and conditions. Conditions may be found to cluster by timepoint which may suggest a generalized and transient response. For example, and without limitation, 41 transcripts that were DE in both treatments after 30 minutes of exposure, six transcripts DE in both antibiotics after 60 minutes of exposure, and six that were DE in both treatments at 30 and 60 minutes may be evaluated as a function of a hierarchical clustering. In an embodiment, and without limitation, genes such as flhC and flhD may code for components of the transcriptional regulator FlhDC, which may be responsible for regulating motility associated functions such as swarming and flagellum biosynthesis. Both flhC and flhD genes may be significantly under expressed at 30 and 60 minutes.

Still referring to FIG. 1, synthesizing therapeutic oligomer 156 may include incorporating therapeutic oligomer 156 into a vector delivery system. As used in this disclosure a "vector delivery system" is a delivery vehicle that aids in delivering one or more therapeutic oligomers to a target host. In an embodiment, and without limitation, vector delivery system may include one or more probiotic microorganisms. For example, and without limitation, probiotic microorganisms that may act as a delivery vehicle for one or more PNAs include yeasts such as *Saccharomyces, Debaromyces, Candida, Pichia* and *Torulopsis*, molds such as *Aspergillus, Rhizopus, Mucor*, and *Penicillium* and *Torulopsis* and bacteria such as the genera *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus* GG), *Lactobacillus* sake, *Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus*, and *Staphylococcus xylosus*. In another embodiment, vector delivery system may include one or more bacteria based "Micro-Robots" using Type III bacterial secretion systems. For example, and without limitation, bacteria based "Micro-Robots" may repurpose bacterial secretion systems, such as Type III (T3SS) or Type IV secretion systems, to deliver PNAs. As a further non-limiting example, bacteria based "Micro-Robots" may include T3SS, which are molecular machines used by many gram-negative bacterial pathogens including pathogens *Shigella, Yersinia, Salmonella* and *Pseudomonas*, to inject proteins, known as effectors, directly into eukaryotic host cells. In an embodiment, and without limitation, bacteria based "Micro-Robots" may include proteins that manipulate host signal transduction pathways and cellular processes to the pathogen's advantage. Additionally or alternatively, synthesizing therapeutic oligomer 156 may include administering vector delivery system and/or therapeutic oligomer 156 to an organism, user, subject, and the like thereof.

In an embodiment, and still referring to FIG. 1, bacteria based "Micro-Robots" may repurpose the intrinsic Type III secretion system in a gram bacterium, such as *Salmonella*, wherein gram bacteria may uptake and deliver PNAs to a target eukaryotic cell. In another embodiment, a T3SS function may be introduced in a non-pathogenic strain of bacteria, such as *E. Coli* Nissle 1917, a probiotic strain that is easily culturable, and been tested in humans for treatment of irritable bowel syndrome. In this embodiment, a T3SS from a pathogen such as *Shigella flexneri* may be incorporated into a synthetic biology-based approach where such a protein delivery system may be composed of two parts: (i) a ~31 kb long minimal DNA sequence that contains operons required for a functional T3SS from *S. flexneri*, and (ii) the transcriptional activator VirB to induce expression of the T3SS. In another embodiment bacteria based "Micro-Robots" may include a kill switch circuit under the control of the Ipac promoter (Ipac is the native *Shigella* T3SS encoded translocator protein that may get activated once *Shigella* invades a mammalian cell) to activate cell lysis once *E. Coli* enters mammalian cells. This may address both bio-safety concerns that *E. coli* Nisseria 1917 should be killed once it has entered the mammalian cell, as well as result in efficient secretion of the PNA-CPP molecules. In this preferred embodiment, a kill switch design is based on the expression of a holin and antiholin. Holin is a protein that forms pores in cell membranes. Anti-holin forms a dimer with holin, which is not active. Once pores are formed by holin, lysozyme can access the periplasmic space and degrade the cell wall, causing cell lysis.

In another embodiment, and still referring to FIG. 1, vector delivery system may include a nanoparticle-based delivery system. As used in this disclosure a "nanoparticle-based delivery system" is delivery vehicle comprising one or more nanoparticles and/or nanospheres, wherein a nanoparticle is described above. For example, and without limitation, nanoparticle delivery system may provide a delivery vehicle for enhanced PNA transport, lowered toxicity, and increased bioavailability. In an embodiment, and without limitation, nanoparticle-based delivery system may include a gold nanoparticle delivery system. In an embodiment, and without limitation, nanoparticle-based delivery system may include a liposome, nanoliposome, nano-lipid sphere, transfersome, noisome, ethosome, nanovesicle, and the like thereof. Additionally or alternatively, therapeutic oligomers may be introduced to mammalian cells as a function of being exposed to radiation, such as gamma-radiation. In this embodiment, the inventors may use a high throughput screening method for the developed PNA molecules using human macrophages, and hematopoietic stem cells exposed to gamma-radiation, and in some instances microgravity to better simulate conditions in space. The target PNAs may be tested to demonstrate gene-specificity, reduced radiation response, increased transport, the lowered toxicity.

In an embodiment, and still referring to FIG. 1, therapeutic oligomers and/or PNAs may be designed and/or synthesized to allow for PNA antisense inhibition of RNA sequencing targets. In an embodiment, method 100 may include designing and/or synthesizing antisense PNA structures. For example, and without limitation, designing antisense PNA may include using transcriptomic data to generate a list of gene targets, which, together with a whole-genome assembly and genome annotation, may be used as inputs for the FAST tool PNA Finder, wherein the tool may be used to design multiple antisense PNA candidates for each gene target, with 12-mer sequences—a length that seeks to optimize both specificity and transmembrane transport—that were complementary to mRNA nucleotide sequences surrounding the translation start codon. PNA Finder may then filter this set of candidates to minimize the number of predicted off-targets within the pathogen genome, to maximize solubility, and to avoid any self-complementing sequences. For the FAST Build module, a single PNA for each gene target may be selected and synthesized using Fmoc chemistry. These PNA may then be tested in cultures in combination with each carbapenem to determine whether the two treatments would interact as predicted. A two-way ANOVA test may be used to assess interaction significance, and normalized S-value were used to compare the observed growth to the expected growth, as predicted by the Bliss Independence Model for drug combinations, wherein normalized S-value is described above in detail.

In an embodiment, and still referring to FIG. 1, therapeutic oligomer 156 may be multiplexed. As used in this disclosure "multiplexing" is incorporating two or more therapeutic oligomers to achieve therapeutic effect. For example, and without limitation, multiplexing may include multiplexing two or more therapeutic oligomers such that CSF-2 may be upregulated, IL-10 may be upregulated, and/or TNF-α may be downregulated. In an embodiment, and without limitation, multiplexing two or more therapeutic oligomers comprising CSF-2 upregulators and/or IL-10 upregulators may reduce the expression of proinflammatory cytokines and/or increase IL-10 expression. In an embodiment, and without limitation, multiplexing may allow for therapeutic profile immune engineering therapeutics.

Figure 2:
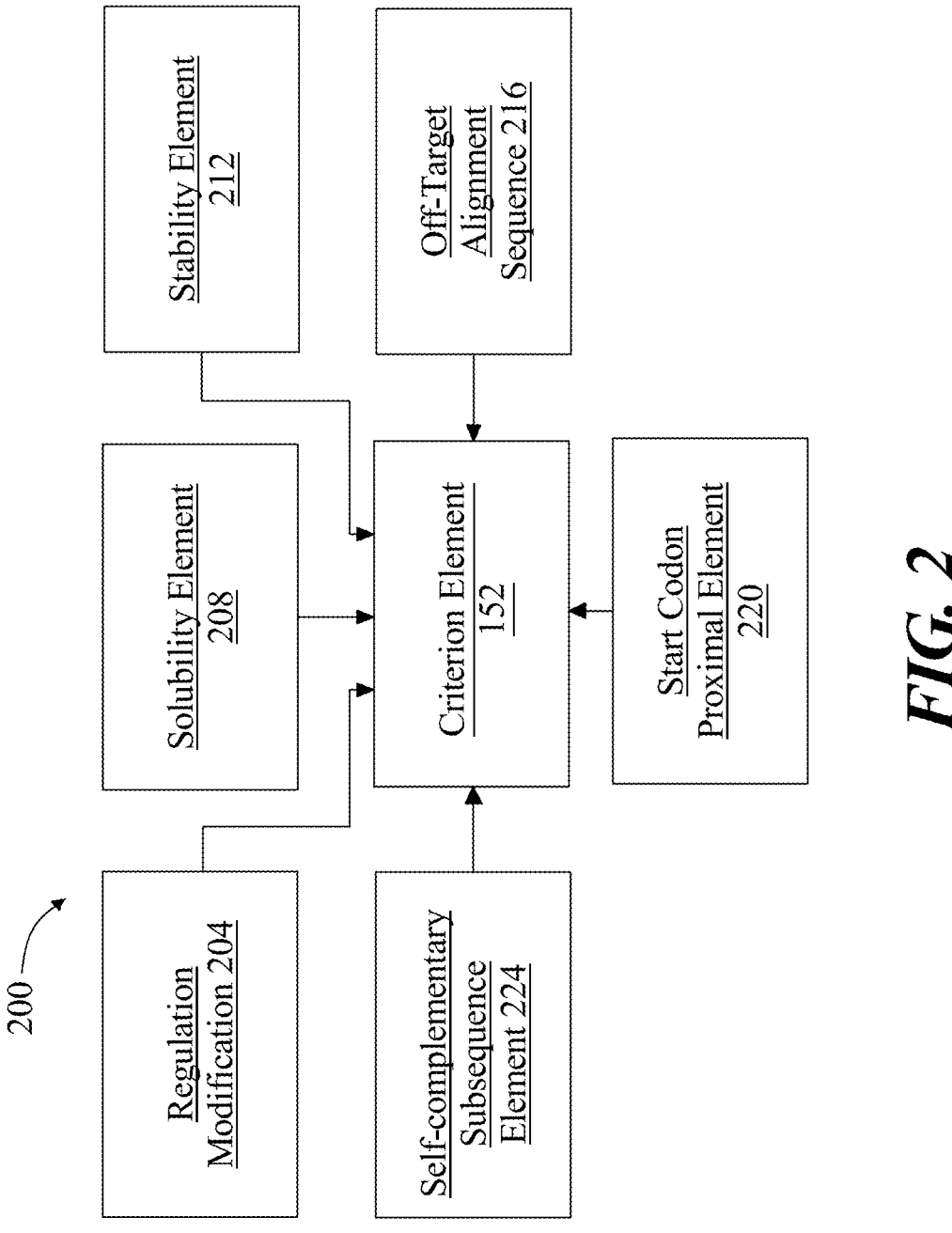
FIG. 2 is a block diagram illustrating an exemplary embodiment of a criterion element.

Now referring to FIG. 2, an exemplary embodiment of a criterion element 152 is illustrated. As used in this disclosure a "criterion element" is an element of data denoting one or more principles and/or standards that a therapeutic oligomer sequence. In an embodiment and without limitation, criterion element 152 may be identified as a function of a screening and/or analysis of previously synthesized therapeutic oligomers, wherein analysis and/or screening is described above. In another embodiment, and without limitation, criterion element 152 may be identified as a function a chemical property database. As used in this disclosure a "chemical property database" is a database and/or datastore of chemical properties of molecules and/or oligomers. In an embodiment, and without limitation, chemical property database may include a structure element, safety element, molecular formula, molecular weight, toxicity element, physical description, color, form, odor, taste, boiling point, melting point, density, vapor pressure, Log P, viscosity, corrosivity, heat of vaporization, surface tension, refractive index, polarity, dipole moment, and the like thereof. For example, and without limitation criterion element 152 may include a regulation modification 204. As used in this disclosure a "regulation modification" is an effect and/or influence that a proposed therapeutic oligomer sequence may have on a gene target expression. As used in this disclosure a "gene expression" is a process that synthesizes a functional gene product from a gene. For example and without limitation, gene expression may include producing end products such as, but not limited to proteins and/or non-coding RNA structures. For example, and without limitation, regulation modification 204 may denote an inhibition of a gene target expression. As a further non-limiting example, regulation modification 204 may denote an upregulation of a gene target expression. In an embodiment, and without limitation, regulation modification 204 may denote that GM-CSF and/or CSF2 may be upregulated to increase protein expression. In another embodiment, and without limitation, regulation modification 204 may upregulate one or more associated G-CSF, growth factors, and/or a significant number of proinflammatory cytokines, such as but not limited to IL-1α, IL-1β, TNF-α, TNF receptors, IL-10, viz., NLRP1, IL-6, TNFR1, and NF-κβ and the like thereof. Additionally or alternatively, regulation modification 204 may denote an upregulation of hemopoietic proteins and/or proinflammatory enzymes. As a further non-limiting example, regulation modification 204 may denote that a proposed therapeutic oligomer sequence may have no effect and/or influence on a gene target expression.

Still referring to FIG. 2, criterion element 152 may include a solubility element 208. As used in this disclosure a "solubility element" is a chemical property of a solvent to dissolve a proposed therapeutic oligomer sequence. For example, and without limitation, solubility property of proposed therapeutic oligomer sequences may be diverse as a function of a common-ion effect, ionic strength element, solubility equilibrium, temperature, and the like thereof. In an embodiment, and without limitation, solubility properties may be variable as a function of the solvent. For example, and without limitation, a solvent element for a proposed therapeutic oligomer sequence may vary as a function of a solvent of gastric acid in comparison to blood. Criterion element 152 may include a stability element 212. As used in this disclosure a "stability element" is a measurable value denoting the magnitude of reactivity of a proposed therapeutic oligomer sequence. For example, and without limitation, stability element 212 may denote that proposed therapeutic oligomer sequence has a high stability as a function of a low Gibbs Free Energy. As a further non-limiting example, stability element 212 may denote that proposed therapeutic oligomer sequence has a low stability as a function of a high Gibbs Free Energy.

Still referring to FIG. 2, criterion element 152 may include an off-target alignment sequence 216. As used in this disclosure an "off-target alignment sequence" is an element of data denoting the number of alignments predicted to inhibit a gene and/or translation. In an embodiment, and without limitation, off-target alignment sequence 216 may be aligned using Clustal X version 2.1 to (i) its own genome, (ii) across desired number of genomes, (iii) across human transcriptome and genome (for any potential side-effects). Genomic analysis of possible binding sites may also be conducted in Artemis using a cut-off of 2 base pair mismatches. Only PNA sequences that uniquely target pathogens and/or viral agents of interested may be considered. For example, in an embodiment, unique PNAs will be designed against known gene sequences obtained from the genome library. Additionally or alternatively, criterion element 152 may include a start codon proximal element 220. As used in this disclosure a "start codon proximal element" is an element of data denoting the proximity of the genomic locus to the start codon of the genomic sequence, wherein the proximity may inhibit a gene and/or translation. For example, and without limitation, start codon proximal element 220 may include a default range that identifies an alignment as a function of being set to (−20, 20), wherein a minor translation inhibition may occur at 17 bases upstream of a beta-lactamase start codon, and wherein no significant translation inhibition may occur 23 bases downstream of the same start codon. In an embodiment, start codon proximal element 220 may vary from gene to gene. Additionally or alternatively, criterion element 152 may include a self-complementary subsequence element 224. As used in this disclosure a "self-complementary subsequence element" is an element of data denoting the presence of one or more complementary binding sequences in a gene strand that may fold, bend, and/or turn to create a double-stranded structure internally. In an embodiment, and without limitation, self-complementary subsequence element 224 may denote the presence of six or more bases that are self-complementary and/or may bond to each other without the presence of an external substrate such as DNA. As a further non-limiting example, self-complementary subsequence element 224 may denote one or more hairpin structures and/or orientations that may enhance a self-complementary subsequence binding affinity.

Figures 3A, 3B:
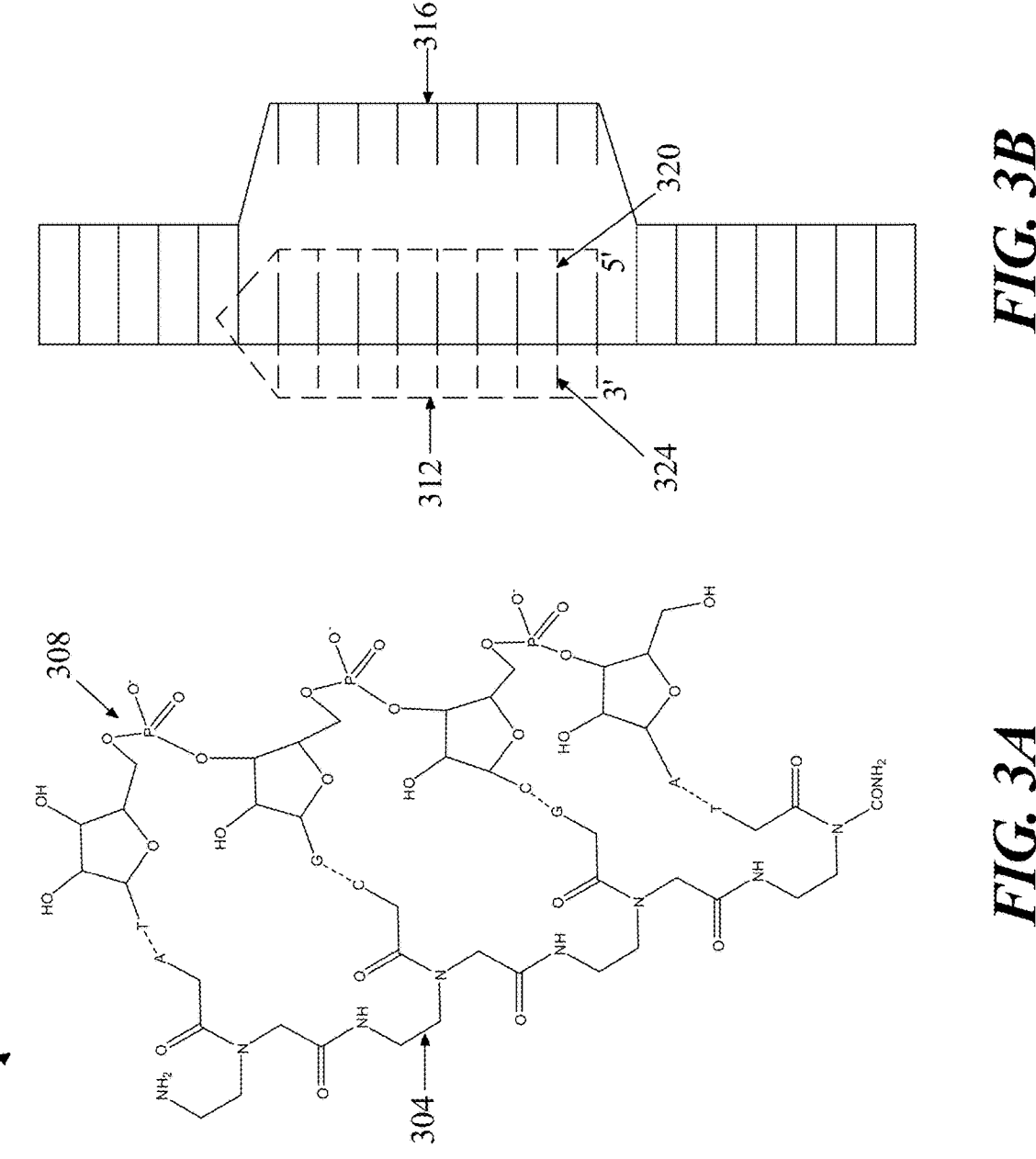
FIG. 3A-B is a diagrammatic representation illustrating an exemplary embodiment of a PNA.

Now referring to FIG. 3, a diagrammatic representation 300 illustrating an exemplary embodiment of a PNA. In an embodiment and without limitation, PNA may include a class of nucleic acid targeting reagents, that may demonstrate strong hybridization and/or specificity to their target cells when compared to a naturally occurring RNA and/or DNA molecule. Referring to FIG. 3A, a PNA may include a synthetic DNA analog in which a 2-N-aminoethylglycine unit 304 may act as a backbone of the plurality of nucleobases. In an embodiment, and without limitation, 2-N-aminoethylglycine unit 304 may replace a phosphodiester bond in a DNA molecule. In another embodiment, 2-N-aminoethylglycine unit 304 may exhibit an increased stability in human blood serum and/or mammalian cellular extracts as a function of a lack of enzymatic cleavage. For example, and without limitation, phosphodiester bond 308 may be cleaved as a function of a phosphodiesterase enzyme that catalyzes the hydrolysis of phosphodiester bond 308, wherein 2-N-aminoethylglycine unit 304 may be unaffected by phosphodiesterase enzyme, which may enhance stability. In an embodiment and without limitation PNA may be an attractive candidate for developing "cloning-free" nucleic acid therapies as a function of the increased stability and/or lack of enzymatic cleavage. Additionally, or alternatively, and now referring to FIG. 3B, PNA may include an antisense single stranded PNA, which may be designed to bond to mRNA, wherein an antigene bis-PNA oligomer 312 may have the ability to bond to double stranded DNA 316. As used in this disclosure a "bis-PNA" is an oligomer that invades DNA 316 by forming a "triplex invasion complex," wherein a triplex invasion complex includes two complimentary homopyrimidine PNA strands connected to each other. For example, and without limitation, a first strand of PNA may target a homopurine DNA binding site as a function of a Watson-Crick base pairing binding 320, wherein a second strand of PNA may interact with the DNA strand using a Hoogsteen base pair binding 324, which may form a very stable PNA2-DNA triplex. As used in this disclosure a "Watson-Crick base pair binding" is a chemical bond that a nucleobase may be secured by. For example, and without limitation Watson-Crick base pair binding 320 may secure an adenine nucleobase to a thymine nucleobase. As a further non-limiting example, Watson-Crick base pair binding 320 may secure a guanine nucleobase to a cytosine nucleobase. As used in this disclosure a "Hoogsteen base pair binding" is a chemical bond that secures a nucleobase as a function of a hydrogen bond in a major groove. For example, and without limitation, Hoogsteen base pair binding 324 may secure one or more nucleobases as a function of the N7 position of a purine base and a C6 amino group position of the pyrimidine. As a further non-limiting example, Hoogsteen base pair binding 324 may include one or more base pair bindings such that a triplex formation of oligonucleotides may form, such as but not limited to triplex-DNA, PNA-DNA triplex, and the like thereof. In an embodiment, and without limitation, PNA and/or antisense PNA may target one or more mRNAs to prevent protein expression, and/or anti-gene PNAs for transcriptional activation.

Figure 4:
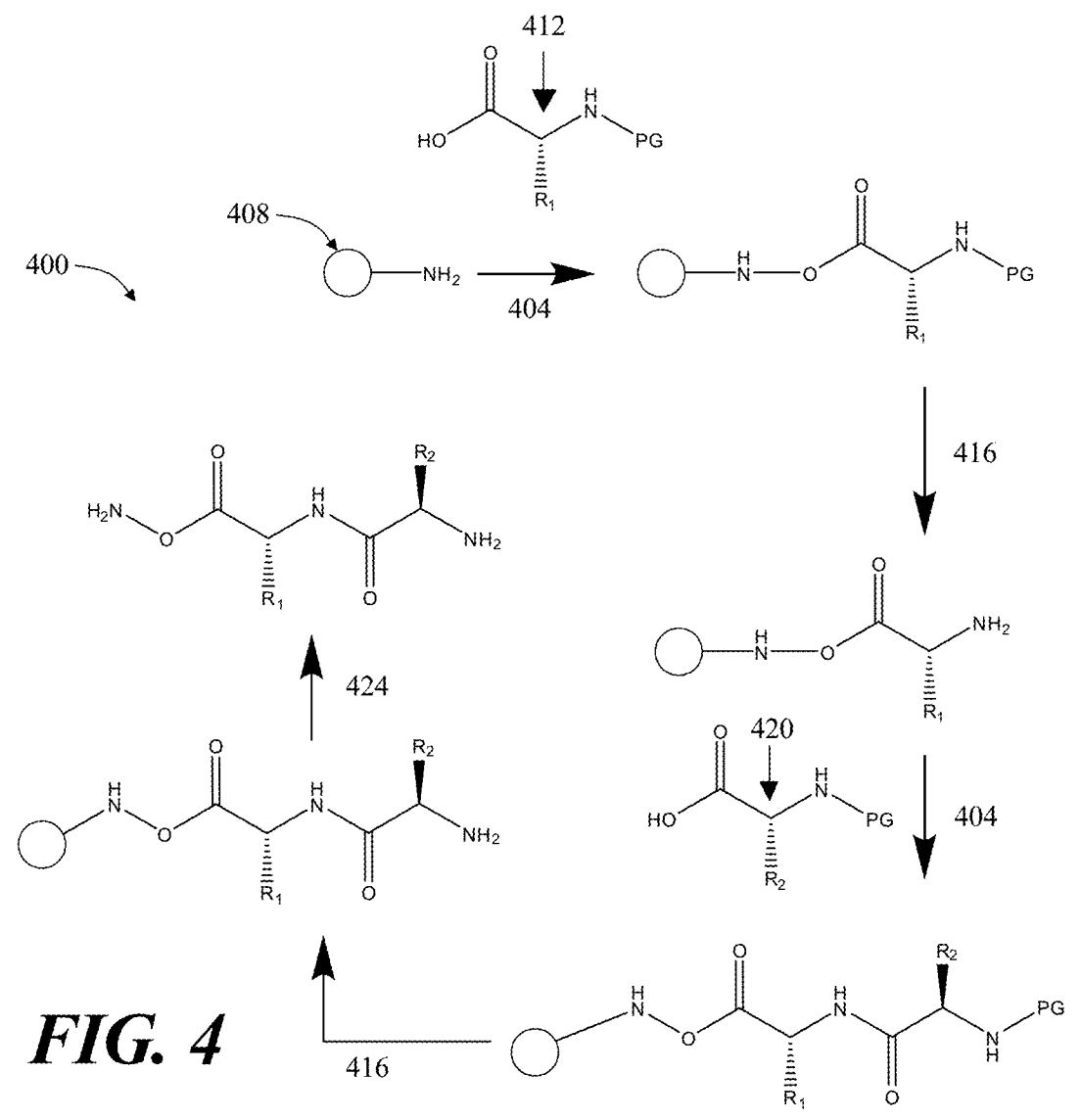

Now referring to FIG. 4, an exemplary embodiment 400 of a peptide synthesis is illustrated. In an embodiment, peptide synthesis may include a coupling process 404. As used in this disclosure "coupling" is a process where two atoms of a molecule are joined together to form a chemical bond. In an embodiment, and without limitation, coupling process 404 may include a heterocoupling process. As used in this disclosure a "heterocoupling process" is a process that combines two different chemical structures. For example, and without limitation, heterocoupling process may include one or more processes such as a Heck reaction of an alkene and an alkyl halide to produce a substituted alkene. As a further non-limiting example, heterocoupling process may include a cross-coupling process, such as Cadiot-Chodkiewicz coupling, Castro-Stephens coupling, Corey-House synthesis, Kumada coupling, Sonogashira coupling, Negishi coupling, Stille cross coupling, Suzuki reaction, Murahashi coupling, Hiyama coupling, Fukuyama coupling, Liebeskind-Srogl coupling, Ullmann-type reaction, Chan-Lam coupling, Buchwald-Hartwig reaction, palladium-catalyzed cross-coupling, and the like thereof. In an embodiment, and without limitation, coupling process 404 may include a homocoupling process. As used in this disclosure a "homocoupling process" is a process that combines two identical chemical structures. For example, and without limitation, homocoupling process may include one or more processes such as a Glaser coupling process that couples and/or chemically bonds two acetylides, which may form a dialkyne. As a further non-limiting example, homocoupling process may include a process, such as a Wurtz reaction, Pinacol coupling reaction, Ullmann reaction, and the like thereof.

Still referring to FIG. 4, coupling process 404 may include a resin 408. As used in this disclosure a "resin" is solid support structure for peptide synthesis. Resin 408 may include any resin that comprises physical stability and/or permits the rapid filtration of liquids. In an embodiment and without limitation, resin 408 may include one or more gel-type support resins, surface-type support resins, and/or composite resins. In another embodiment, and without limitation, Resin 408 may be able to withstand repeated use of trifluoroacetic acid (TFA). In another embodiment, resin 408 may include one or more resins as a function of a desired product such as, but not limited to a C-terminal carboxylic acid and/or an amide. In an embodiment and without limitation, resin 408 may include a Wang resin. Additionally or alternatively, coupling process 404 may include a first peptide 412. As used in this disclosure a "peptide" is a short chain of between two and fifty amino acids linked by a peptide bond. In an embodiment and without limitation, first peptide 412 may include an oligopeptide, dipeptide, tripeptide, tetrapeptide, and the like thereof. In another embodiment, and without limitation, first peptide 412 may include an unbranched peptide chain. In another embodiment, and without limitation, first peptide 412 may include a residue. As used in this disclosure a "residue" is a plurality of amino acids that have been incorporated into a peptide. Additionally or alternatively first peptide 412 may include one or more cyclic peptides comprising an N-terminal and/or amine group and a C-terminal and/or carboxyl group. In an embodiment first peptide 412 may include one or more plant peptides, bacterial and/or antibiotic peptides, fungal peptides, invertebrate peptides, amphibian and/or skin peptides, venom peptides, cancer and/or anticancer peptides, vaccine peptides, immune and/or inflammatory peptides, brain peptides, endocrine peptides, ingestive peptides, gastrointestinal peptides, cardiovascular peptides, renal peptides, respiratory peptides, opiate peptides, neurotrophic peptides, and blood-brain peptides, and the like thereof. In another embodiment first peptide 412 may include one or more post-translational modifications such as, but not limited to phosphorylated modifications, hydroxylated modifications, sulfonated modifications, palmitoylated modifications, disulfide modifications, and the like thereof. In an embodiment and without limitation, first peptide 412 may include a carboxylic acid component, an $R_1$ component comprising a functional group containing a carbon and/or hydrogen atom, and/or an amine group bonded to a protecting group. As used in this disclosure a "protecting group" is a functional group that prevents undesirable side reactions. For example, and without limitation, protecting group may include a Tert-butyloxycarbonyl protecting group, fluorenylmethyloxycarbonyl protecting group (Fmoc) protecting group, carboxybenzyl protecting group, allyloxycarbonyl protecting group, and the like thereof.

Still referring to FIG. 4, peptide synthesis may include a deprotection process 416. As used in this disclosure a "deprotection process" is a process that removes a protecting group from a reagent. For example, and without limitation, deprotection process may deprotect the amino group secured to generate a free amino acid. In an embodiment, and without limitation, deprotection process 416 may include removing the protecting group as a function of an acid, such as but not limited to trifluoroacetic acid, to form a positively charged amino group, wherein the positively charged amino group is then neutralized as a function of a base. In another embodiment, and without limitation, deprotection process 416 may include removing the protecting group as a function of a base, such as but not limited to piperidine. For example, and without limitation, removing the protecting group as a function of a base may result in a neutral amine group, such that no neutralization is required. In an embodiment and without limitation, Peptide synthesis may chemically bond and/or couple a second peptide 420 as a function of coupling process 404, wherein second peptide 420 includes any of the first peptide 412 as described above. Second peptide 420 may include a carboxylic acid component, an $R_2$ component comprising a functional group containing a carbon and/or hydrogen atom, wherein an $R_2$ component may include any of the $R_1$ component structure and/or elements, and/or an amine group bonded to a protecting group, wherein protecting group is described above. In an embodiment, and without limitation, second peptide 420 may be coupled to first peptide, wherein the carboxylic acid component of second peptide 420 may be coupled to the amine group of first peptide 412. In an embodiment and without limitation, second peptide 420 may include a similar protecting group to first peptide 412 and/or a distinct protecting group to first peptide 412. For example, and without limitation, coupling 404 may join a first peptide to a second peptide to form a peptide chain and/or oligomer chain.

Still referring to FIG. 4, peptide synthesis may deprotect the coupled first peptide and second peptide as a function of deprotecting process 416, wherein deprotecting process 416 is described above. In an embodiment, and without limitation, peptide synthesis may be performed iteratively to produce a peptide chain and/or oligomer chain that is any number of peptides long. For example, and without limitation, peptide synthesis may perform iterative processes to result in a peptide chain that is 23 peptides in length. Additionally or alternatively, peptide synthesis may include a cleavage process 424. As used in this disclosure a "cleavage process" is a process that removes resin from the synthesized peptide chain and/or oligomer chain. For example, and without limitation, cleavage process 424 may include using anhydrous hydrogen fluoride to cleave resin 404 from the peptide chain and/or oligomer chain as a function of a hydrolytic cleavage. As a further non-limiting example, cleavage process 424 may include using trifluoroacetic acid to cleave resin 404 from the peptide chain and/or oligomer chain as a function of an acidic cleavage.

Figure 5:
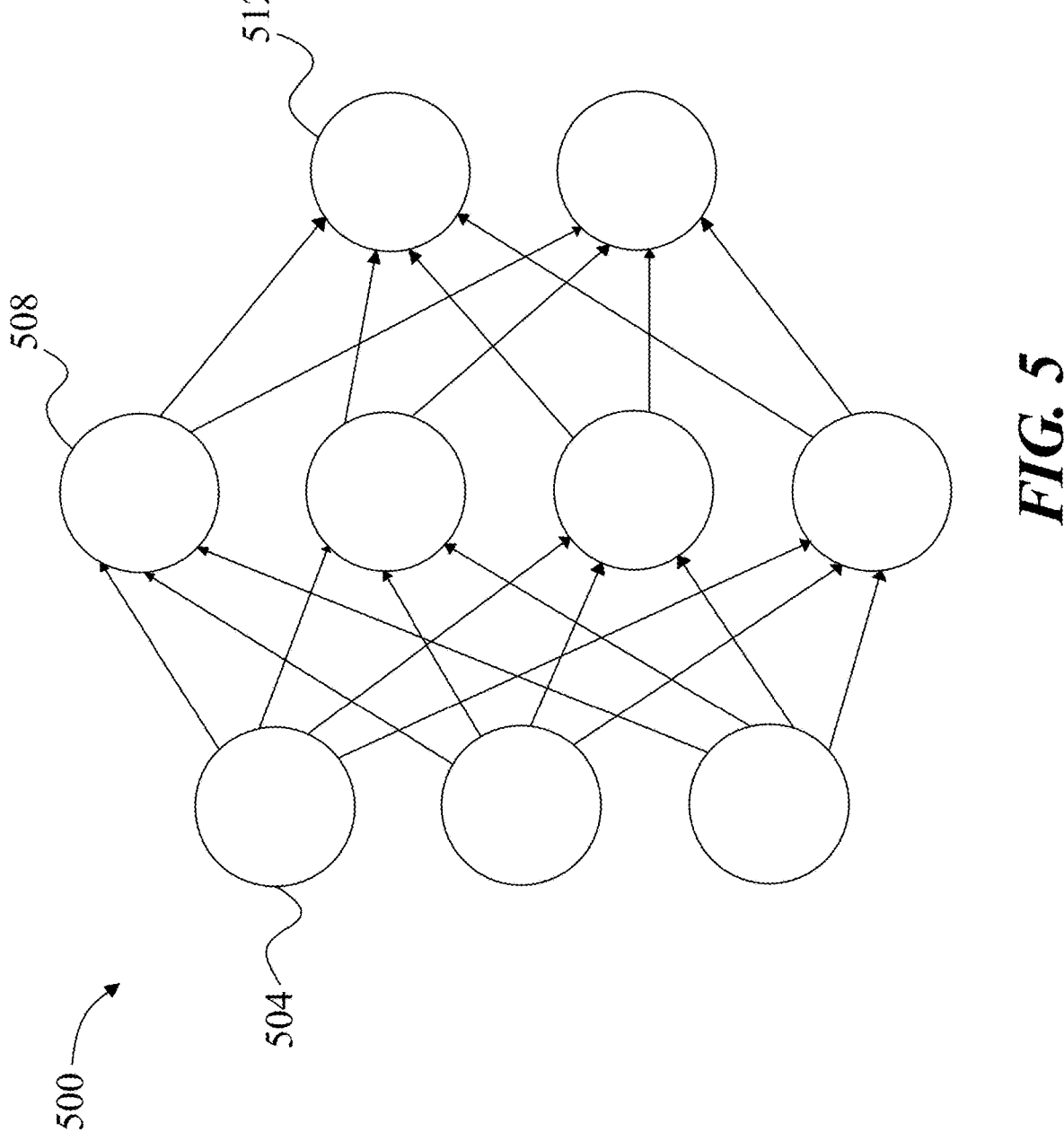
FIG. 5 is a block diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes 504, a suitable training algorithm (such as Levenberg-Marquardt, conjugate gradient, simulated annealing, or other algorithms) is then used to adjust the connections and weights between nodes in adjacent layers 508 of the neural network to produce the desired values at the output nodes 512. This process is sometimes referred to as deep learning. Connections may run solely from input nodes toward output nodes in a "feed-forward" network or may feed outputs of one layer back to inputs of the same or a different layer in a "recurrent network."

Figure 6:
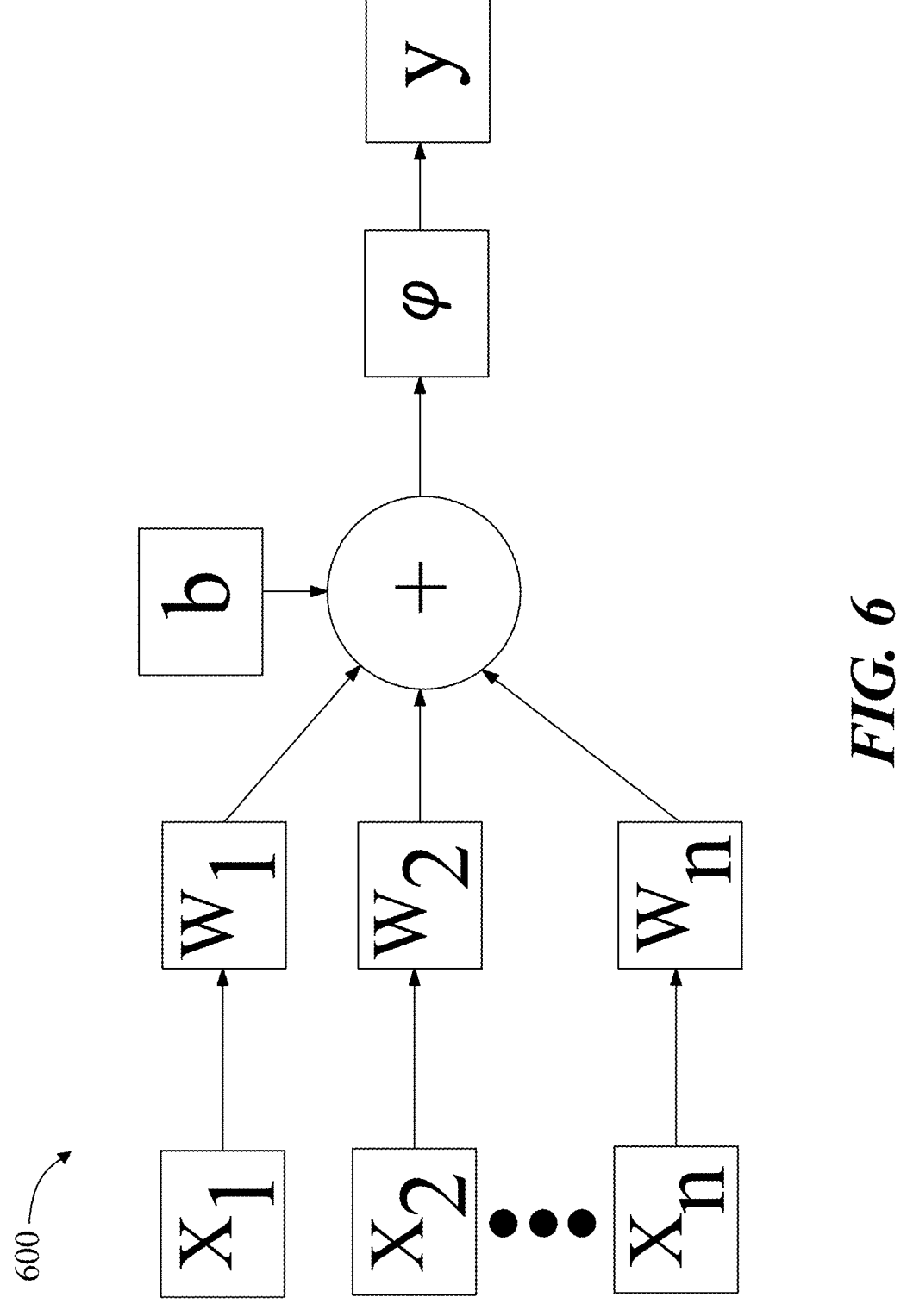
FIG. 6 is a block diagram of an exemplary embodiment of a node in a neural network.

Referring now to FIG. 6, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias $b$ may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input x; may indicate whether the input is "excitatory," indicating that it has strong influence on the one or more outputs y, for instance by the corresponding weight having a large numerical value, and/or an "inhibitory," indicating it has a weak effect influence on the one or more inputs y, for instance by the corresponding weight having a small numerical value. The values of weights $w_i$ may be determined by training a neural network using training data, which may be performed using any suitable process as described above.

Figure 7:
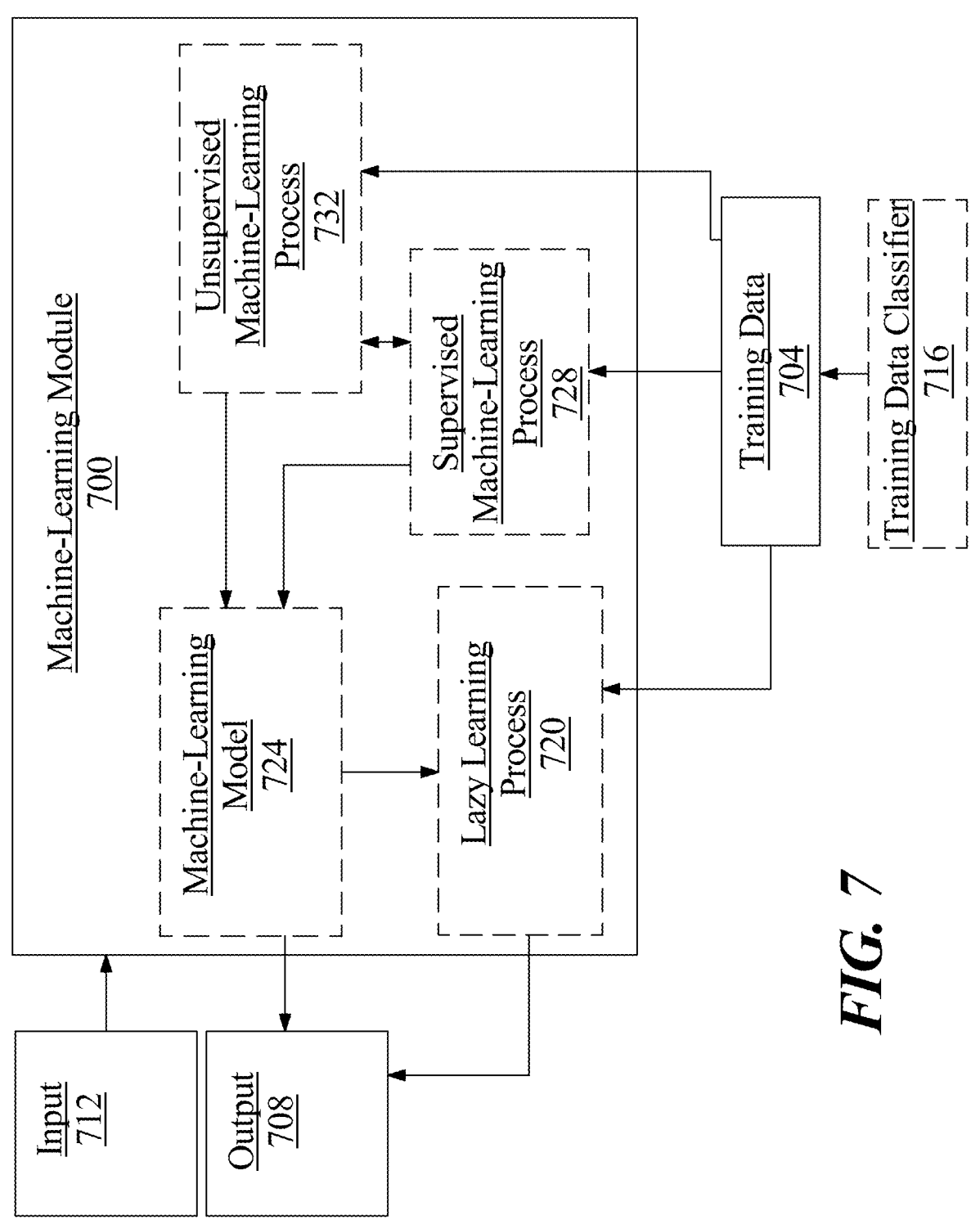
FIG. 7 is a block diagram of an exemplary embodiment of a machine learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative example, inputs may include prospective gene targets, wherein outputs may include a proposed therapeutic oligomer sequence.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a process whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors' classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors' algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 8:
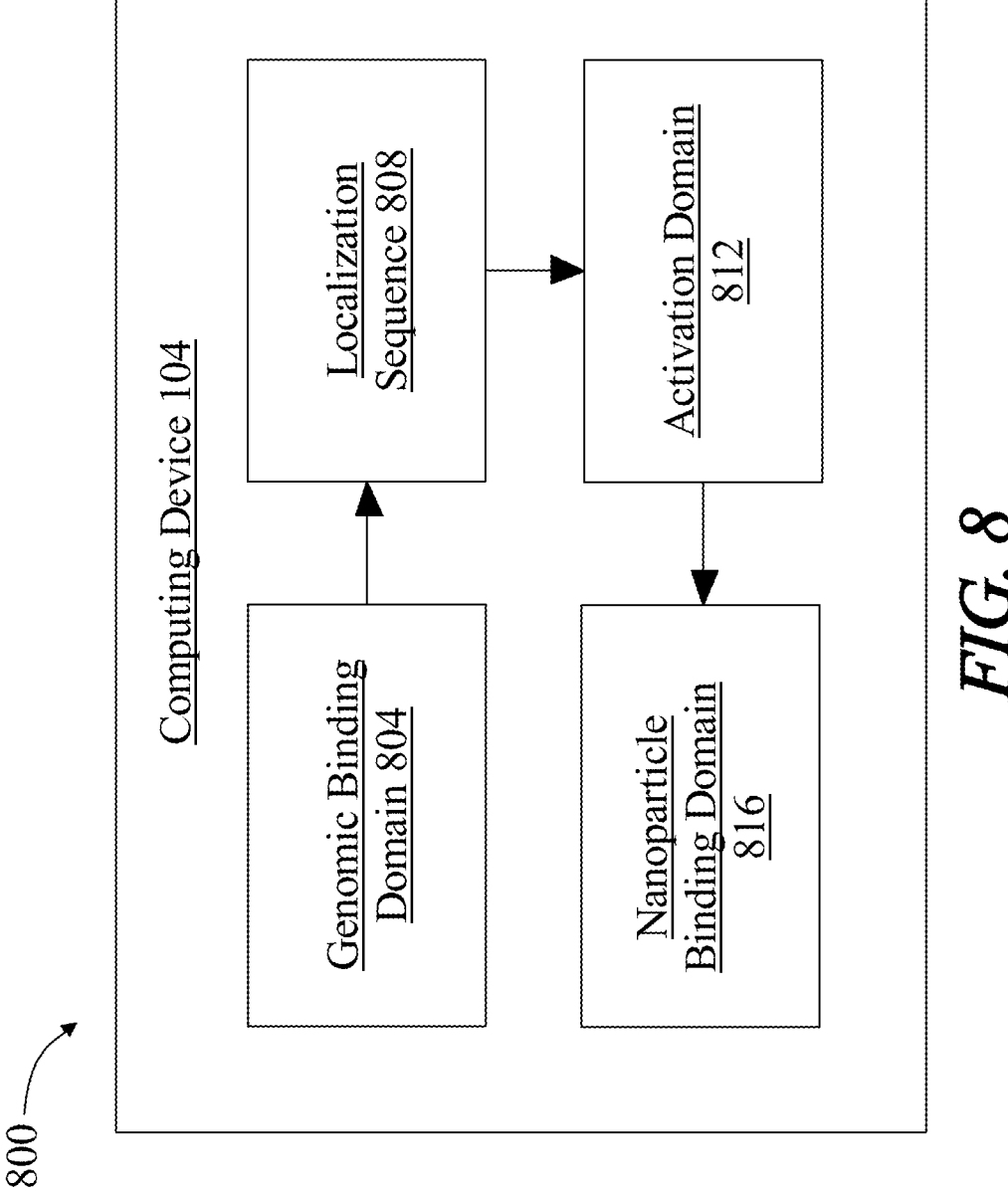
FIG. 8 is a block diagram of an exemplary embodiment of a modular approach.

Now referring to FIG. 8, an exemplary embodiment 800 of a modular approach is illustrated. As used in this disclosure a "modular approach" is a method and/or process to design proposed therapeutic oligomer sequence 108. In an embodiment, and without limitation, modular approach may include determining a genomic binding domain 804. As used in this disclosure a "genomic binding domain" is a genomic sequence of interest and/or a genomic sequence to be regulated. For example, and without limitation, genomic binding domain 804 may include a DNA binding domain and/or an RNA binding domain. In an embodiment, and without limitation, genomic binding domain 804 may comprise identifying a target. As used in this disclosure a "target" is an intended pathogen, viral agent, and/or bacterium to be innervated. For example, and without limitation, target may include a virus, a bacterium, a microbe, and the like thereof. In an embodiment, and without limitation, genomic binding domain may include determine a unique identifier. As used in this disclosure a "unique identifier" is an identifier and/or signature associated to the target. In an embodiment, and without limitation, unique identifier may denote that a target is unique to a specific pathogen, viral agent, and/or bacteria. For example, and without limitation, unique identifier may include a unique genomic sequence and/or unique nucleobase pair sequence. Modular approach may include determining a localization sequence 808. As used in this disclosure a "localization sequence" is a target location to be innervated in the target. In an embodiment, and without limitation, localization sequence 808 may include a nuclear localization sequence. For example, and without limitation, nuclear localization sequence may denote that genomic binding domain 804 is located within a nucleus of a cell. As a further non-limiting example, nuclear localization sequence may denote that genomic binding domain 804 is used for transcriptional inhibition. As a further non-limiting example, nuclear localization sequence may denote that genomic binding domain 804 may be intended for activation.

Still referring to FIG. 8, modular approach may include identifying an activation domain 812. As used in this disclosure an "activation domain" is a location that may be used to activate transcription from a promoter. In an embodiment, and without limitation, activation domain 812 may include acidic domains. As used in this disclosure an "acidic domain" is a domain comprising a large quantity of D and E amino acids. In an embodiment, and without limitation, acidic domain may include well-known activators such as Gal4, Gcn4, VP16, p53, p53 and the like thereof. In another embodiment, and without limitation, acidic domain may include one or more amino acid sequences comprising E TFSD LWKL, D DIEQ WFTE, S DIMD FVLK, D LLDF SMMF, E TLDF SLVT, R KILN DLSS, E AILA ELKK, D DVVQ YLNS, D DVYN YLFD, D LFDY DFLV, D FFDY DLLF, E DLYS ILWS, T DLYH TLWN, and the like thereof. In another embodiment, and without limitation, activation domain 812 may include glutamine-rich domains, proline-rich peptide domains, isoleucine-rich peptide domains, and the like thereof. Additionally or alternatively, modular approach may include a nanoparticle-binding domain 816. As used in this disclosure a "nanoparticle-binding domain" is a location that may be used to bind to a nanoparticle. For example, and without limitation, nanoparticle-binding domain may denote that an oligomer and/or genomic sequence domain may be capable of binding to a nanoparticle. In an embodiment, and without limitation nanoparticle-binding domain 816 may denote that a nanoparticle is less than 2 nm. In another embodiment, and without limitation, nanoparticle-binding domain 816 may denote that a nanoparticle may be fluorescent. As a further non-limiting example, nanoparticle-binding domain 816 may denote that a nanoparticle is FDA approved. In an embodiment, and without limitation, nanoparticle binding domain may denote that a nanoparticle is comprised of gold, zinc, iron oxide, and the like thereof.

Figure 9:
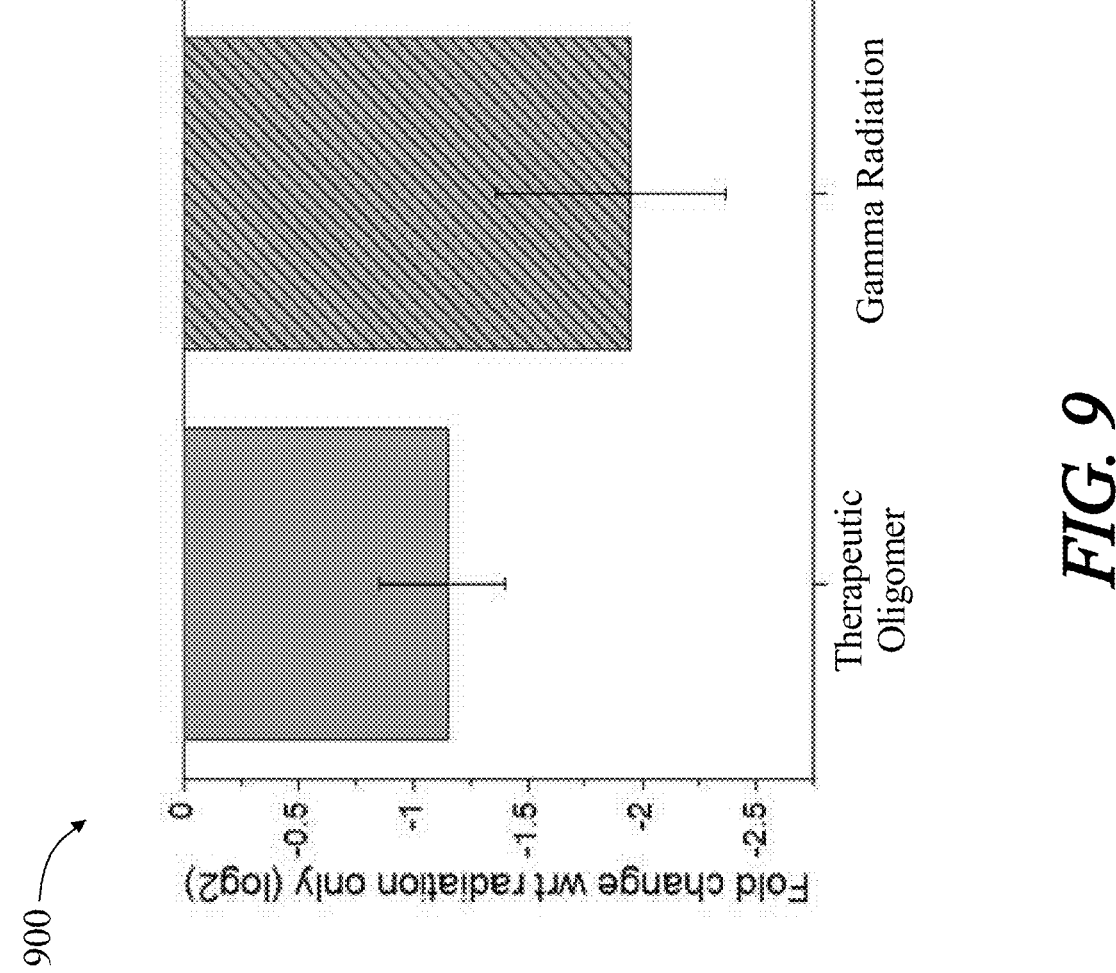
FIG. 9 is a diagrammatic representation of a regulation modification.

Now referring to FIG. 9, an exemplary embodiment 900 of a regulation modification is illustrated. In an embodiment, and without limitation, therapeutic oligomer 156 may downregulate one or more inflammatory genes such as IL-la when compared to gamma-radiation stimulated inflammatory genes in donor-derived human PBMCs. In another embodiment, and without regulation modification may downregulate one or more proinflammatory cytokines. For example, and without limitation, regulation modification may regulate G-CSF and/or Colony-stimulating factor 3 (CSF-3), Stromal cell-derived factor 1 (SDF-1), Epicatchetin (EC) as small molecule ROS inhibitor comparison, Erythropoietin (EPO), Stem cell factor (SCF), TNF-α; Thrombopoietin (THPO), Fms related tyrosine kinase 3 ligand (FLT3LG), IL-3, IL-1α, THPO-isoform; IL-6; IL-1β and/or CSF-2. In another embodiment, and without limitation, therapeutic oligomer 156 may downregulate one or more inflammatory genes such as IL-1β when compared to gamma-radiation stimulated inflammatory genes in donor-derived human peripheral blood mononuclear cells (PBMCs). In another embodiment, and without regulation, therapeutic oligomer 156 may downregulate one or more inflammatory genes such as IL-6 when compared to gamma-radiation stimulated inflammatory genes in donor-derived human PBMCs. 3-fold downregulation of IL-6 gene, compared to untreated PBMCs. Additionally or alternatively, regulation modification may downregulate more than 14 additional proinflammatory cytokines associated to neurodegeneration.

Figure 10A:
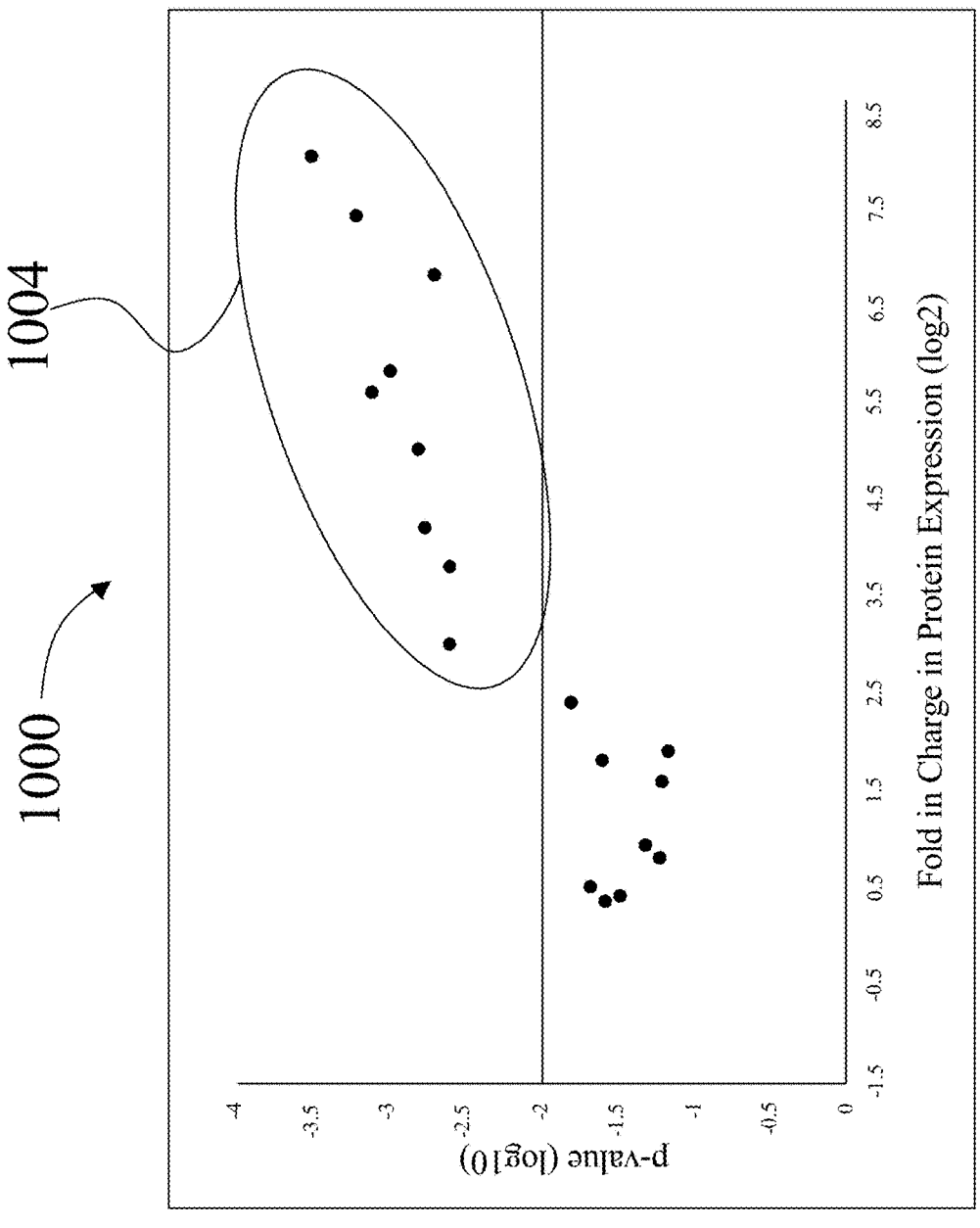
FIGS. 10A-C is a diagrammatic representation of a therapeutic effect.
Figure 10B:
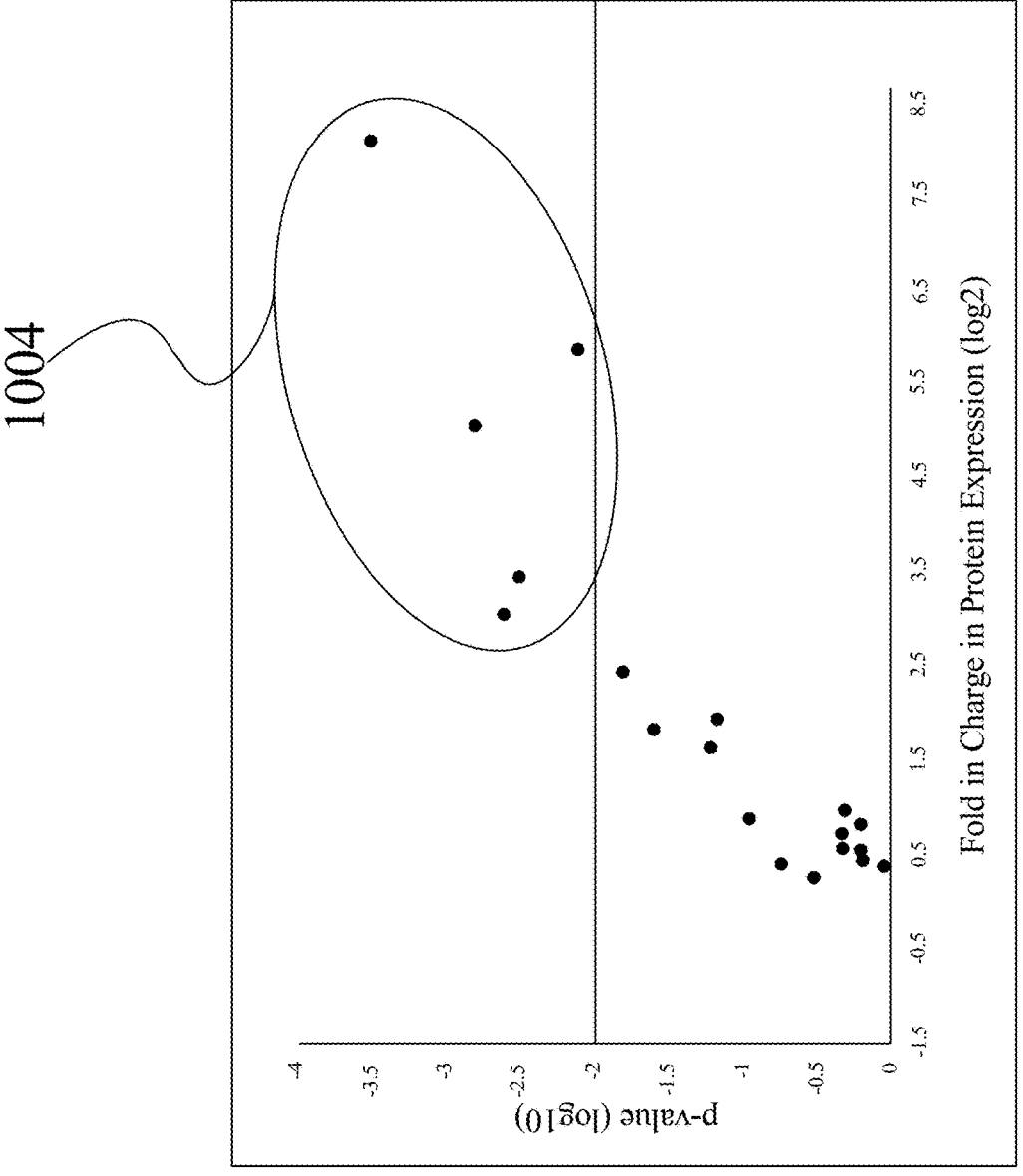
Figure 10C:
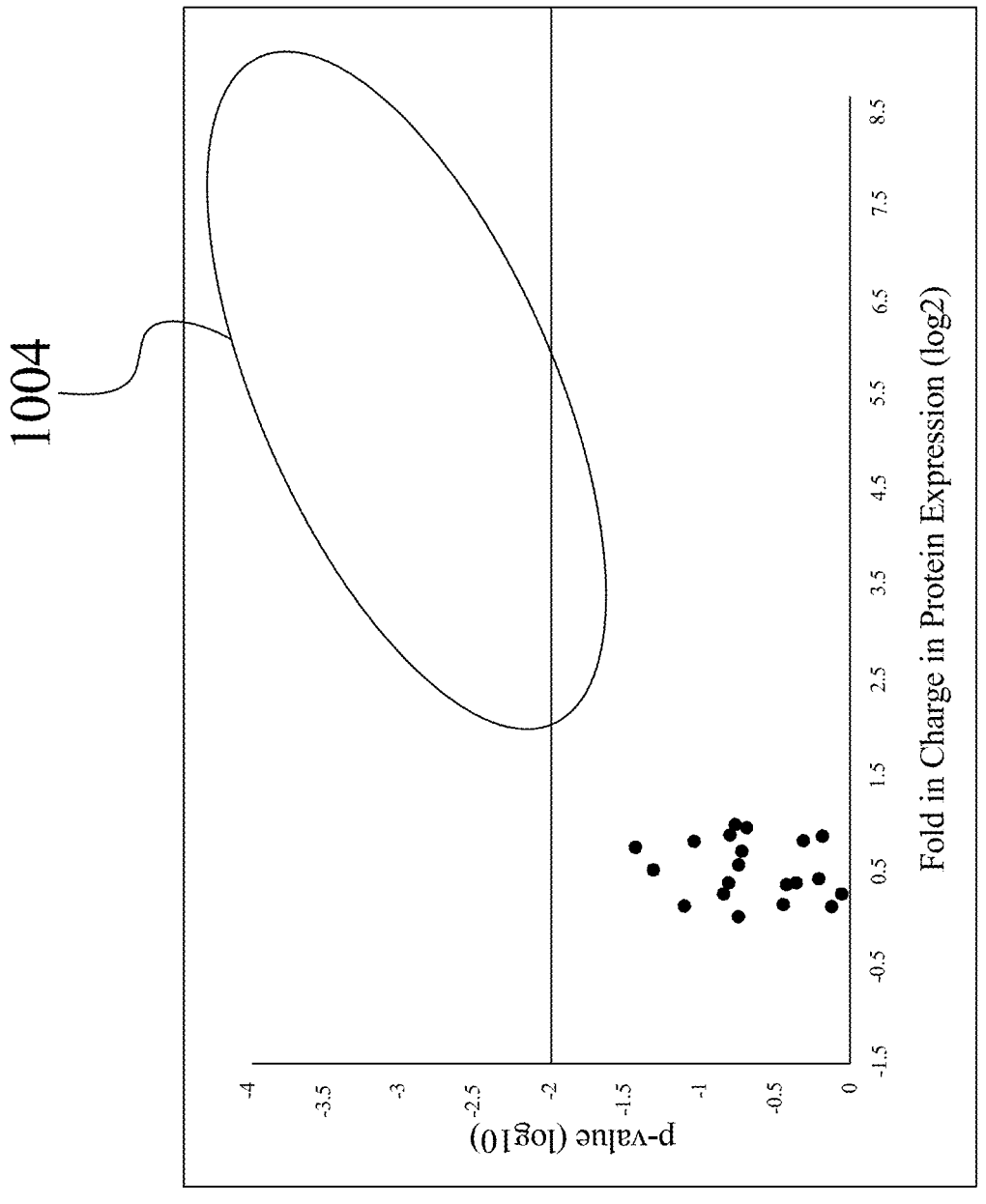

Now referring to FIG. 10, an exemplary embodiment 1000 of a therapeutic effect is illustrated. In an embodiment, and without limitation, therapeutic effect may denote a reduced neuroinflammation in cytokine-stimulated primary human astrocytes. For example, and without limitation, and referring to FIG. 10A, untreated primary human astrocytes may show strong inflammation as seen in cytokine cocktail, wherein a cytokine cocktail may include but is not limited to IL-1 IL-1α, TNF-α, and/or complement component C1q, wherein stimulated cells may release proinflammatory cells that are measured as a function of a p-value and/or enrichment and fold-change with respect to untreated human astrocytes. In an embodiment, untreated primary human astrocytes may denote a high inflammation denoted by an inflammatory grouping 1004. As used in this disclosure an "inflammatory grouping" is a collection of data points that depict one or more frequencies of proinflammatory cell stimulation that exist below a p-value of −2. For example, inflammatory grouping in untreated cells may comprise a large frequency of proinflammatory cell stimulation. Now referring to FIG. 10B, primary human astrocytes treated with small molecule NF-kβ inhibitor may reduce neuroinflammation as a function of a reduced inflammatory grouping 1004. Additionally, or alternatively, and now referring to FIG. 10C, therapeutic oligomer 156 may eliminate neuroinflammation as a function of an eliminated inflammatory grouping 1004.

Figure 11:
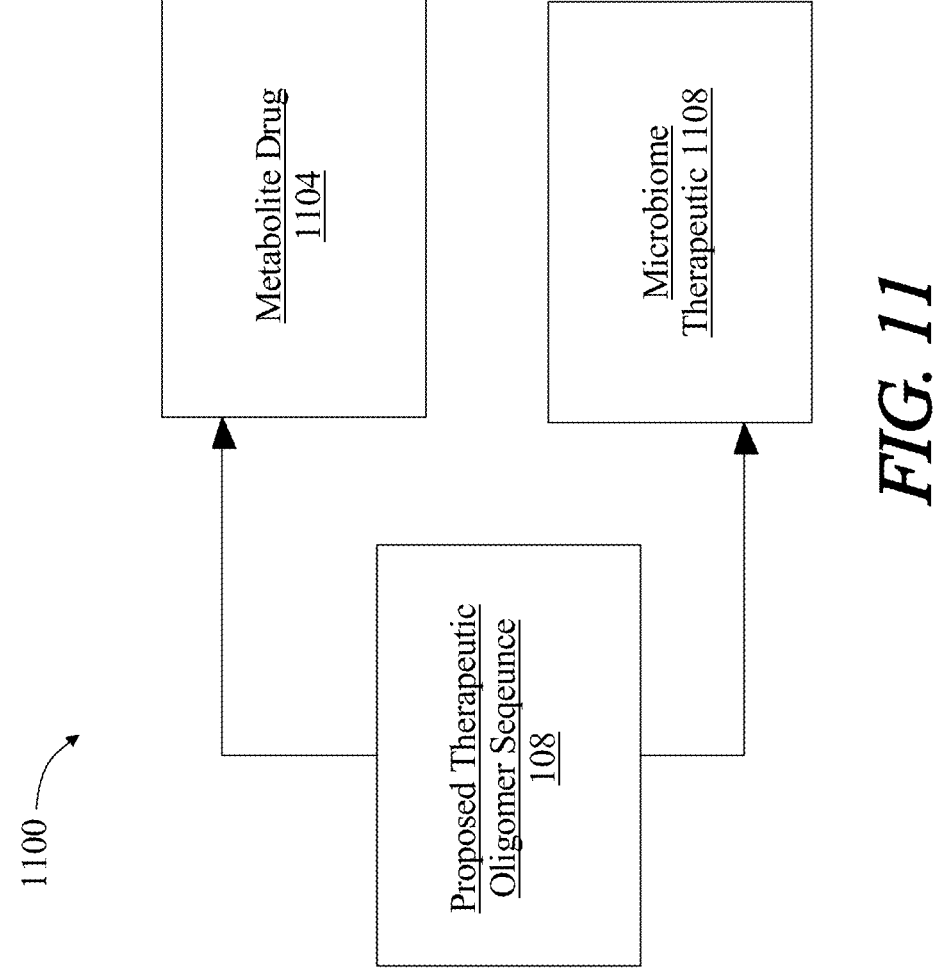
FIG. 11 is a block diagram illustrating an exemplary embodiment of a proposed therapeutic oligomer.

Now referring to FIG. 11, an exemplary embodiment 1100 of proposed therapeutic oligomer sequence 108 is illustrated. Proposed therapeutic oligomer sequence 108 may include a sequence to stimulate a metabolite drug 1104. As used in this disclosure a "metabolite drug" is a bacterial metabolite that directs a microbiome towards a desired state. In an embodiment, and without limitation metabolite drug 1104 may include bacterial metabolites that include growth-promoting and/or growth-inhibiting factors. For example, and without limitation metabolite drug 1104 may include a bacterial metabolite such as GM-CSF, G-CSF, and the like thereof. Proposed therapeutic oligomer sequence 108 may include a microbiome therapeutic 1108. As used in this disclosure a "microbiome therapeutic" is a therapeutic that directs a microbiome towards a desired state. In an embodiment, and without limitation microbiome therapeutic 1108 may include therapeutics such as antisense nanoligomers that may target a peptidase domain-containing ABC transporter gene.

Figure 12:
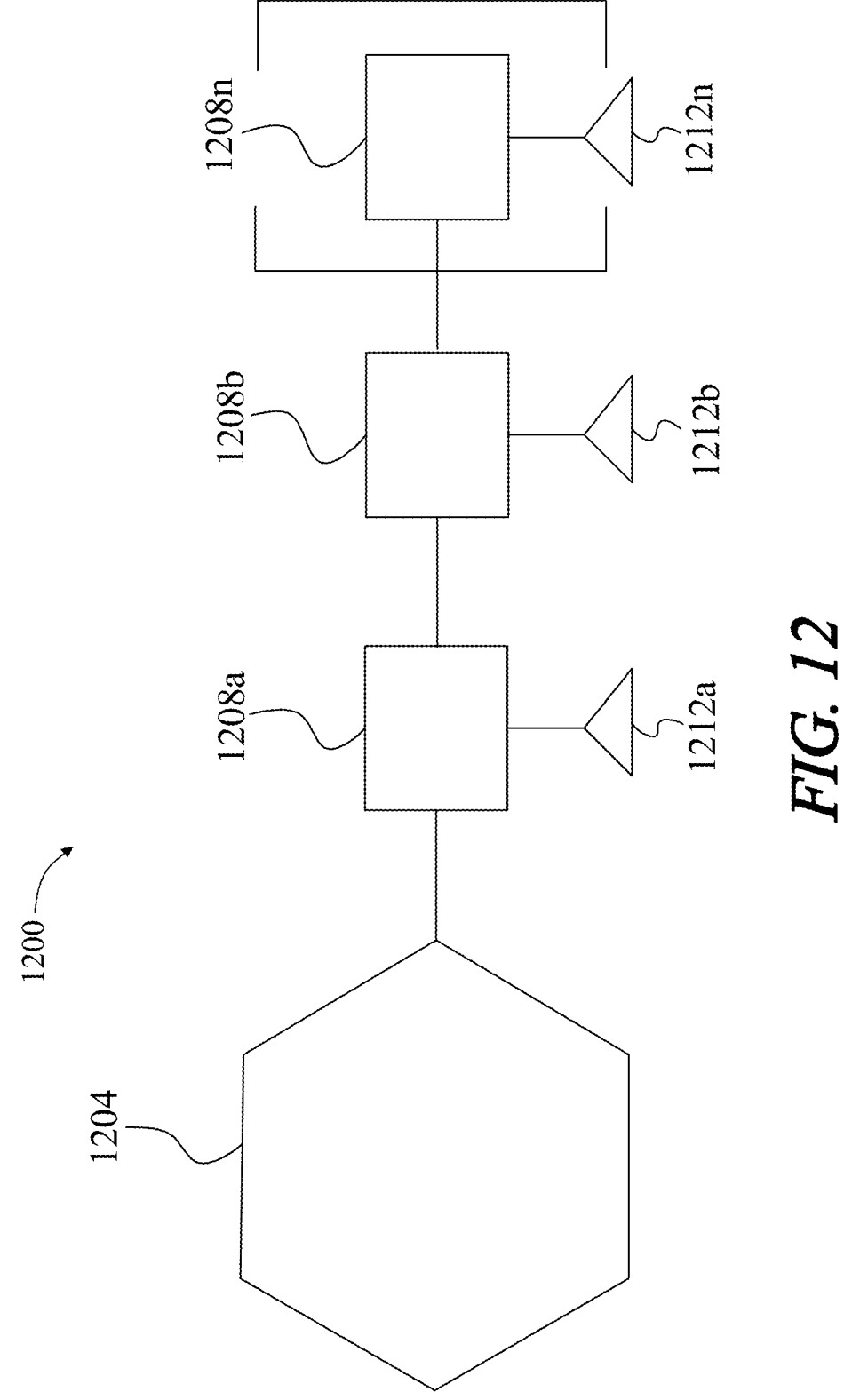
FIG. 12 is a diagrammatic representation illustrating an exemplary embodiment of a therapeutic oligomer.
Figure 13B:
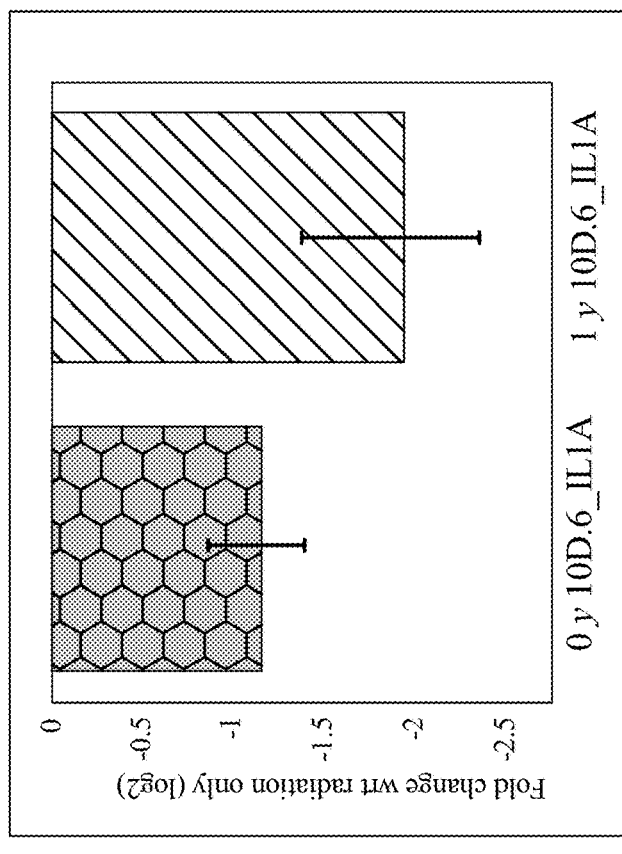
FIGS. 13A-C is a diagrammatic representation illustrating an exemplary embodiment of nanotherapeutic oligomers.
Figure 13B:
Figure 13A:
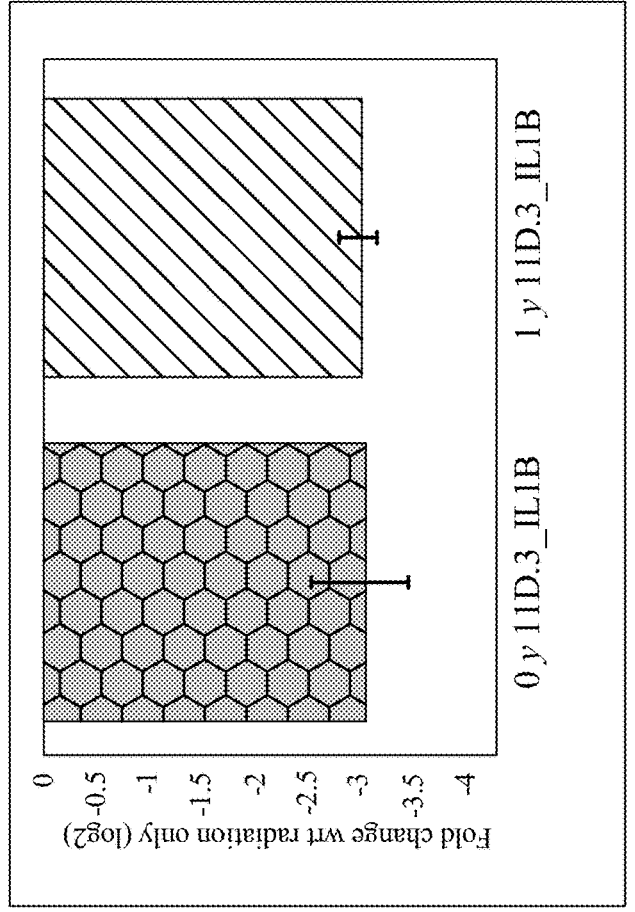
Figure 13C:
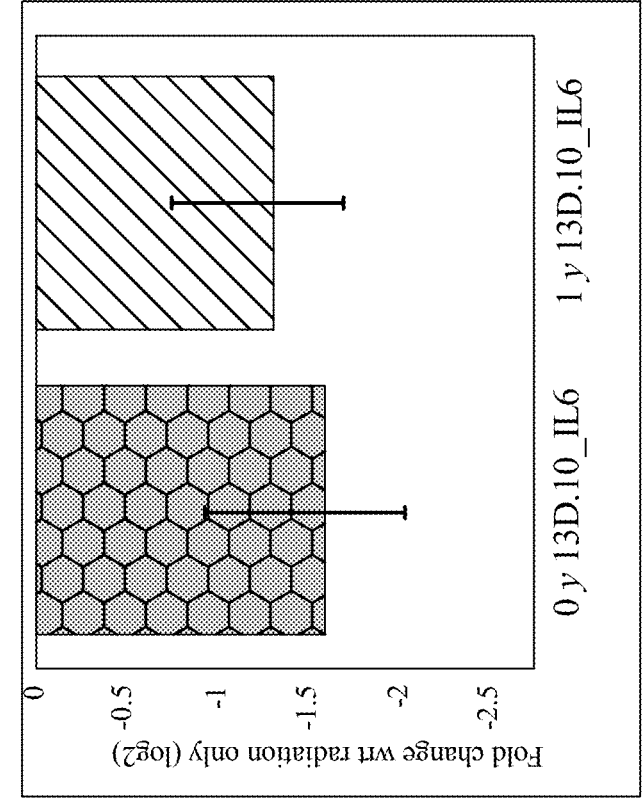

Now referring to FIG. 12, an exemplary embodiment 1200 of a therapeutic oligomer is illustrated. In an embodiment, and without limitation, therapeutic oligomer 156 may include a support structure 1204. As used in this disclosure a "support structure" is a structure comprising a physical stability that may be bound to a molecule and/or polymer. In an embodiment, and without limitation, support structure 1204 may include a nanoparticle, wherein a nanoparticle is a three-dimensional object existing on a nanoscale, wherein the particle is between 0.1 nm and 100 nm in each spatial dimension. For example, and without limitation, nanoparticle may include a spherical nanoparticle with a diameter of 23 nm. In an embodiment, and without limitation, nanoparticle may include a transition metal nanoparticle. For example, and without limitation, transition metal nanoparticle may include a gold nanoparticle. As a further non-limiting example, transition metal nanoparticle may include a copper nanoparticle. As a further non-limiting example, transition metal nanoparticle may include a zinc nanoparticle. In an embodiment, and without limitation, transition metal nanoparticle may include one or more transition metals comprising groups 3-12 transition metals on the period table of elements. In an embodiment and without limitation, support structure 1204 may include one or more gel-type support resins, surface-type support resins, and/or composite resins.

Still referring to FIG. 12, therapeutic oligomer 156 may include a first backbone element 1208a. As used in this disclosure a "backbone element" is a chemical and/or molecule that binds to another chemical and/or molecule as a function of a peptide bond. In an embodiment, and without limitation, backbone element 1208a may be comprised of N-(2-aminoethyl)-glycine. In another embodiment, and without limitation, backbone element 1208a may be comprised of deoxyribose. In another embodiment, and without limitation, backbone element 1208a may be comprised of ribose. In another embodiment, and without limitation, backbone element 1208a may be comprised of one or more neutral and/or charged phosphate groups. Additionally or alternatively, therapeutic oligomer 156 may include a second backbone element 1208b. Second backbone element 1208b may be comprised of any chemical and/or molecule that first backbone element 1208a may be comprised. In an embodiment, and without limitation, therapeutic oligomer 156 may be comprised of a plurality of backbone elements 1208n. In an embodiment, and without limitation, coupling the plurality of backbone elements 1208n may be bound as a function of a covalent bond, wherein a covalent bond is a chemical bond that involves sharing of electrons between atoms as described above, in reference to FIGS. 1-11. For example, and without limitation, covalent bond may include electron pairs that are shared and/or bonded as a function of a stable balance of attractive and/or repulsive forces between atoms. In an embodiment, and without limitation, covalent bond may allow molecules and/or atoms to fill one or more valence shells of an atom to produce a stable electronic configuration. In another embodiment, covalent bond may include one or more interactions such as, but not limited to σ-bonding, π-bonding, metal-to-metal bonding, agnostic interactions, bent bonds, three-center two-electron bonds, three-center four-electron bonds, and the like thereof.

Still referring to FIG. 12, therapeutic oligomer 156 may include a first nucleobase 1212a. As used in this disclosure a "nucleobase" is a chemical and/or molecule comprising a nitrogenous base. In an embodiment, and without limitation, first nucleobase 1212a may include one or more chemicals and/or molecules such as but not limited to adenine, cytosine, guanine, thymine, uracil, and the like thereof. In another embodiment, and without limitation, first nucleobase 1212a may be comprised of one or more primary and/or canonical nucleobases. In another embodiment, and without limitation, first nucleobase 1212a may be comprised of a purine base and/or a pyrimidine base. In another embodiment, and without limitation, first nucleobase 1212a may be comprised of one or more chemicals and/or molecules such as but not limited to xanthine, hypoxanthine, 2,6-diaminopurine, 6,8-diaminopurine, and the like thereof. In another embodiment, and without limitation, first nucleobase 1212a may be comprised of one or more chemicals and/or molecules such as but not limited 7-methylguanine, inosine, 7-methylguanosine, 5,6-dihydrouracil, 5-methylcytosine, 5-hydroxymethylcytosine, dihydrouridine, 5-methylcytidine, and the like thereof, and the like thereof. In another embodiment, and without limitation, first nucleobase 1212a may be comprised of one or more chemicals and/or molecules such as but not limited to aminoallyl nucleotides, isoguanine, isocytosine, 2-amino-6(2-thienyl) purine, pyrrole-2-carbaldehyde, and the like thereof. Additionally or alternatively, therapeutic oligomer 156 may include a second nucleobase 1212b. Second nucleobase 1212b may be comprised of any chemical and/or molecule that first nucleobase 1212a may be comprised. In an embodiment, and without limitation, therapeutic oligomer 156 may be comprised of a plurality of nucleobases 1212n.

Now referring to FIG. 13, an exemplary embodiment 1300 of downregulation of nanotherapeutic oligomers is illustrated. In an embodiment, nanotherapeutic oligomers may downregulate key proinflammatory genes implicated in neurodegeneration. Now referring to FIG. 13a, nanotherapeutic oligomer may downregulate of IL-1β 8-fold in unstimulated, wherein gamma-radiation stimulated (1 Gray or Gy) in donor-derived human peripheral blood mononuclear cells (PBMCs) may not be downregulated. Now referring to FIG. 13b, nanotherapeutic oligomer may downregulate IL-1α 4-fold. Now referring to FIG. 13c, nanotherapeutic oligomer may downregulate IL-6 gene 3-fold in comparison to untreated PBMCs. In an embodiment, and without limitation, more than 14-key proinflammatory cytokines implicated in neurodegeneration may be downregulated through nanotherapeutic oligomers.

Figures 14A, 14B, 14C:
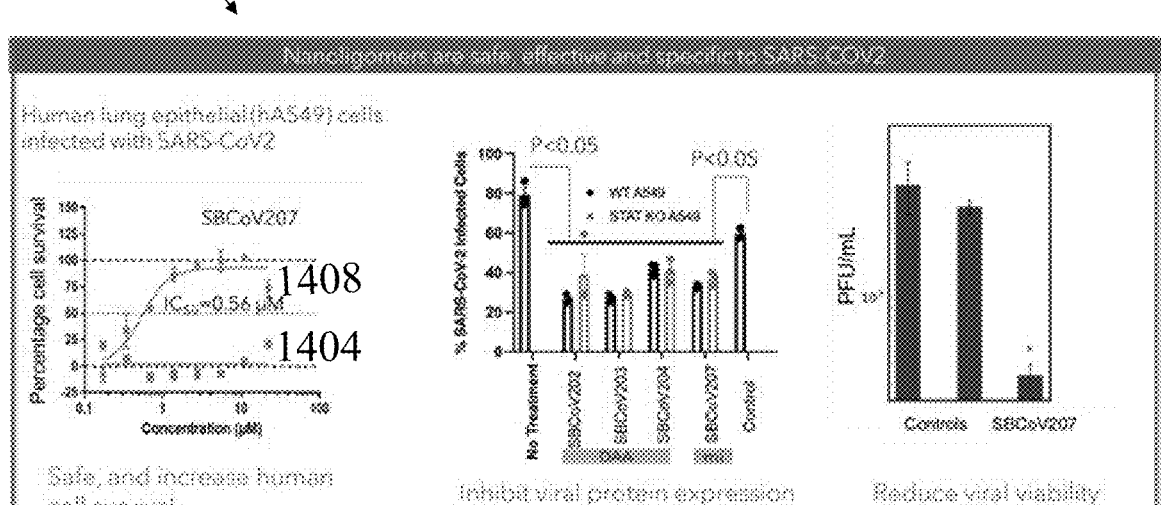
FIGS. 14A-C is a diagrammatic representation illustrating an exemplary embodiment of an antiviral therapeutic oligomer.

Now referring to FIG. 14, an exemplary embodiment 1400 of an antiviral therapeutic oligomer is illustrated. Now referring to FIG. 14a, a cytotoxicity and cell survival graph is represented. Graph may include a cytotoxicity element 1404 denoting the safety and/or cytotoxicity of SARS-CoV-2 antiviral, wherein the SARS-CoV-2 antiviral may be host-directed, targeting micro RNA mi2392. In an embodiment, cytotoxicity element 1404 may be represented as a curve on the graph. In another embodiment, graph may include a cell survival element 1408 denoting the cell survival of human lung epithelial cells (hA4549) infected with the SARS-CoV-2 viral agent. IN an embodiment, and without limitation, cytotoxicity element 1404 and cell survival element 1408 may demonstrate the safety and/or efficacy in an in vitro infection model when limited and/or no cytotoxicity occurs, wherein the restoration of survival over 3-5 μM is present. Now referring to FIG. 14*b* a viral clearance in the in vitro assay is represented. In an embodiment, and without limitation, viral clearance in the in vitro assay may show elimination of viral load as a function of using fluorescence tagging of viral protein and as a function of using three direct-acting and one host-directed SARS-CoV2 antiviral. Significant reduction of viral protein may demonstrate the ability of the nano-oligomer to clear out the infection, even in STAT-3 knockout cells. Now referring to FIG. 14*c*, an efficacy of clearing infection of SARS-CoV-2 viral agent is represented. In an embodiment, and without limitation, the efficacy and log-change in the plaque-forming unit (PFU) of the viral load may demonstrate demonstrating the efficacy of clearing infection SARS-CoV2 infection using therapeutic nano-oligomers as antiviral and anti-infectives.

Figures 15A, 15B:
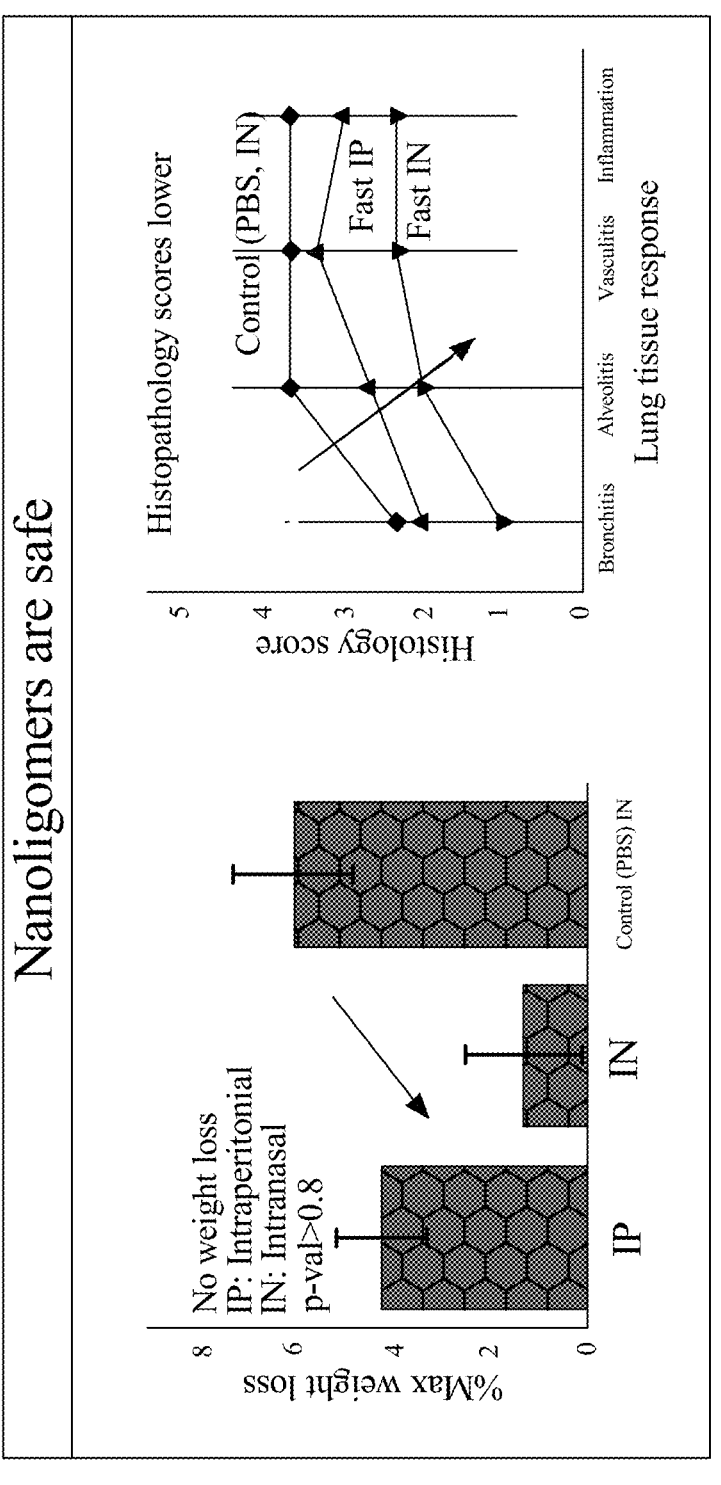
FIGS. 15A-C is a diagrammatic representation illustrating an exemplary embodiment of an in vivo efficacy assessment of therapeutic oligomer for treating SARS-CoV-2.
Figure 15C:
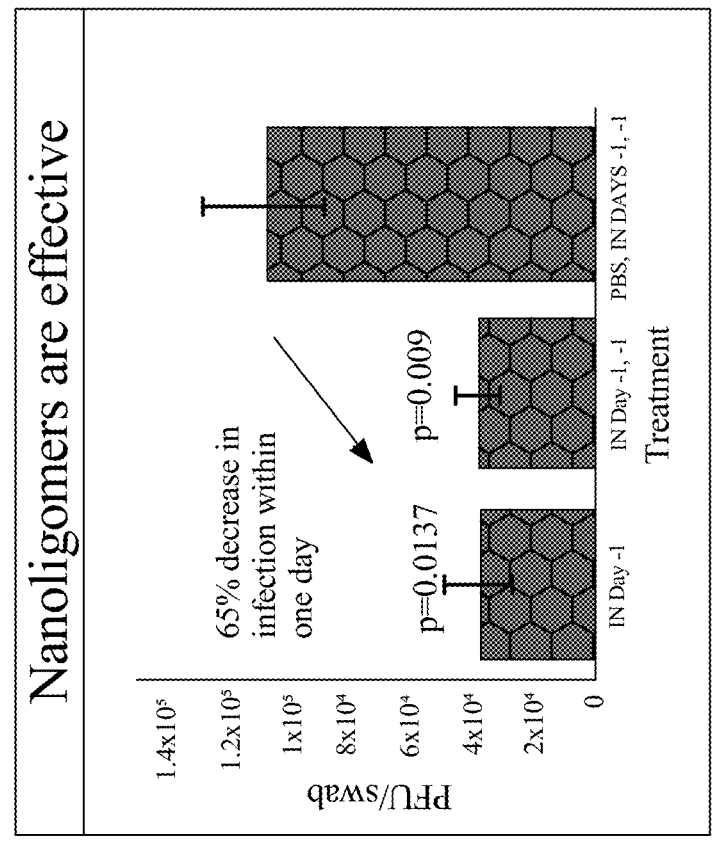

Now referring to FIG. 15, an exemplary embodiment 1500 of an in vivo efficacy assessment of therapeutic oligomer for treating SARS-CoV-2 is illustrated. In an embodiment and without limitation, in vivo efficacy assessment of therapeutic oligomer may be determined as a function of an in vivo assay in Syrian Hamsters, wherein the safety and efficacy assessment of designed host-directed nano-oligomers may be evaluated for safety as a function of a weight change in key organs, histopathology scores, and/or efficacy using plaque assays (plaque-forming unit (PFU) retrieved using a swab. Now referring to FIG. 15*a*, two different routes of administration, intranasal (IN) and intraperitoneal (IP), may be analyzed, wherein significant/statistical increases may be observed in weight loss, indicating the safety of the administered therapeutic oligomers. Now referring to FIG. 15*b*, histopathology scores for both routes of administration may be lower, wherein lower scores may represent more healthy organs, than control PBS, and wherein lower scores may indicate a high tolerability and/or safety profile, wherein a safety profile may represent a lack of any toxicity of inflammation due to the therapeutic, of the administrated therapeutic oligomers. Now referring to FIG. 15*c*, a plaque assay showing the efficacy in PFU of the viral load is illustrated, wherein the plaque assay showing the efficacy may represent the clearing of SARS-CoV2 infection using therapeutic oligomer as an effective antiviral.

Figure 16:
FIG. 16 is a diagrammatic representation illustrating an exemplary embodiment of a therapeutic effect of a nanotherapeutic oligomer
Figure 16:
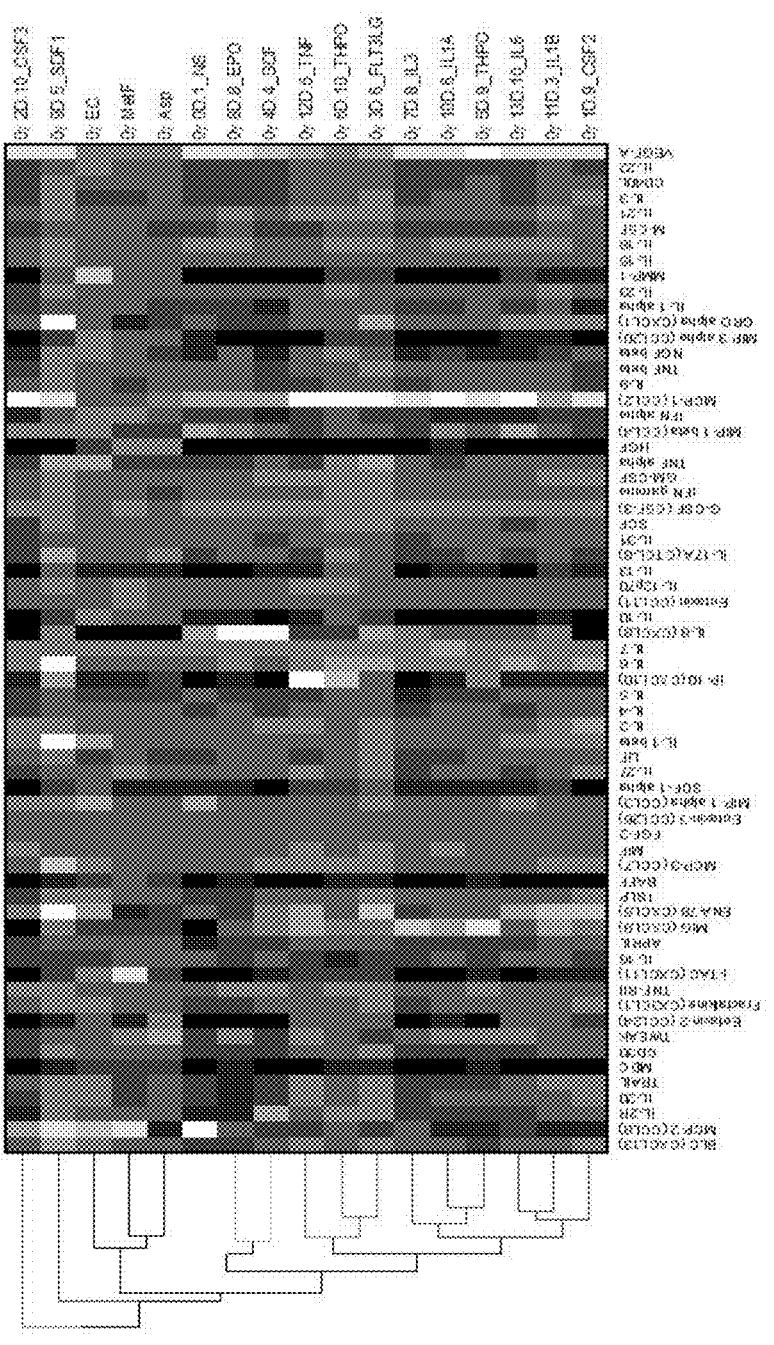

Now referring to FIG. 16, an exemplary embodiment 1600 of a therapeutic effect of a nanotherapeutic oligomer is illustrated. In an embodiment, and without limitation, nanotherapeutic oligomer may comprise a therapeutic effect of a significant reduction of key proinflammatory cytokines. For example, and without limitation, molecular targets may comprise G-CSF and/or Colony-stimulating factor 3 (CSF-3), Stromal cell-derived factor 1 (SDF-1), Epicatchetin (EC) as small molecule ROS inhibitor comparison, Metformin as small molecule non-sulfonylurea comparison, Aspirin as a small molecule comparison, Erythropoietin (EPO), Stem cell factor (SCF), TNF-α; Thrombopoietin (THPO), Fms related tyrosine kinase 3 ligand (FLT3LG), IL-3; IL-1α, THPO-isoform; IL-6; IL-1β and/or CSF-2. In an embodiment, an embodiment, and without limitation, nanotherapeutic oligomer may downregulate one or more molecular targets, wherein downregulating may comprise downregulating targeted cytokines/genes. In another embodiment, and without limitation, nanotherapeutic oligomer may reduce inflammation by downregulating cytokine expression all key inflammatory cytokines, for example but not limited to during neurodegeneration.

Figures 17A, 17B:
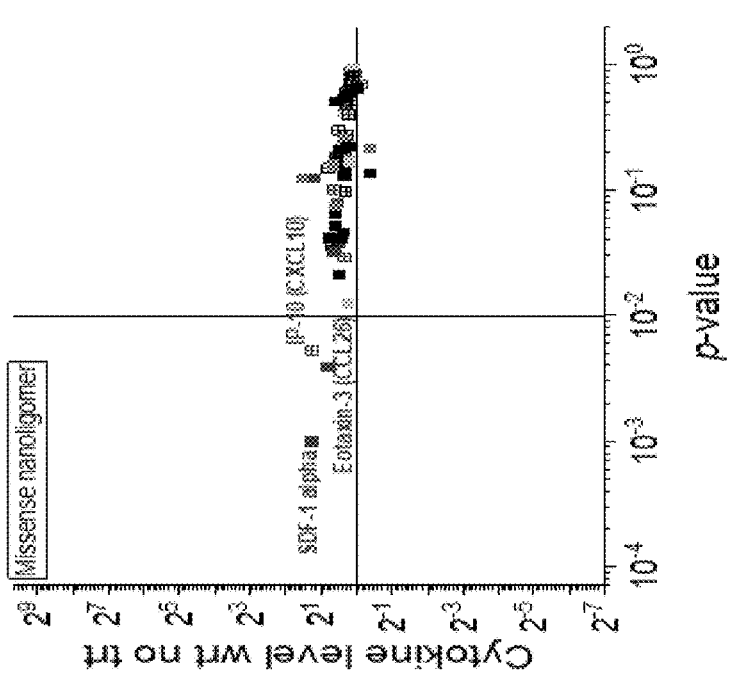
FIGS. 17A-B is a diagrammatic representation illustrating an exemplary embodiment of a toxicity of a therapeutic oligomer.
Figure 18C:
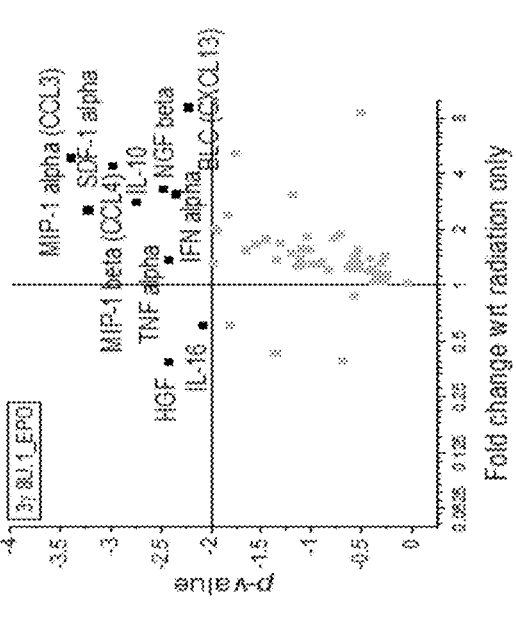
FIGS. 18A-C is a diagrammatic representation illustrating an exemplary embodiment of an efficacy of a therapeutic oligomer.
Figure 18B:
Figure 18B:
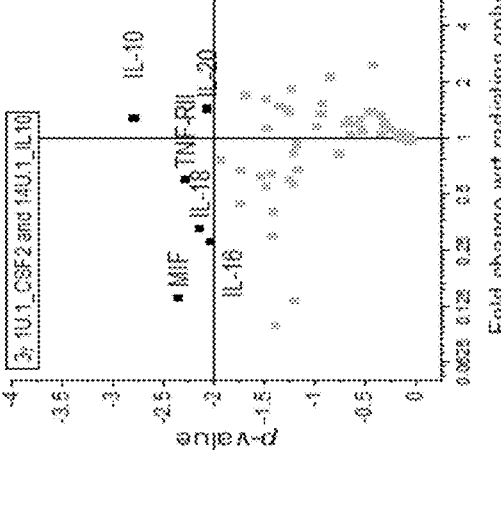
Figure 18A:
Figure 18A:
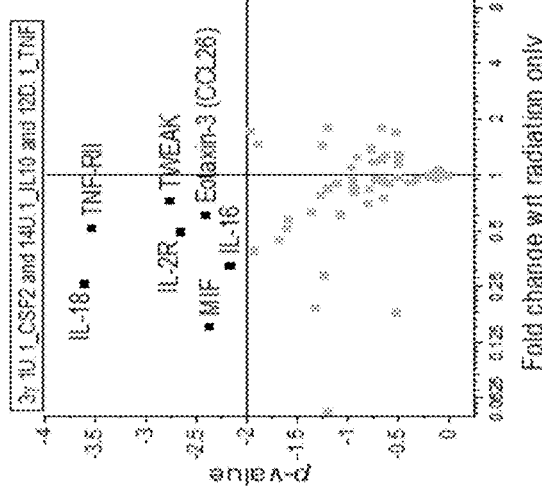

Now referring to FIG. 17, an exemplary embodiment 1700 of a toxicity of a therapeutic oligomer is illustrated. Referring to FIG. 17A, therapeutic oligomer for neurotherapeutic NF-kβ inhibitor and/or TNF-receptor 1 inhibitor may be exerted on human astrocytes, wherein no immunotoxicity may be represented. Referring to FIG. 17B, therapeutic oligomer comprising a missense nanoligomer may not show any immunotoxicity. In an embodiment, and without limitation, cytokine release syndrome may not be directly related to immunogenicity, wherein the clinical presentation of cytokine release syndrome may overlap with anaphylaxis and other immunologically related adverse reactions. In another embodiment, and without limitation, distinguishing the symptom complex from other types of adverse reactions may be potentially useful for risk mitigation. In another embodiment, and without limitation, the mechanism may relate to the cross-linking of activating cell surface-expressed receptors, which may be the targets of the therapeutic protein product (e.g., CD28 expressed on T-cells). In another embodiment, and without limitation, risk-based evaluation on the mechanism of action of the therapeutic protein product as well as results of animal and/or in vitro evaluations may be performed to determine the need for the collection of pre- and post-dose cytokine levels in the early phase of clinical development. In another embodiment, and without limitation, an evaluation may provide evidence to support the clinical diagnosis of cytokine release syndrome and help distinguish this entity from other acute drug reactions.

Now referring to FIG. 18, an exemplary embodiment 1800 of an efficacy of a therapeutic oligomer is illustrated. Referring now to FIG. 18A, therapeutic oligomer comprising an oligomer designed to upregulate GM-CSF and/or CSF2 may result in a significant increase in protein expression, wherein the increase may be measured as a function of cytokine quantification on PBMCs stimulated using 3Gy gamma radiation, and wherein protein expression may be a GM-CSF, associated G-CSF and other growth factor, and/or a significant number of proinflammatory (IL-1 α, IL-1 b, TNF-α, TNF receptors, etc.) cytokines and/or IL-10, included in the gene interaction network. Referring now to FIG. 18B, therapeutic oligomer comprising an oligomer designed to upregulate GM-CSF and/or CSF2 may result in a significant increase in protein expression, wherein the increase may be measured as a function of cytokine quantification on PBMCs stimulated using 3Gy gamma radiation, and wherein protein expression may be a GM-CSF, associated G-CSF and other growth factor, and/or a significant number of proinflammatory (IL-1 α, IL-1 b, TNF-α, TNF receptors, etc.) cytokines and/or IL-10, included in the gene interaction network. Referring now to FIG. 18C, therapeutic oligomer may upregulate hemopoietic proteins and/or proinflammatory enzymes. In an embodiment, and without limitation, therapeutic oligomer may reduce a probability of developing cancer as a function of upregulating hemopoietic proteins and/or associated growth factors.

Figure 19:
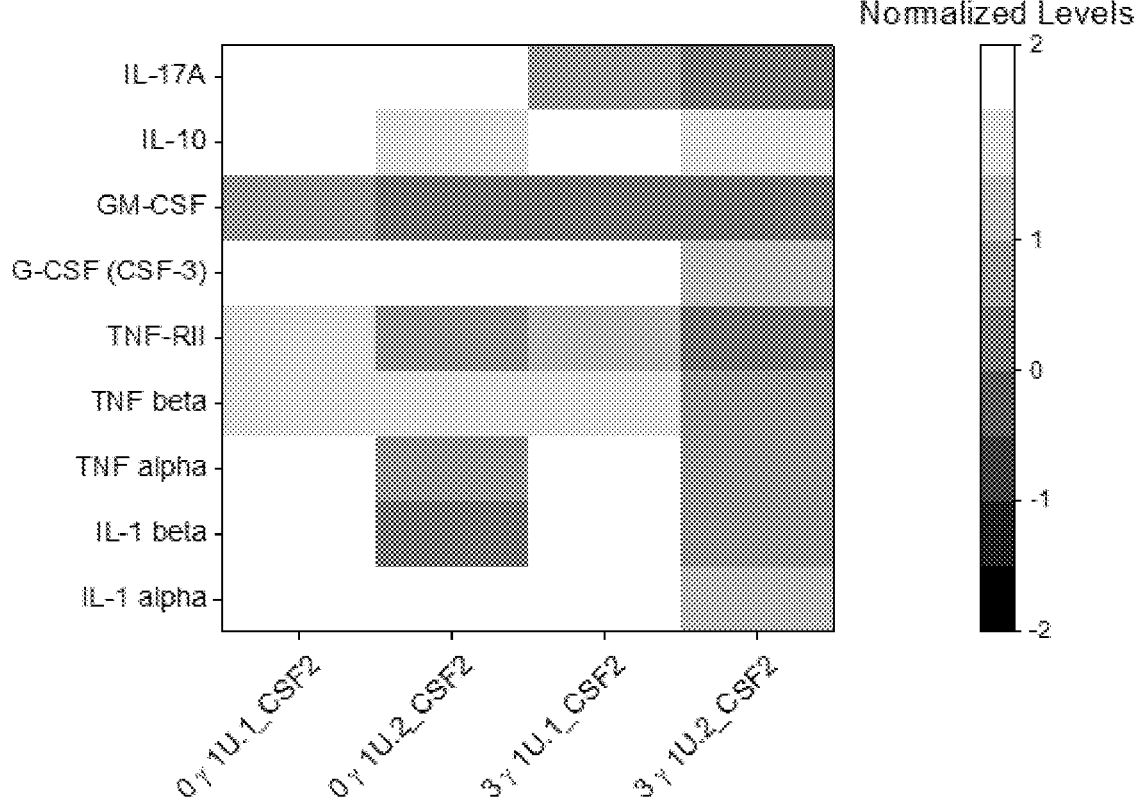
FIG. 19 is a diagrammatic representation illustrating an exemplary embodiment of a therapeutic effect of a nanotherapeutic oligomer.

Now referring to FIG. 19, an exemplary embodiment 1900 of a therapeutic effect of a nanotherapeutic oligomer is illustrated. In an embodiment, and without limitation, nanotherapeutic oligomer may comprise a therapeutic effect of upregulating growth factor and/or hemopoietic protein, wherein upregulating may comprise a significant increase in protein expression, such as but not limited to cytokine quantification on PBMCs stimulated using 3Gy gamma radiation, of targeted growth factor proinflammatory cytokines, such as but not limited to IL-1 α, IL-1 β, TNF-α, TNF receptors, and the like thereof, and/or IL-10.

Figure 20A:
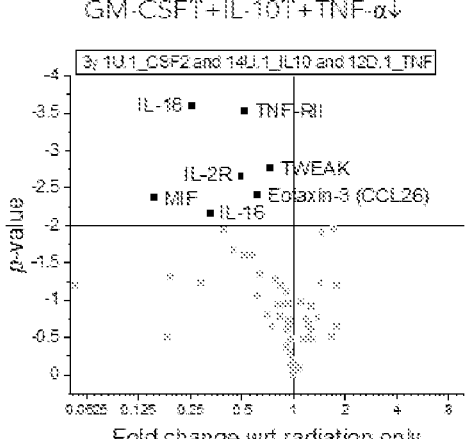
FIGS. 20A-B is a diagrammatic representation illustrating an exemplary embodiment of a therapeutic effect of a therapeutic oligomer.
Figure 20B:
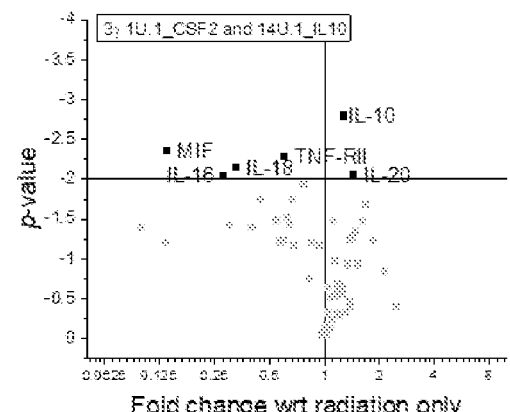

Now referring to FIG. 20, an exemplary embodiment of a therapeutic effect of a therapeutic oligomer is illustrated. Referring now to FIG. 20A, therapeutic effect of therapeutic oligomer may be multiplexed as a function of 10 mM each of CSF-2 upregulators, IL-10 upregulators, and/or TNF-α downregulators, wherein the multiplexed therapeutic oligomer may exert a therapeutic effect one or more cytokine expression profiles. Referring now to FIG. 20B, therapeutic effect of therapeutic oligomer may be multiplied as a function of 10 mM each of CSF-2 upregulators, and/or IL-10 upregulators, wherein the multiplexed therapeutic oligomer may reduce the increase in expression of proinflammatory cytokines and/or increase IL-10 expression. IN an embodiment, and without limitation, multiplexing therapeutic oligomers may allow for precise tuning of the therapeutic profile of immune engineering therapeutics.

Figure 21A:
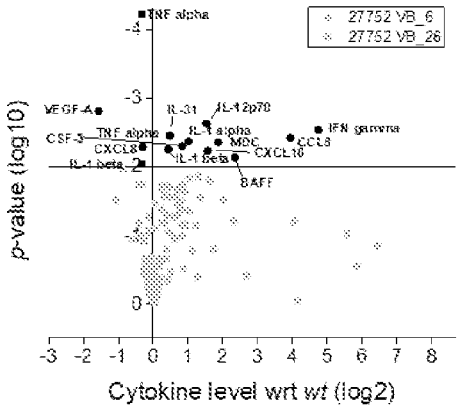
FIGS. 21A-B is a diagrammatic representation illustrating an exemplary embodiment of a genomic outcome.
Figure 21B:
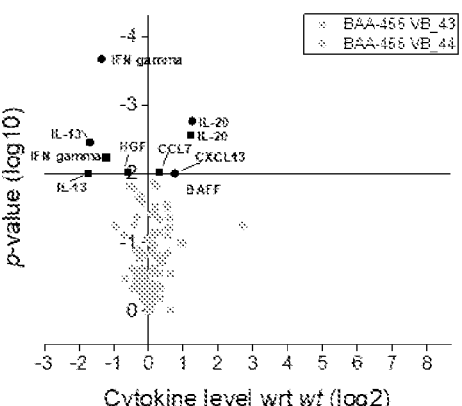

Now referring to FIG. 21, an exemplary embodiment of a genomic outcome is illustrated. In an embodiment, and without limitation, therapeutic oligomer may modulate one or more gene expressions in a range of genetically intractable anaerobes to tweak the human microbiome for a plurality of health and/or wellness purposes. Referring now to FIG. 21A, anaerobe BAA-455 *Pseudobutyrivibrio xylanivorans* may be cultured and two genes of interest may be identified from patients undergoing clinical trials for an immune checkpoint therapy: 1) Gene 1: Alpha/beta hydrolase family protein and 2) Gene 2: helix-turn-helix domain-containing protein. In an embodiment, and without limitation, an observed effect may be strong downregulation of pro-inflammatory cytokines and upregulation of anti-inflammatory cytokines as a function of designing their antisense therapeutic oligomers, treating the anaerobic cultures, collecting the cell lysates, and/or treating human PBMCs. In another embodiment, and without limitation, bacterial lysates may be used to isolate bacterial metabolites, wherein isolated bacterial metabolites may include product and/or metabolic sequencing, and/or therapeutic oligomers may be developed for oral delivery in an enteric polymer coating, to treat autoimmune diseases. Referring now to FIG. 21B, two or more genes, such as but not limited to Gene 1: metallohydrolase-like_MBL-fold and/or Gene 2: glf UDP-galactopyranose mutase, in anaerobe ATCC 27752 *Blautia hansenii* may be targeted to increase the expression of proinflammatory cytokines, wherein an exposure of bacterial lysates to human PBMCs may occur. In an embodiment, and without limitation, bacterial metabolites and/or therapeutic oligomers may be validated targets for the development of anticancer drugs by modulating the human microbiome.

Figure 22B:
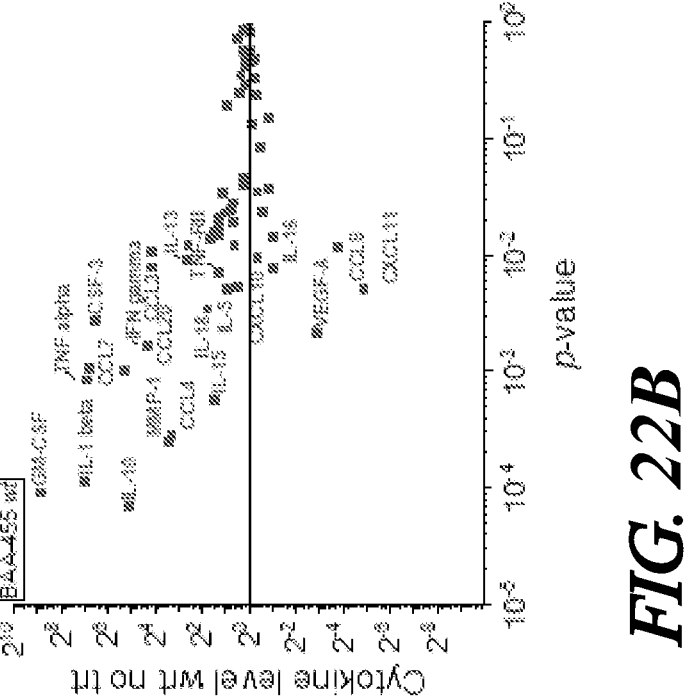
FIGS. 22A-B is a diagrammatic representation illustrating an exemplary embodiment of a therapeutic effect of a therapeutic oligomer.
Figure 22A:
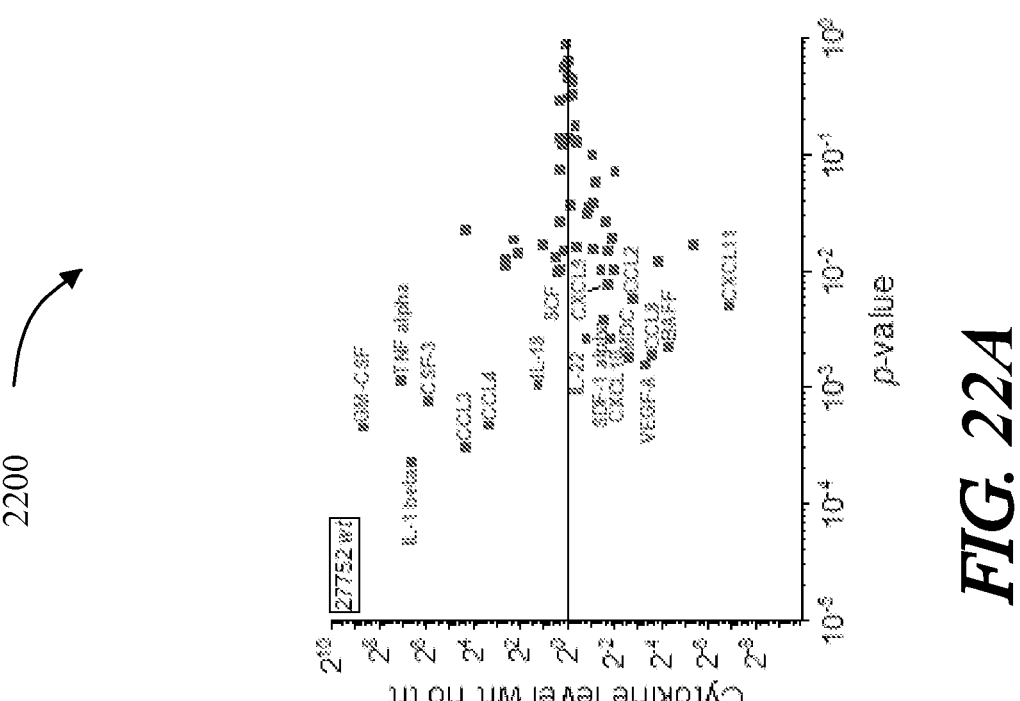
Figure 23A:
FIGS. 23A-C is a diagrammatic representation illustrating an exemplary embodiment of a therapeutic effect of a therapeutic oligomer.
Figure 23A:
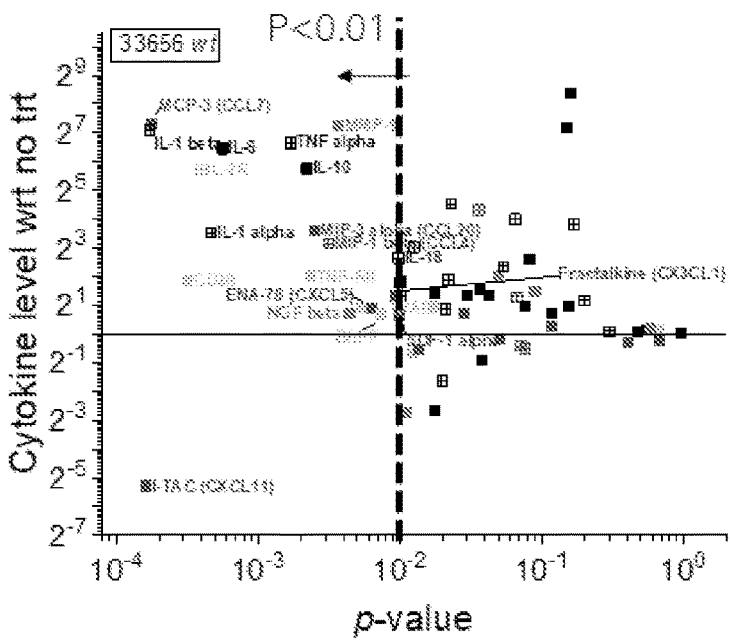
Figure 23B:
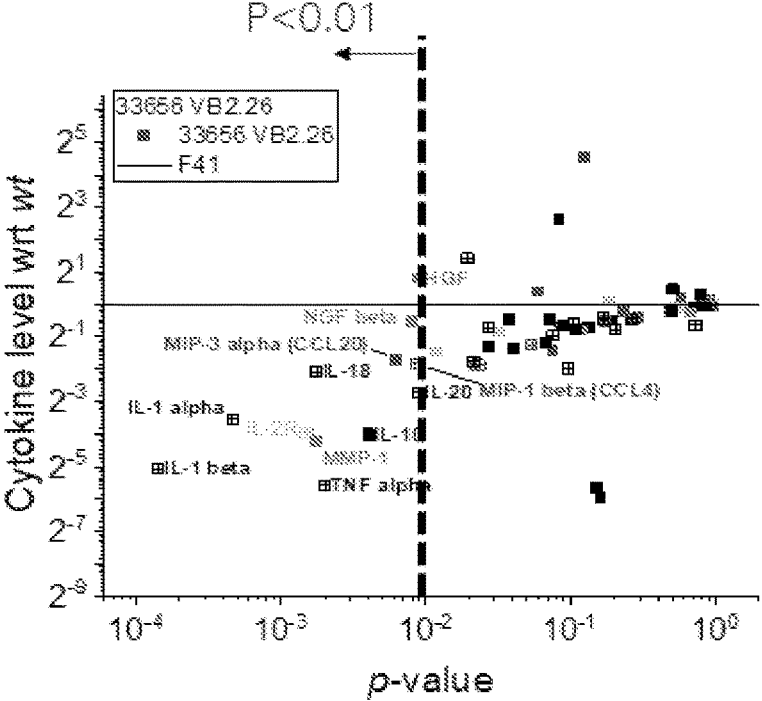
Figure 23C:
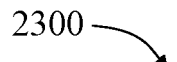
Figure 23C:
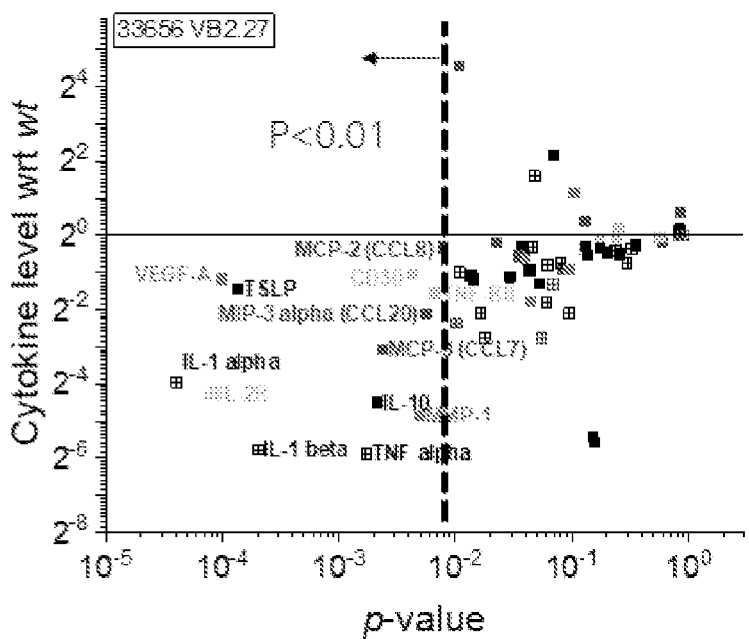

Now referring to FIG. 22, an exemplary embodiment of a therapeutic effect of a therapeutic oligomer is illustrated. In an embodiment, and without limitation, therapeutic effect may be an effect of target microbes on human cytokine expression. Referring now to FIG. 22A, bacterial lysates of *Pseudobutyrivibrio xylanivorans* (ATC27752), may be evaluated such that an impact on cytokine expression to develop bacterial metabolites and growth-promoting/inhibiting therapeutic oligomers to perturb the human microbiome may be determined. Referring now to FIG. 22B, bacterial lysates of *Blautia hansenii* (BAA-455), may be evaluated such that an impact on cytokine expression to develop bacterial metabolites and growth-promoting/inhibiting therapeutic oligomers to perturb the human microbiome may be determined. In an embodiment, and without limitation, *Pseudobutyrivibrio xylanivorans* (ATCC 27752) and/or *Blautia hansenii* (BAA-455) may both promote growth factors, such as but not limited to GM-CSF, G-CSF and/or pro-inflammatory cytokine expression, which may result in a desired drug profile for promoting growth while ensuring the elimination of cancer development. In an embodiment, and without limitation, any undesired change in cytokines or other protein expressions may be easily targeted/eliminated and/or expression of desired proteins further increased as a function of addition of desired therapeutic oligomers.

Now referring to FIG. 23, an exemplary embodiment of a therapeutic effect of a therapeutic oligomer is illustrated. In an embodiment, and without limitation, therapeutic effect of therapeutic oligomer may include a therapeutic effect on a human microbiome. Referring now to FIG. 23A, therapeutic effect may include an effect of *Eubacterium rectale* bacterial lysates on a human microbiome, wherein the therapeutic effect may lead to a strong increase in pro-inflammatory cytokine expression in human PBMCs. Referring now to FIG. 23B, an addition of antisense therapeutic oligomer may target scfB thioether cross-link-forming SCIFF peptide maturase gene in *Eubacterium rectale*, wherein the addition may lead to strong anti-inflammatory cytokine and/or reduction in pro-inflammatory cytokine production. Referring now to FIG. 23C, an addition antisense of therapeutic oligomer may result in a therapeutic effect of targeting peptidase domain-containing ABC transporter gene in *Eubacterium rectale*, wherein the therapeutic effect may lead to strong anti-inflammatory cytokine expression. In an embodiment, and without limitation, all three bacterial metabolites and two therapeutic oligomers may be developed as health and wellness products. In another embodiment, and without limitation, an anti-inflammatory response may be used for targeting autoimmune diseases, such as but not limited to Crohn's and colitis, inflammatory bowel disease, and/or the proinflammatory cytokines for anticancer drugs using the human microbiome.

Figure 24:
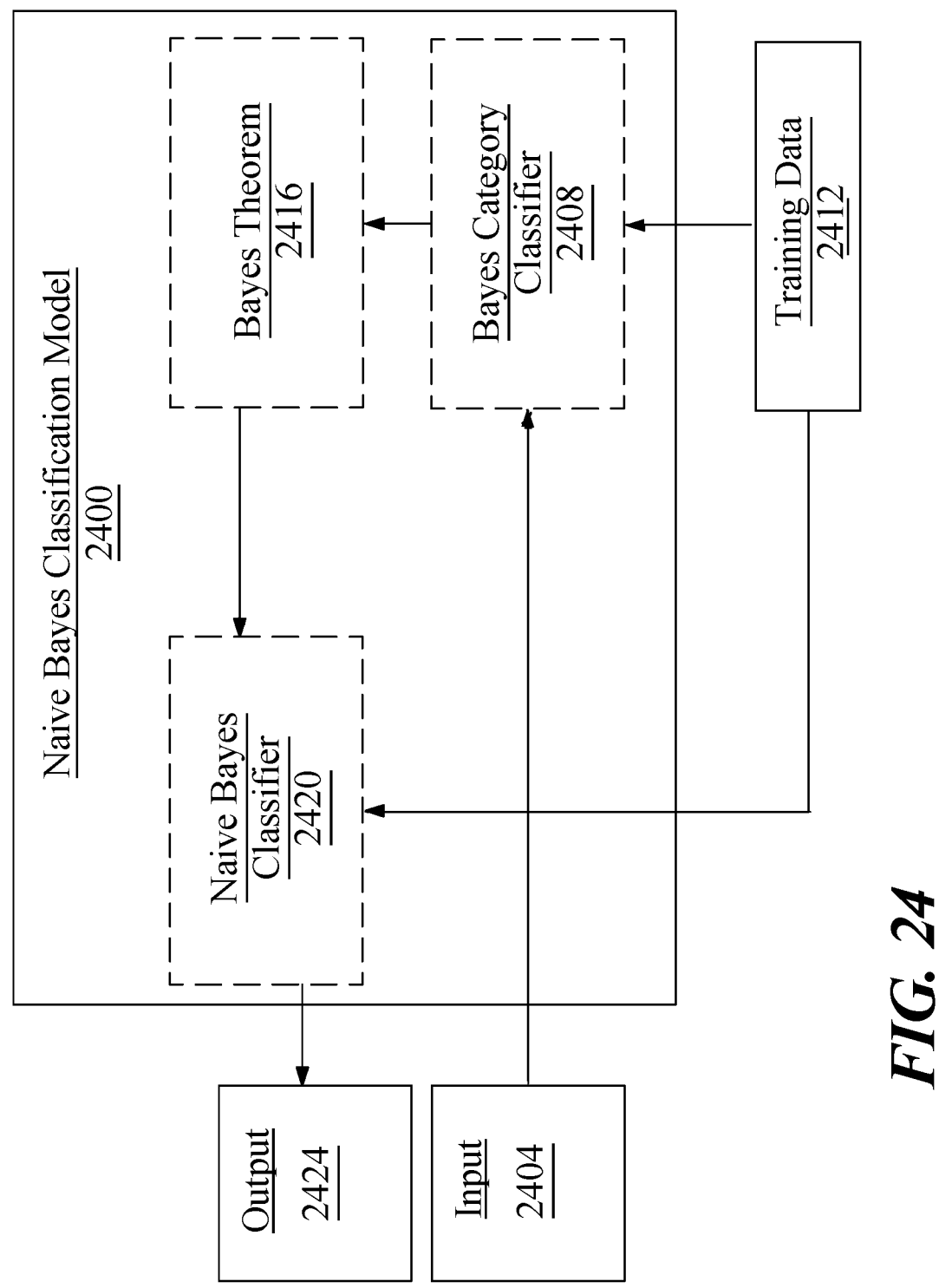
FIG. 24 is a block diagram of an exemplary embodiment of a naïve bayes classifier.

Referring now to FIG. 24, an exemplary embodiment of a Naïve Bayes classification model 2400 that may perform one or more machine-learning processes as described in this disclosure is illustrated. A Naïve Bayes classification model 2400 may be configured to classify inputs 2404 into a plurality of Bayes categories. Naïve Bayes classification algorithm generates classifiers by assigning Bayes categories to inputs 2404. In embodiments, this may be done using a bayes category classifier 2408. As used in the current disclosure, a "bayes category classifier" is a machine-learning model that sorts inputs into categories or bins of data, outputting the categories or bins of data and/or labels associated therewith. The Bayes category classifier 2408 receives input 2404 and sorts the input into a plurality of a Bayes categories and Bayes Vectors. As used in the current disclosure, a "Bayes category" is a set of categories specific to a given input. Bayes categories may comprise both categories and subcategories, whereas the categories include possible outcomes for the Naïve Bayes classification model 2400 and the subcategories may include variables that are outcome determinative for the classification model 2400. Bayes categories and subcategories are drawn from a finite set of variables within an input 2404. In a non-limiting example, if a user is trying to classify emails in to two categories, spam, and non-spam, the Bayes sub-categories may include words that are commonly used within both spam and non-spam emails. Once the inputs 2404 are classified into Bayes categories and subcategories they may be represented as Bayes vector. In embodiments, Bayes categories and subcategories may be reflected as histogram or a frequency table. As used in the current disclosure, "Bayes vector" are the enumeration of each input within a given Bayes category. Continuing with the above non-limiting example, a Bayes vector is quantity of times a given word occurs in a bayes subcategory.

Still Referring to FIG. 24, "training data," as used herein, is data containing correlations that a machine-learning process may use to model relationships between two or more categories of data elements. For instance, and without limitation, training data 2412 may include a plurality of data entries, each entry representing a set of data elements that were recorded, received, and/or generated together; data elements may be correlated by shared existence in a given data entry, by proximity in a given data entry, or the like. In embodiments, training data 2412 may be the same or substantially similar to the training data disclosed within FIG. 7. Training data may identification of Bayes categories and subcategories. Training data may additionally include outcomes of previous Naïve Bayes classification model 2400.

Still Referring to FIG. 24, a Naïve Bayes classification model 2400 may apply the Bayes Theorem 2416 as a function of the output of the output of Bayes category classifier 2408. As used in the current disclosure, the "Bayes Theorem" is describes the probability of an event, based on prior knowledge of conditions that might be related to the event. For example, if the risk of developing health problems is known to increase with age, Bayes theorem 2416 allows the risk to an individual of a known age to be assessed more accurately (by conditioning it on their age) than simply assuming that the individual is typical of the population as a whole. In embodiments, the Bayes Theorem 2416 may be expressed as $P(A/B)=P(B/A) \ P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. In embodiments, applying the bayes theorem 2416 may include replacing variables with the Bayes vectors and Bayes categories and subcategories.

Still Referring to FIG. 24, a Naïve Bayes classification model 2400 may be configured to generate a Naïve Bayes classifier 2420 as a function of the application of the Bayes Theorem 2416. As used in the current disclosure, "Naïve Bayes classifiers" are a family of probabilistic classifiers based on applying Bayes' theorem with strong (naive) independence assumptions between the features. In an embodiment, Naïve Bayes Classifier 2420 may include a classifier, or a machine learning model as defined herein above in FIG. 7. Naïve Bayes classifier 2420 may include generating a family of algorithms that assume that the value of a particular element is independent of the value of any other element, given a class variable. A Naïve Bayes classifier 2420 may include a multinomial Naïve Bayes Classifier or a Gaussian Naïve Bayes Classifier. Naïve Bayes classification module may be implemented as any hardware and/or software module. Naïve Bayes classification module may be configured to generate a Naïve Bayes classification algorithm. A Naïve Baynes classifier 2420 may additionally be trained using training data 2412.

Still referring to FIG. 24, Naive Baynes classifier 2420 may be configured to output 2424 a posterior probability as a function input 2404. Bayes categories and subcategories may utilize a Bayes Theorem 2416 to calculate a posterior probability for each class. As used in the current disclosure, a "posterior probability" is a type of conditional probability that results from updating the prior probability with information summarized by the likelihood, through an application of Bayes theorem 2416. The posterior probability distribution may describe the epistemic uncertainty about statistical parameters conditional on a collection of observed data. From a given posterior distribution, various point and interval estimates can be derived, such as the maximum a posteriori (MAP) or the highest posterior density interval (HPDI). A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Figure 25:
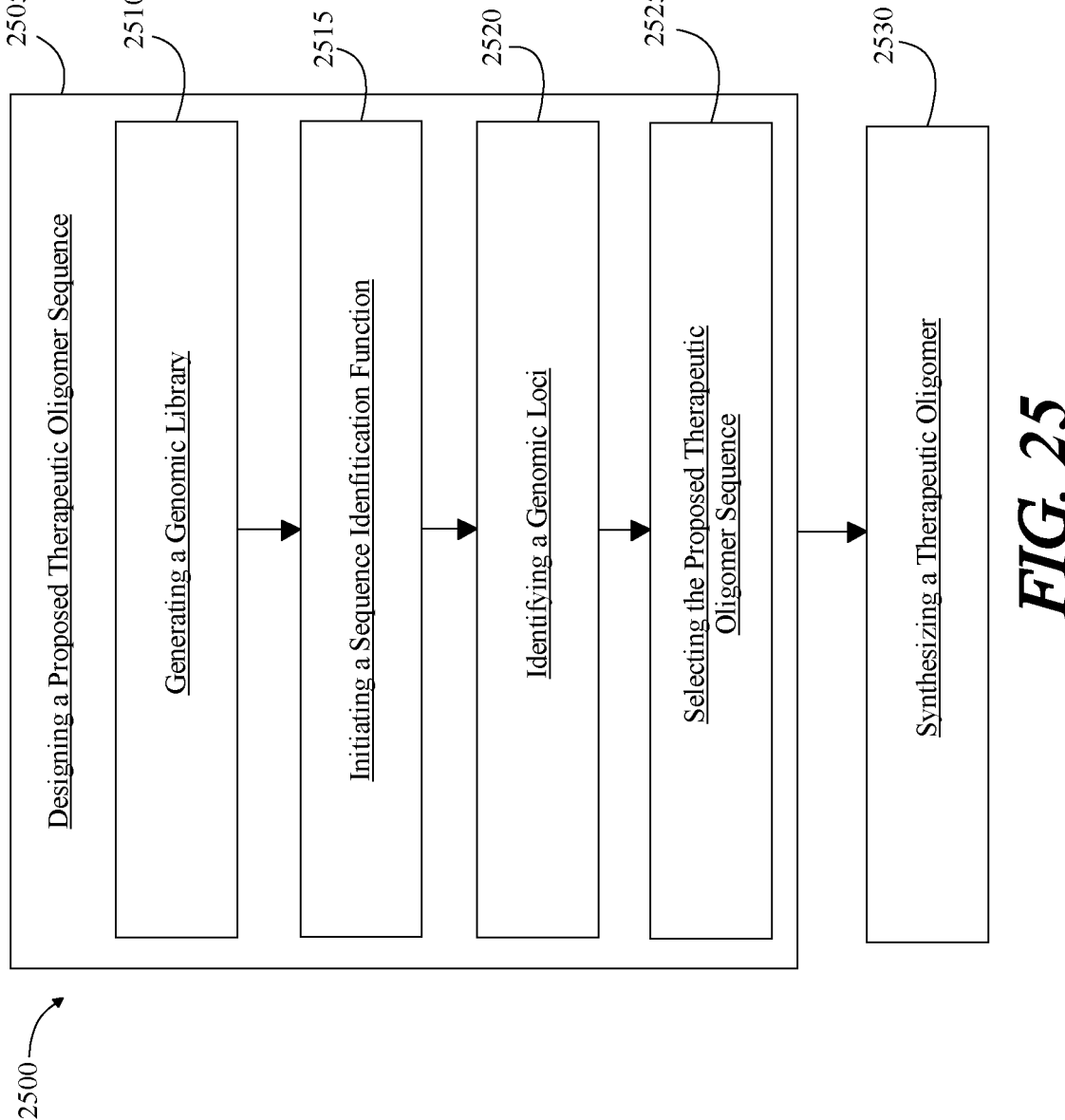
FIG. 25 is a flow diagram illustrating a method for producing a therapeutic oligomer.

Now referring to FIG. 25, a method for producing a therapeutic oligomer is illustrated. At step 2505 a computing device 104 designs a proposed therapeutic oligomer sequence 108. Computing device 104 includes any of computing device 104 as described above, in reference to FIGS. 1-24. Therapeutic oligomer 108 includes any of the therapeutic oligomer 108 as described above, in reference to FIGS. 1-24.

Still referring to FIG. 25, at step 2510, computing device 104 generates a genomic library 112 for an organism. Genomic library 112 includes any of the genomic library 112 as described above, in reference to FIGS. 1-24. Computing device 104 generates genomic library 112 for an organism from a gene target 116. Gene target 116 includes any of the gene target 116 as described above, in reference to FIGS. 1-24.

Still referring to FIG. 25, at step 2515, computing device 104 initiates a sequence identification function 120. Sequence identification function 120 includes any of the sequence identification function 120 as described above, in reference to FIGS. 1-24. Computing device 104 initiates sequence identification function 120 as a function of identifying a plurality of prospective gene targets 124 as a function of genomic library 112. Prospective gene target 116 includes any of the prospective gene target 124 as described above, in reference to FIGS. 1-24. Computing device 104 initiates sequence identification function 120 as a function of generating proposed therapeutic oligomer sequence 108 as a function of the plurality of prospective gene targets 124 and an oligomeric machine learning model 128. Oligomeric machine-learning model 128 includes any of the oligomeric machine-learning model 128 as described above, in reference to FIGS. 1-24. Oligomeric machine-learning model 128 is trained as a function of an oligomeric training set. Oligomeric training set includes any of the oligomeric training set as described above, in reference to FIGS. 1-24. Oligomeric training set correlates the plurality of prospective gene targets to an oligomer that regulates a gene expression. Oligomer that regulates gene expression includes any of the oligomer that regulates gene expression as described above, in reference to FIGS. 1-24.

Still referring to FIG. 25, at step 2520, computing device 104 identifies a genomic locus 132 that proposed therapeutic oligomer sequence 108 is predicted to bond to as a function of an off-target sequence function 136. Genomic locus 132 includes any of the genomic locus 132 as described above, in reference to FIGS. 1-24. Off-target sequence function 136 includes any of the off-target sequence function 136 as described above, in reference to FIGS. 1-24. Computing device 104 identifies an incidental alignment 140 as a function of proposed therapeutic oligomer sequence 108 and genomic library 108. Incidental alignment 140 includes any of the incidental alignment 140 as described above, in reference to FIGS. 1-24. Computing device 104 identifies genomic locus 132 as a function of modeling incidental alignment 140 to a corresponding genome assembly location 144. Genome assembly location 144 includes any of the genome assembly location 144 as described above, in reference to FIGS. 1-24. Computing device identifies genomic locus 132 as a function of incidental alignment 140 model and an overlap element 148. Overlap element 148 includes any of the overlap element 148 as described above, in reference to FIGS. 1-24.

Still referring to FIG. 25, at step 2525, computing device 104 selects proposed therapeutic oligomer sequence 108 as a function of sequence identification function 120, genomic locus 132, and a criterion element 152. Criterion element 152 includes any of the criterion element 152 as described above, in reference to FIGS. 1-24.

Still referring to FIG. 25, at step 2530, computing device 104 synthesizes a therapeutic oligomer 156 as a function of proposed therapeutic oligomer sequence 108. Therapeutic oligomer 156 includes any of the therapeutic oligomer 156 as described above, in reference to FIGS. 1-24. In an embodiment, and without limitation, computing device 104 may synthesize therapeutic oligomer 156 as a function of an automated synthesizer 160. Automated synthesizer 160 includes any of the automated synthesizer 160 as described above, in reference to FIGS. 1-24. In an embodiment, and without limitation, computing device 104 may update genomic library 112 as a function of therapeutic oligomer 156.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 26:
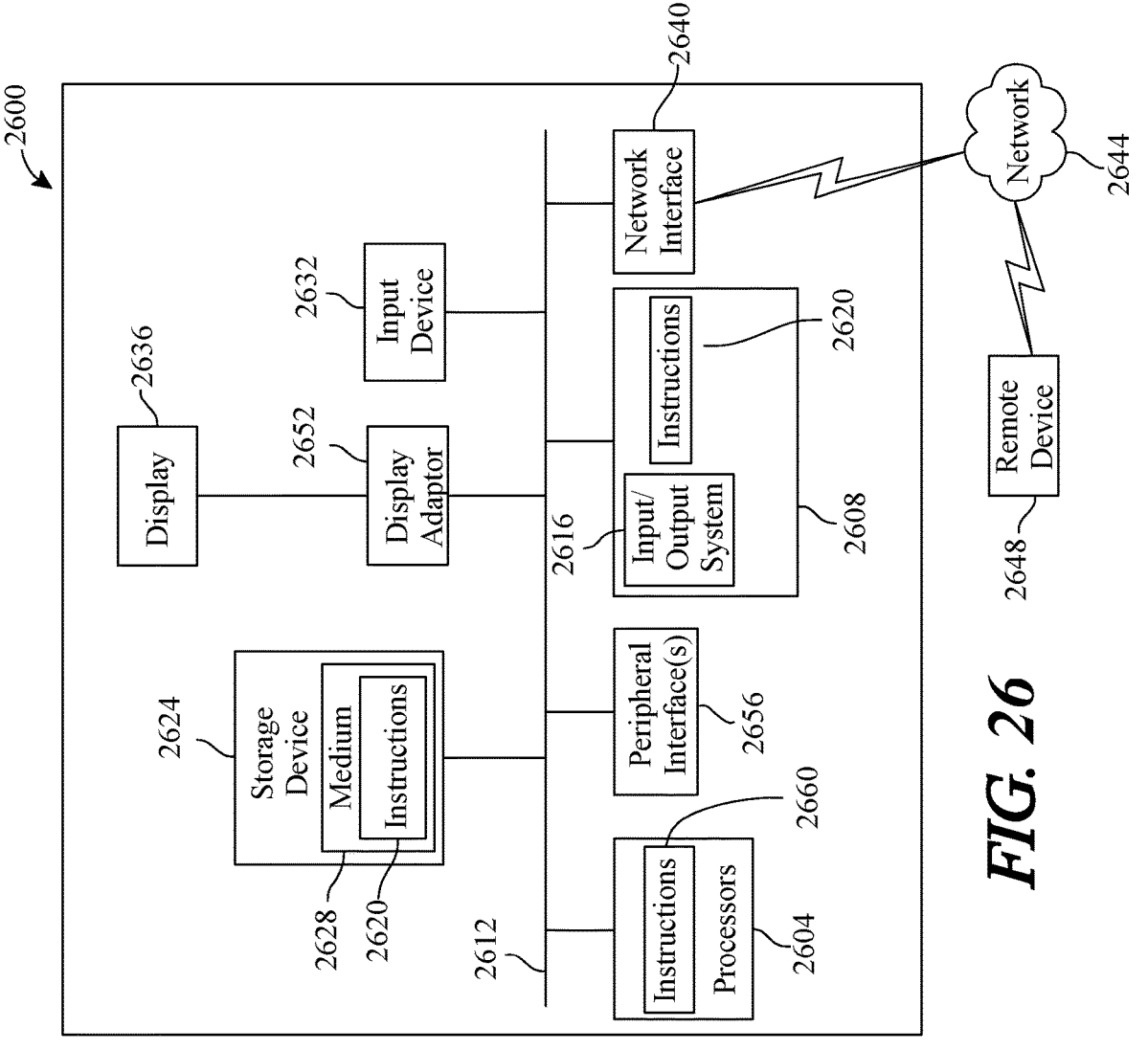
FIG. 26 is a block diagram of a computing system that can be used to implement any one or more of the methodologies disclosed herein and any one or more portions thereof.

FIG. 26 shows a diagrammatic representation of one embodiment of a computing device in the exemplary form of a computer system 2600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2600 includes a processor 2604 and a memory 2608 that communicate with each other, and with other components, via a bus 2612. Bus 2612 may include any of several types of bus structures including, but not limited to, a memory bus, a memory controller, a peripheral bus, a local bus, and any combinations thereof, using any of a variety of bus architectures.

Processor 2604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 2604 may be organized according to Von Neumann and/or Harvard architecture as a non-limiting example. Processor 2604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 2608 may include various components (e.g., machine-readable media) including, but not limited to, a random-access memory component, a read only component, and any combinations thereof. In one example, a basic input/output system 2616 (BIOS), including basic routines that help to transfer information between elements within computer system 2600, such as during start-up, may be stored in memory 2608. Memory 2608 may also include (e.g., stored on one or more machine-readable media) instructions (e.g., software) 2620 embodying any one or more of the aspects and/or methodologies of the present disclosure. In another example, memory 2608 may further include any number of program modules including, but not limited to, an operating system, one or more application programs, other program modules, program data, and any combinations thereof.

Computer system 2600 may also include a storage device 2624. Examples of a storage device (e.g., storage device 2624) include, but are not limited to, a hard disk drive, a magnetic disk drive, an optical disc drive in combination with an optical medium, a solid-state memory device, and any combinations thereof. Storage device 2624 may be connected to bus 2612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2624 (or one or more components thereof) may be removably interfaced with computer system 2600 (e.g., via an external port connector (not shown)). Particularly, storage device 2624 and an associated machine-readable medium 2628 may provide nonvolatile and/or volatile storage of machine-readable instructions, data structures, program modules, and/or other data for computer system 2600. In one example, software 2620 may reside, completely or partially, within machine-readable medium 2628. In another example, software 2620 may reside, completely or partially, within processor 2604.

Computer system 2600 may also include an input device 2632. In one example, a user of computer system 2600 may enter commands and/or other information into computer system 2600 via input device 2632. Examples of an input device 2632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2632 may be interfaced to bus 2612 via any of a variety of interfaces (not shown) including, but not limited to, a serial interface, a parallel interface, a game port, a USB interface, a FIRE-WIRE interface, a direct interface to bus 2612, and any combinations thereof. Input device 2632 may include a touch screen interface that may be a part of or separate from display 2636, discussed further below. Input device 2632 may be utilized as a user selection device for selecting one or more graphical representations in a graphical interface as described above.

A user may also input commands and/or other information to computer system 2600 via storage device 2624 (e.g., a removable disk drive, a flash drive, etc.) and/or network interface device 2640. A network interface device, such as network interface device 2640, may be utilized for connecting computer system 2600 to one or more of a variety of networks, such as network 2644, and one or more remote devices 2648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 2644, may employ a wired and/or a wireless mode of communication. In general, any network topology may be used. Information (e.g., data, software 2620, etc.) may be communicated to and/or from computer system 2600 via network interface device 2640.

Computer system 2600 may further include a video display adapter 2652 for communicating a displayable image to a display device, such as display device 2636. Examples of a display device include, but are not limited to, a liquid crystal display (LCD), a cathode ray tube (CRT), a plasma display, a light emitting diode (LED) display, and any combinations thereof. Display adapter 2652 and display device 2636 may be utilized in combination with processor 2604 to provide graphical representations of aspects of the present disclosure. In addition to a display device, computer system 2600 may include one or more other peripheral output devices including, but not limited to, an audio speaker, a printer, and any combinations thereof. Such peripheral output devices may be connected to bus 2612 via a peripheral interface 2656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A therapeutic oligomer composition, wherein the composition comprises:
   a therapeutic oligomer configured to regulate gene expression of a gene target within a target host, wherein the therapeutic oligomer comprises:
      at least a peptide nucleic acid (PNA) comprising at least a synthetic DNA-analog and 2-N-aminoethyl-glycine;
      a delivery nanoparticle comprising a Au22 to Au25 cluster and coated with glutathione; and
      a nanoparticle binding element comprising a 5-histidine sequence, wherein the nanoparticle binding element comprises a first end attached to the at least a PNA and a second end attached to the delivery nanoparticle to enable crossing of a blood-brain barrier.

2. The composition of claim 1, wherein the gene target comprises NLRP3.

3. The composition of claim 1, wherein the gene target comprises nuclear factor kappa-B (NF-κβ).

4. The composition of claim 1, wherein the gene target comprises Granulocyte-Macrophage Colony-Stimulating Factor (GM-CSF).

5. The composition of claim 1, wherein the gene target comprises tumor necrosis factor-alpha (TNF-α).

6. The composition of claim 1, wherein the gene target comprises Interleukin 10 (IL-10).

7. The composition of claim 1, wherein the gene target comprises Interleukin-1β (IL-1β).

8. The composition of claim 1, wherein the at least a PNA inhibits gene expression in a target host.

9. The composition of claim 1, wherein the at least a PNA upregulates gene expression in a target host.

10. The composition of claim 1, wherein the therapeutic oligomer additionally comprises a nano-oligomer.

11. The composition of claim 1, wherein the therapeutic oligomer is synthesized, using a computing device, as a function of the therapeutic oligomer.

12. The composition of claim 11, wherein the PNA is synthesized using a solid phase PNA synthesis comprising an Fmoc synthesis.

13. The composition of claim 1, further comprising a vector delivery system.

14. The composition of claim 1, wherein the therapeutic oligomer further comprises an antisense oligonucleotide.

15. The composition of claim 1, wherein a glycine carbonyl unit replaces a phosphate backbone of the at least a synthetic DNA-analog.

16. The composition of claim 1, wherein the at least a PNA comprises a modified phosphate backbone.

17. The composition of claim 16, wherein the modified phosphate backbone comprises at least phosphorodithioate.

18. The composition of claim 16, wherein the modified phosphate backbone comprises at least formacetal.

19. The composition of claim 16, wherein the modified phosphate backbone comprises at least methylphosphonate.

20. The composition of claim 16, wherein the modified phosphate backbone comprises at least alkyl phosphotrieste.

21. The composition of claim 1, wherein the delivery nanoparticle has a total hydrodynamic size of less than 2 nm.

22. The composition of claim 1, wherein the therapeutic oligomer further comprises a cellular uptake domain.

23. The composition of claim 1, wherein the target host comprises a pathogen or viral agent.

24. The composition of claim 1, further comprising a sequence to stimulate a metabolite drug.

\* \* \* \* \*